United States Patent
Ogita et al.

(10) Patent No.: US 11,778,903 B2
(45) Date of Patent: Oct. 3, 2023

(54) ORGANIC COMPOUND, LIGHT-EMITTING DEVICE, LIGHT-EMITTING APPARATUS, ELECTRONIC DEVICE, AND LIGHTING DEVICE

(71) Applicant: Semiconductor Energy Laboratory Co., Ltd., Kanagawa-ken (JP)

(72) Inventors: Kaori Ogita, Kanagawa (JP); Anna Tada, Kanagawa (JP); Sachiko Kawakami, Kanagawa (JP); Nobuharu Ohsawa, Kanagawa (JP); Satoshi Seo, Kanagawa (JP)

(73) Assignee: Semiconductor Energy Laboratory Co., Ltd.

( * ) Notice: Subject to any disclaimer, the term of this patent is extended or adjusted under 35 U.S.C. 154(b) by 625 days.

(21) Appl. No.: 16/923,343

(22) Filed: Jul. 8, 2020

(65) Prior Publication Data
US 2021/0013419 A1    Jan. 14, 2021

(30) Foreign Application Priority Data
Jul. 12, 2019   (JP) .................................. 2019-130550

(51) Int. Cl.
H10K 85/60   (2023.01)
C07D 513/04   (2006.01)
(Continued)

(52) U.S. Cl.
CPC ......... H10K 85/636 (2023.02); C07D 513/04 (2013.01); C09K 11/06 (2013.01);
(Continued)

(58) Field of Classification Search
CPC .............. H10K 85/636; H10K 85/657; H10K 85/6572; H10K 50/846; H10K 50/858;
(Continued)

(56) References Cited

U.S. PATENT DOCUMENTS 7,696,348 B2 * 4/2010 Egawa ................. C07D 241/12
548/440
7,901,792 B2   3/2011 Egawa et al.
(Continued)

FOREIGN PATENT DOCUMENTS

JP    2014-082405 A    5/2014
JP    2017-114853 A    6/2017

OTHER PUBLICATIONS

Yamanaka, T. et al., "Near-Infrared Organic Light-Emitting Diodes for Biosensing with High Operating Stability," Applied Physics Express, Jun. 7, 2017, vol. 10, No. 7, pp. 074101-1-074101-4.

Primary Examiner — Shane Fang
(74) Attorney, Agent, or Firm — Husch Blackwell LLP

(57) ABSTRACT

A novel organic compound having an emission spectrum peak at a wavelength longer than 850 nm and an absorption spectrum peak at a wavelength longer than 600 nm is provided. The organic compound is represented by General Formula (G1).

(Continued)

In General Formula (G1), $Ar^1$ to $Ar^4$ each independently represent an aryl group having 6 to 13 carbon atoms in a ring. $R^1$ to $R^8$ each independently represent anyone of hydrogen, an alkyl group having 1 to 6 carbon atoms, a cycloalkyl group having 3 to 6 carbon atoms, an aryl group having 6 to 13 carbon atoms in a ring, and a heteroaryl group having 3 to 13 carbon atoms in a ring. $Q^1$ and $Q^2$ each independently represent a group having a carbazole skeleton or a group having a triarylamine skeleton and having 18 to 30 carbon atoms in a ring. Furthermore, m and n each independently represent 0 or 1.

20 Claims, 21 Drawing Sheets

(51) Int. Cl.
| | | |
|---|---|---|
| C09K 11/06 | (2006.01) | |
| H10K 50/11 | (2023.01) | |
| H10K 50/84 | (2023.01) | |
| H10K 50/858 | (2023.01) | |
| H10K 50/842 | (2023.01) | |
| H10K 59/12 | (2023.01) | |
| H10K 59/38 | (2023.01) | |

(52) U.S. Cl.
CPC ...... C09K 2211/1022 (2013.01); H10K 50/11 (2023.02); H10K 50/846 (2023.02); H10K 50/8426 (2023.02); H10K 50/858 (2023.02); H10K 59/12 (2023.02); H10K 59/38 (2023.02); H10K 85/657 (2023.02); H10K 85/6572 (2023.02)

(58) Field of Classification Search
CPC .... H10K 50/11; H10K 50/8426; H10K 59/12; C07D 513/04; C09K 11/06; C09K 2211/1022; H01L 51/0036; H01L 51/0047; C08G 2261/3243; C08G 2261/414; C08G 2261/124; C08G 2261/91

See application file for complete search history.

(56) References Cited

U.S. PATENT DOCUMENTS

| | | | |
|---|---|---|---|
| 9,960,371 B2 | 5/2018 | Yamaguchi et al. | |
| 10,283,722 B2 | 5/2019 | Yamaguchi et al. | |
| 2013/0037785 A1* | 2/2013 | Fujita | H10K 85/631 257/E51.026 |
| 2013/0168654 A1* | 7/2013 | Fujita | H01L 33/504 257/40 |
| 2015/0340519 A1* | 11/2015 | Rachwal | H10K 85/657 438/69 |
| 2018/0261773 A1* | 9/2018 | Yamamoto | H10K 85/631 |
| 2020/0079787 A1* | 3/2020 | Tang | C07D 241/24 |

* cited by examiner

ORGANIC COMPOUND, LIGHT-EMITTING DEVICE, LIGHT-EMITTING APPARATUS, ELECTRONIC DEVICE, AND LIGHTING DEVICE

BACKGROUND OF THE INVENTION

1. Field of the Invention

One embodiment of the present invention relates to an organic compound, a light-emitting device, a light-receiving device, a light-emitting apparatus, an electronic device, and a lighting device. Note that one embodiment of the present invention is not limited to the above technical field. That is, one embodiment of the present invention relates to an object, a method, a manufacturing method, or a driving method. One embodiment of the present invention relates to a process, a machine, manufacture, or a composition of matter. Specific examples include a semiconductor device, a display device, a liquid crystal display device, and the like.

2. Description of the Related Art

A light-emitting device including an EL layer between a pair of electrodes (also referred to as an organic EL device or a light-emitting element) has characteristics such as thinness, light weight, high-speed response to input signals, and low power consumption; thus, a display including such a light-emitting device has attracted attention as a next-generation flat panel display.

In a light-emitting device, voltage application between a pair of electrodes causes, in an EL layer, recombination of electrons and holes injected from the electrodes, which brings a light-emitting substance contained in the EL layer into an excited state. Light is emitted when the light-emitting substance returns to the ground state from the excited state. The excited state can be a singlet excited state (S*) and a triplet excited state (T*). Light emission from a singlet excited state is referred to as fluorescence, and light emission from a triplet excited state is referred to as phosphorescence. The statistical generation ratio in the light-emitting device is considered to be S*:T*=1:3. Since the spectrum of light emitted from a light-emitting substance depends on the light-emitting substance, the use of different kinds of substances as light-emitting substances makes it possible to obtain light-emitting devices which exhibit various colors.

In order to improve device characteristics of such a light-emitting device, improvement of a device structure, development of a material, and the like have been actively carried out (see Patent Document 1, for example).

REFERENCE

Patent Document

[Patent Document 1] Japanese Published Patent Application No. 2017-114853

SUMMARY OF THE INVENTION

Thus, in one embodiment of the present invention, a novel organic compound is provided. Furthermore, one embodiment of the present invention provides a novel organic compound having an emission spectrum peak in a region with wavelengths longer than 850 nm and an absorption spectrum peak in a region with wavelengths longer than 600 nm. One embodiment of the present invention provides a novel organic compound that can be used in a light-emitting device. One embodiment of the present invention provides a novel organic compound that can be used in an EL layer of a light-emitting device. Furthermore, one embodiment of the present invention provides a novel light-emitting device having an emission spectrum peak in a region with wavelengths longer than 850 nm and an absorption spectrum peak in a region with wavelengths longer than 600 nm. A novel light-emitting apparatus, a novel electronic device, or a novel lighting device which uses the light-emitting device of one embodiment of the present invention is provided. Note that the description of these objects does not disturb the existence of other objects. One embodiment of the present invention does not need to achieve all the objects. Other objects will be apparent from and can be derived from the description of the specification, the drawings, the claims, and the like.

One embodiment of the present invention is an organic compound represented by General Formula (G1) below.

[Chemical Formula 1]

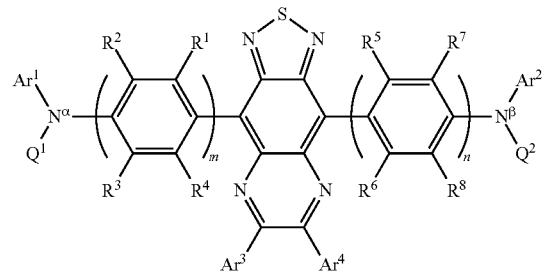

(G1)

In General Formula (G1), $Ar^1$ to $Ar^4$ each independently represent a substituted or unsubstituted aryl group having 6 to 13 carbon atoms in a ring. Furthermore, $R^1$ to $R^8$ each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring. Furthermore, $Q^1$ and $Q^2$ each independently represent a substituted or unsubstituted group having a carbazole skeleton or a substituted or unsubstituted group having a triarylamine skeleton and having 18 to 30 carbon atoms in a ring. Note that three aryl groups in the triarylamine skeleton may have the same structure or different structures. In addition, m and n each independently represent 0 or 1.

Note that $Q^1$ and $Q^2$ in General Formula (G1) are each independently represented by any one of General Formulae (Q-1), (Q-2), and (Q-3).

[Chemical Formulae 2]

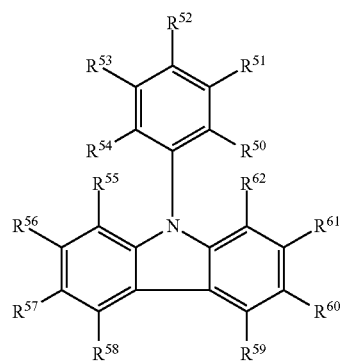

(Q-1)

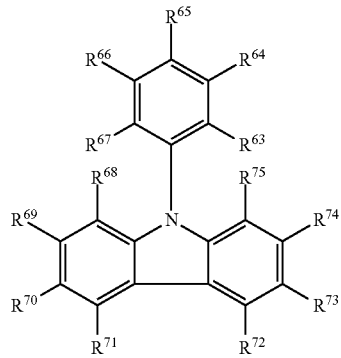

(Q-2)

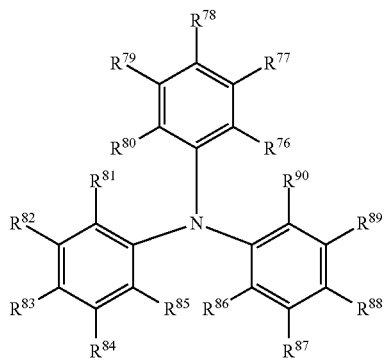

(Q-3)

In General Formula (Q-1), any one of $R^{50}$ to $R^{54}$ is bonded to nitrogen (either $N^\alpha$ or $N^\beta$) in General Formula (G1), and the others each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring.

In General Formula (Q-2), any one of $R^{72}$ to $R^{75}$ is bonded to nitrogen (either $N^\alpha$ or $N^\beta$) in General Formula (G1), and the others each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring.

In General Formula (Q-3), any one of $R^{76}$ to $R^{80}$ is bonded to nitrogen (either $N^\alpha$ or $N^\beta$) in General Formula (G1), and the others each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring. In addition, $R^{55}$ to $R^{62}$, $R^{63}$ to $R^{71}$, and $R^{81}$ to $R^{90}$ each independently represent any one of hydrogen, an alkyl group having 1 to 6 carbon atoms, a substituted or unsubstituted aryl group having 6 to 13 carbon atoms in a ring, a cycloalkyl group having 3 to 6 carbon atoms, and a substituted or unsubstituted heteroaryl group having 3 to 13 carbon atoms in a ring.

Another embodiment of the present invention is an organic compound represented by General Formula (G2) below.

[Chemical Formula 3]

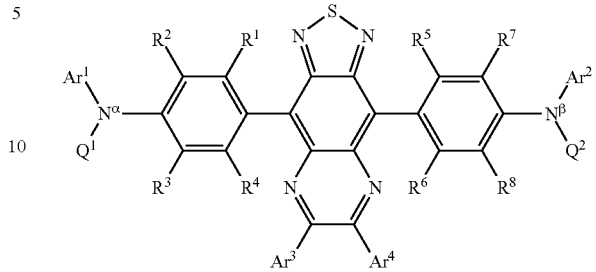

(G2)

In General Formula (G2), $Ar^1$ to $Ar^4$ each independently represent a substituted or unsubstituted aryl group having 6 to 13 carbon atoms in a ring. Furthermore, $R^1$ to $R^8$ each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring. Furthermore, $Q^1$ and $Q^2$ each independently represent a substituted or unsubstituted group having a carbazole skeleton or a substituted or unsubstituted group having a triarylamine skeleton and having 18 to 30 carbon atoms in a ring. Note that three aryl groups in the triarylamine skeleton may have the same structure or different structures.

Note that $Q^1$ and $Q^2$ in General Formula (G2) are each independently represented by any one of General Formulae (Q-1), (Q-2), and (Q-3).

[Chemical Formulae 4]

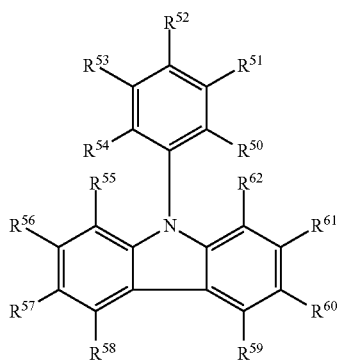

(Q-1)

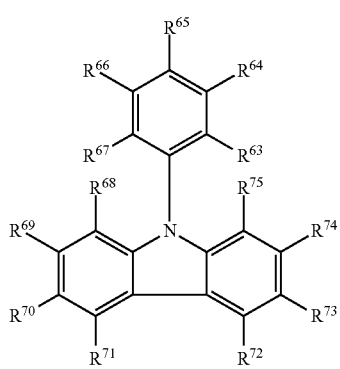

(Q-2)

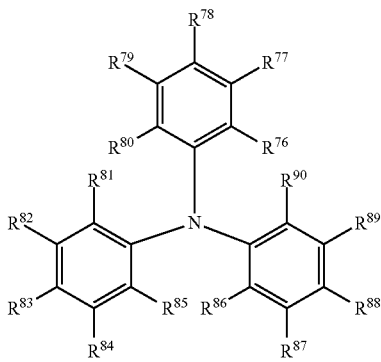

(Q-3)

In General Formula (Q-1), any one of $R^{50}$ to $R^{54}$ is bonded to nitrogen (either $N^\alpha$ or $N^\beta$) in General Formula (G2), and the others each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring.

In General Formula (Q-2), any one of $R^{72}$ to $R^{75}$ is bonded to nitrogen (either $N^\alpha$ or $N^\beta$) in General Formula (G2), and the others each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring.

In General Formula (Q-3), any one of $R^{76}$ to $R^{80}$ is bonded to nitrogen (either $N^\alpha$ or $N^\beta$) in General Formula (G2), and the others each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring. In addition, $R^{55}$ to $R^{62}$, $R^{63}$ to $R^{71}$, and $R^{81}$ to $R^{90}$ each independently represent any one of hydrogen, an alkyl group having 1 to 6 carbon atoms, a substituted or unsubstituted aryl group having 6 to 13 carbon atoms in a ring, a cycloalkyl group having 3 to 6 carbon atoms, and a substituted or unsubstituted heteroaryl group having 3 to 13 carbon atoms in a ring.

Another embodiment of the present invention is an organic compound represented by General Formula (G3) below.

[Chemical Formula 5]

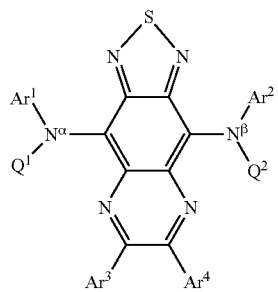

(G3)

In General Formula (G3), $Ar^1$ to $Ar^4$ each independently represent a substituted or unsubstituted aryl group having 6 to 13 carbon atoms in a ring. Furthermore, $Q^1$ and $Q^2$ each independently represent a substituted or unsubstituted group having a carbazole skeleton or a substituted or unsubstituted group having a triarylamine skeleton and having 18 to 30 carbon atoms in a ring. Note that three aryl groups in the triarylamine skeleton may have the same structure or different structures.

Note that $Q^1$ and $Q^2$ in General Formula (G3) are each independently represented by any one of General Formulae (Q-1), (Q-2), and (Q-3).

[Chemical Formulae 6]

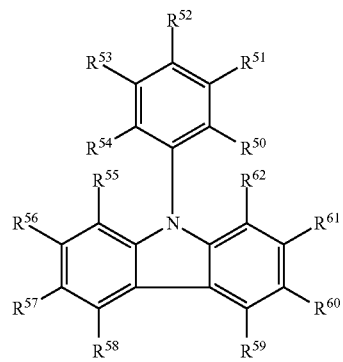

(Q-1)

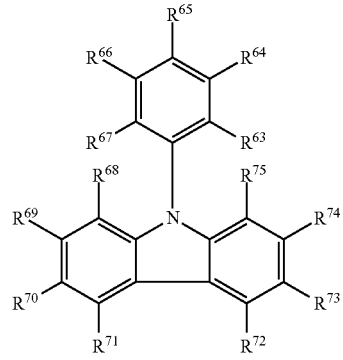

(Q-2)

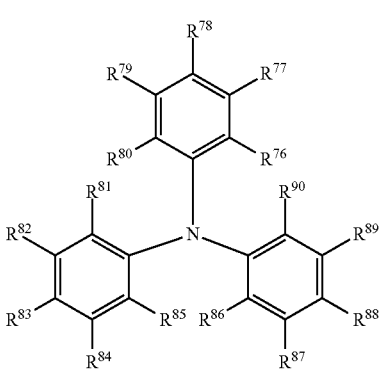

(Q-3)

In General Formula (Q-1), any one of $R^{50}$ to $R^{54}$ is bonded to nitrogen (either $N^\alpha$ or $N^\beta$) in General Formula (G3), and the others each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring.

Furthermore, in General Formula (Q-2), any one of $R^{72}$ to $R^{75}$ is bonded to nitrogen (either $N^\alpha$ or $N^\beta$) in General Formula (G3), and the others each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring.

Furthermore, in General Formula (Q-3), any one of $R^{76}$ to $R^{80}$ is bonded to nitrogen (either $N^\alpha$ or $N^\beta$) in General Formula (G3), and the others each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring. In addition, $R^{55}$ to $R^{62}$, $R^{63}$ to $R^{71}$, and $R^{81}$ to $R^{90}$ each independently represent any one of hydrogen, an alkyl group having 1 to 6 carbon atoms, a substituted or unsubstituted aryl group having 6 to 13 carbon atoms in a ring, a cycloalkyl group having 3 to 6 carbon atoms, and a substituted or unsubstituted heteroaryl group having 3 to 13 carbon atoms in a ring.

Another embodiment of the present invention is an organic compound represented by General Formula (G4) below.

[Chemical Formula 7]

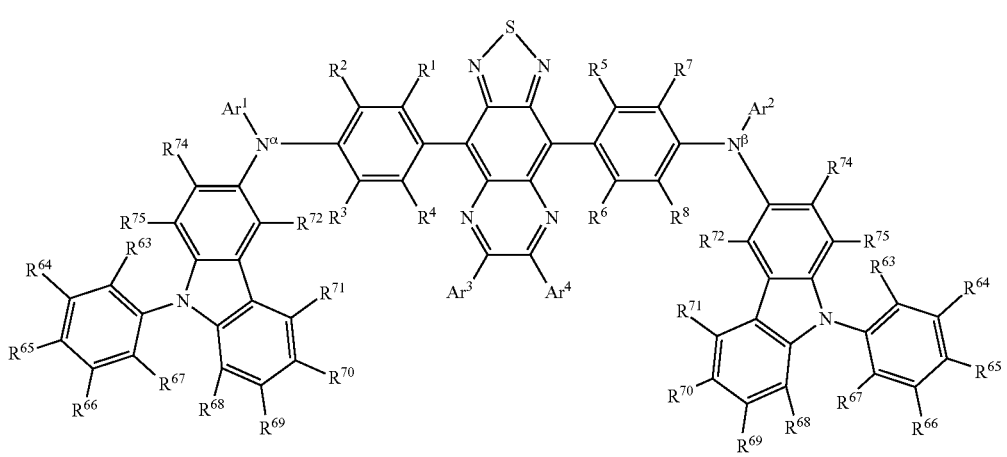

(G4)

In General Formula (G4), $Ar^1$ to $Ar^4$ each independently represent a substituted or unsubstituted aryl group having 6 to 13 carbon atoms in a ring. Furthermore, $R^{63}$ to $R^{72}$ and $R^{74}$ to $R^{75}$ each independently represent any one of hydrogen, an alkyl group having 1 to 6 carbon atoms, a substituted or unsubstituted aryl group having 6 to 13 carbon atoms in a ring, a cycloalkyl group having 3 to 6 carbon atoms, and a substituted or unsubstituted heteroaryl group having 3 to 13 carbon atoms in a ring.

Another embodiment of the present invention is an organic compound represented by General Formula (G5) below.

[Chemical Formula 8]

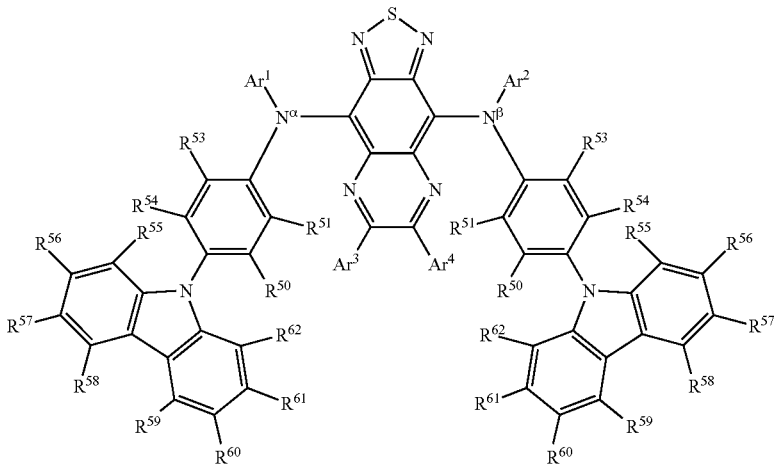

(G5)

In General Formula (G5), $Ar^1$ to $Ar^4$ each independently represent a substituted or unsubstituted aryl group having 6 to 13 carbon atoms in a ring. Furthermore, $R^{50}$ to $R^{51}$ and $R^{53}$ to $R^{62}$ each independently represent any one of hydrogen, an alkyl group having 1 to 6 carbon atoms, a substituted or unsubstituted aryl group having 6 to 13 carbon atoms in a ring, a cycloalkyl group having 3 to 6 carbon atoms, and a substituted or unsubstituted heteroaryl group having 3 to 13 carbon atoms in a ring.

Another embodiment of the present invention is an organic compound represented by General Formula (G6) below.

[Chemical Formula 9]

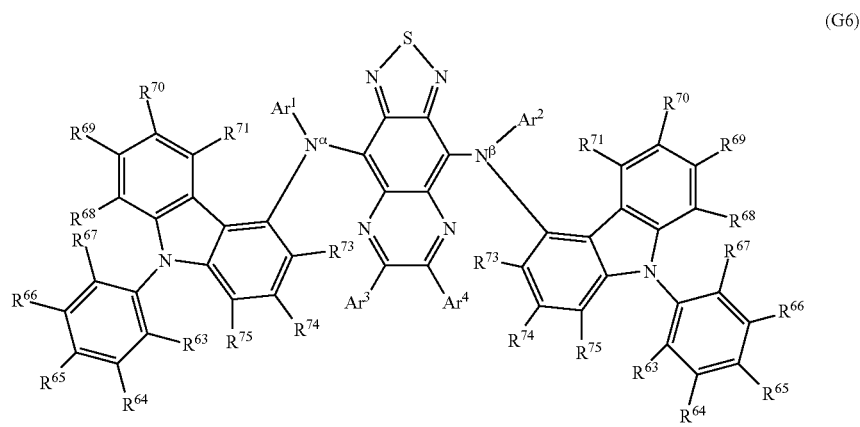

(G6)

In General Formula (G6), $Ar^1$ to $Ar^4$ each independently represent a substituted or unsubstituted aryl group having 6 to 13 carbon atoms in a ring. Furthermore, $R^{63}$ to $R^{71}$ and $R^{73}$ to $R^{75}$ each independently represent any one of hydrogen, an alkyl group having 1 to 6 carbon atoms, a substituted or unsubstituted aryl group having 6 to 13 carbon atoms in a ring, a cycloalkyl group having 3 to 6 carbon atoms, and a substituted or unsubstituted heteroaryl group having 3 to 13 carbon atoms in a ring.

Furthermore, $Ar^1$ to $Ar^4$ in General Formulae (G1) to (G6) are each independently represented by any one of General Formulae (Ar-1), (Ar-2), and (Ar-3).

[Chemical Formulae 10]

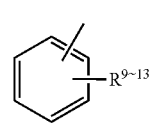

(Ar-1)

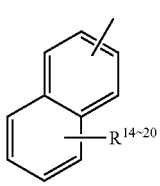

(Ar-2)

-continued

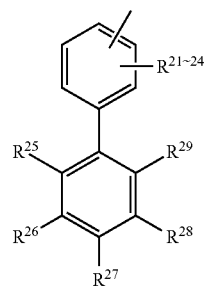

(Ar-3)

In General Formulae (Ar-1), (Ar-2), and (Ar-3), $R^9$ to $R^{29}$ each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring.

Another embodiment of the present invention is represented by any one of Structural Formulae (100), (200), and (300)

[Chemical Formulae 11]

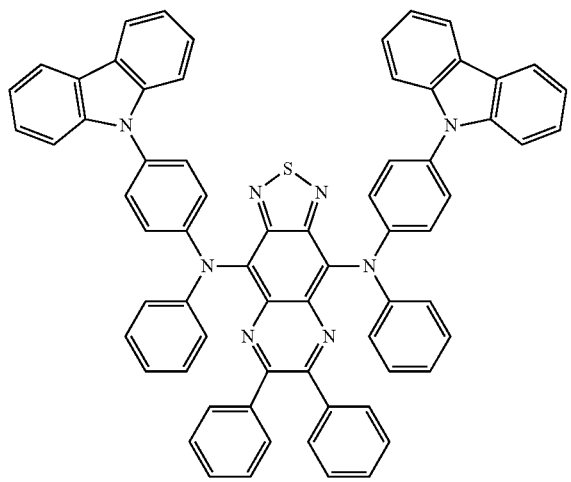
(100)

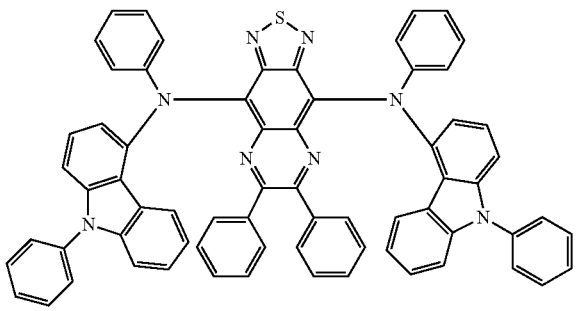
(200)

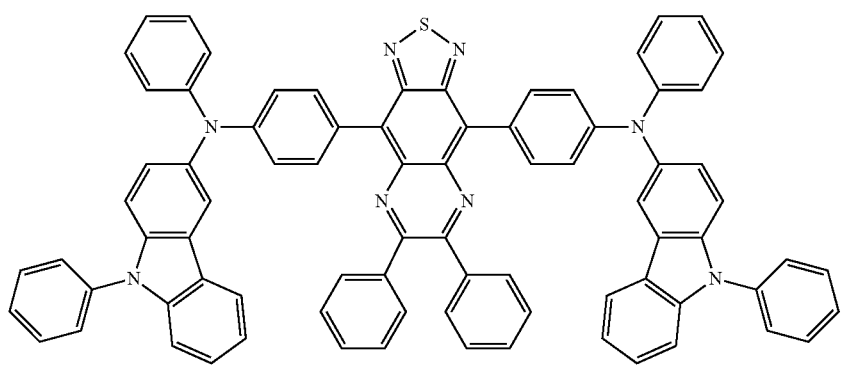
(300)

Another embodiment of the present invention is a light-emitting device using the above-described organic compound of one embodiment of the present invention. Note that one embodiment of the present invention also includes a light-emitting device in which an EL layer provided between a pair of electrodes or a light-emitting layer included in the EL layer contains the organic compound of one embodiment of the present invention. In addition to the light-emitting devices, a light-emitting apparatus including a transistor, a substrate, and the like is also included in the scope of the invention. Furthermore, in addition to the light-emitting apparatus, an electronic device and a lighting device that include a microphone, a camera, an operation button, an external connection portion, a housing, a cover, a support, a speaker, or the like are also included in the scope of the invention.

Note that the present invention also includes a light-emitting device in which an EL layer provided between a pair of electrodes or a light-emitting layer included in the EL layer contains the organic compound of one embodiment of the present invention. In addition to the aforementioned light-emitting device, the present invention includes a light-emitting device including a layer (e.g., a cap layer) that is in contact with an electrode and contains an organic compound. In addition to the light-emitting devices, a light-emitting apparatus including a transistor, a substrate, and the like is also included in the scope of the invention. Furthermore, in addition to the light-emitting apparatus, an electronic device and a lighting device that include a microphone, a camera, an operation button, an external connection portion, a housing, a cover, a support, a speaker, or the like are also included in the scope of the invention.

The organic compound of one embodiment of the present invention can be used in combination with another organic compound (including an organic metal complex) for a light-emitting layer of a light-emitting device. This means that forming a light-emitting layer with a desired structure is highly effective in achieving a highly efficient light-emitting device. Thus, one embodiment of the present invention includes a light-emitting device in which the organic compound of one embodiment of the present invention and one or more kinds of other organic compounds are used in combination in a light-emitting layer.

In addition, the scope of one embodiment of the present invention includes a light-emitting apparatus including a light-emitting device, and a lighting device including the light-emitting apparatus. Accordingly, the light-emitting apparatus in this specification refers to an image display device and a light source (including a lighting device). In addition, the light-emitting apparatus includes the following in its category: a module in which a connector such as a flexible printed circuit (FPC) or a tape carrier package (TCP) is attached to a light-emitting apparatus; a module in which a printed wiring board is provided at the end of a TCP; and a module in which an integrated circuit (IC) is directly mounted on a light-emitting device by a chip on glass (COG) method.

In one embodiment of the present invention, a novel organic compound can be provided. Furthermore, one embodiment of the present invention can provide a novel organic compound having an emission spectrum peak in a region with wavelengths longer than 850 nm and an absorption spectrum peak in a region with wavelengths longer than 600 nm. One embodiment of the present invention can provide a novel organic compound that can be used in a light-emitting device, a light-receiving device, or both a light-emitting device and a light-receiving device in common. One embodiment of the present invention can provide a novel organic compound that can be used in an EL layer of a light-emitting device. Furthermore, one embodiment of the present invention can provide a novel light-emitting device having an emission spectrum peak in a region with wavelengths longer than 850 nm. Furthermore, one embodiment of the present invention can provide a novel light-receiving device having an absorption spectrum peak in a region with wavelengths longer than 600 nm. A novel light-emitting apparatus, a novel electronic device, or a novel lighting device which uses the light-emitting device of one embodiment of the present invention can be provided.

DETAILED DESCRIPTION OF THE INVENTION

Figure 1A:
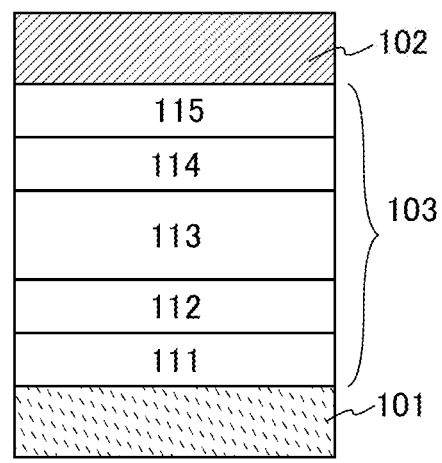
FIGS. 1A and 1B are each a view illustrating a structure of a light-emitting device.

Embodiments of the present invention will be described in detail below with reference to the drawings. Note that the present invention is not limited to the following description, and the modes and details of the present invention can be modified in various ways without departing from the spirit and scope of the present invention. Therefore, the present invention should not be construed as being limited to the description in the following embodiments.

Note that the position, size, range, or the like of each component illustrated in drawings and the like is not accurately represented in some cases for easy understanding. Therefore, the disclosed invention is not necessarily limited to the position, size, range, or the like disclosed in the drawings and the like.

In describing structures of the invention with reference to the drawings in this specification and the like, the same components in different drawings are commonly denoted by the same reference numeral.

Embodiment 1

In this embodiment, organic compounds of embodiments of the present invention will be described. An organic compound of one embodiment of the present invention is represented by General Formula (G1) below. Note that the organic compound of one embodiment of the present invention has a molecular structure including a dithiazoloquinoxaline skeleton and two amine skeletons as shown by General Formula (G1) below.

[Chemical Formula 12]

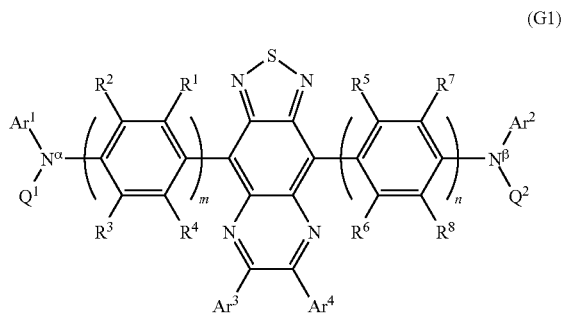

(G1)

In General Formula (G1), $Ar^1$ to $Ar^4$ each independently represent a substituted or unsubstituted aryl group having 6 to 13 carbon atoms in a ring. Furthermore, $R^1$ to $R^8$ each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring. Furthermore, $Q^1$ and $Q^2$ each independently represent a substituted or unsubstituted group having a carbazole skeleton or a substituted or unsubstituted group having a triarylamine skeleton and having 18 to 30 carbon atoms in a ring. Note that three aryl groups in the triarylamine skeleton may have the same structure or different structures. In addition, m and n each independently represent 0 or 1.

Note that $Q^1$ and $Q^2$ in General Formula (G1) are each independently represented by any one of General Formulae (Q-1), (Q-2), and (Q-3).

[Chemical Formulae 13]

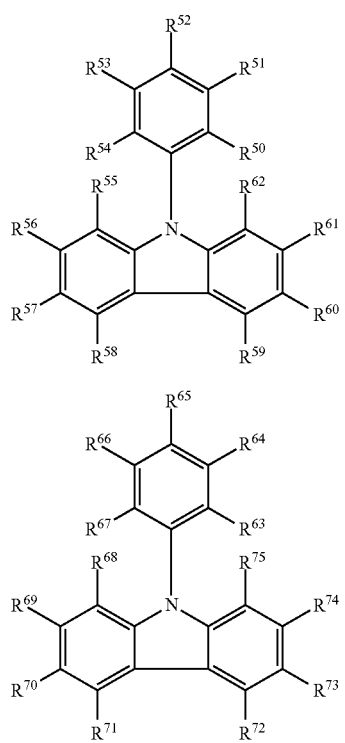

(Q-1)

(Q-2)

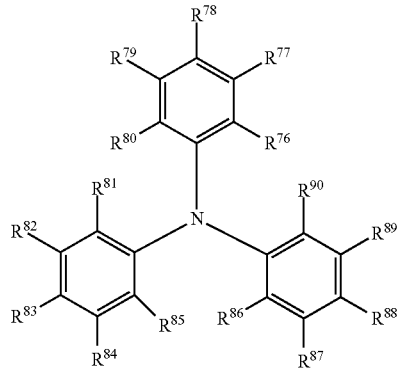

(Q-3)

In General Formula (Q-1), any one of $R^{50}$ to $R^{54}$ is bonded to nitrogen (either $N^\alpha$ or $N^\beta$) in General Formula (G1), and the others each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring.

Furthermore, in General Formula (Q-2), any one of $R^{72}$ to $R^{75}$ is bonded to nitrogen (either $N^\alpha$ or $N^\beta$) in General Formula (G1), and the others each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring.

Furthermore, in General Formula (Q-3), any one of $R^{76}$ to $R^{80}$ is bonded to nitrogen (either $N^\alpha$ or $N^\beta$) in General Formula (G1), and the others each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring. In addition, $R^{55}$ to $R^{62}$, $R^{63}$ to $R^{71}$, and $R^{81}$ to $R^{90}$ each independently represent any one of hydrogen, an alkyl group having 1 to 6 carbon atoms, a substituted or unsubstituted aryl group having 6 to 13 carbon atoms in a ring, a cycloalkyl group having 3 to 6 carbon atoms, and a substituted or unsubstituted heteroaryl group having 3 to 13 carbon atoms in a ring.

The organic compound represented by General Formula (G1) has a deep LUMO level by having a dithiazoloquinoxaline skeleton, and a shallow HOMO level by having two amino groups. In other words, the organic compound represented by General Formula (G1) is a material having a relatively narrow bandgap, and has an emission spectrum peak in a region with wavelengths longer than 850 nm and an absorption spectrum peak in a region with wavelengths longer than 600 nm. Accordingly, the organic compound represented by General Formula (G1) can be favorably used as a light-emitting substance in a light-emitting layer of a light-emitting device (a near-infrared light-emitting device in particular). Furthermore, the organic compound can be favorably used in an active layer of a red-light-receiving device, as well. Moreover, the organic compound represented by General Formula (G1) has a high electron-transport property because of its deep LUMO level derived from a dithiazoloquinoxaline skeleton; thus, the organic compound can be favorably used in a light-emitting device or a light-receiving device. Since the organic compound represented by General Formula (G1) has a shallow HOMO level by having two amino groups and thus has a high hole-transport property, the organic compound can be favorably used in a light-emitting device or a light-receiving device.

Another embodiment of the present invention is an organic compound represented by General Formula (G2) below. Note that the organic compound of one embodiment of the present invention has a molecular structure including a dithiazoloquinoxaline skeleton and two amine skeletons as shown by General Formula (G2) below.

[Chemical Formula 14]

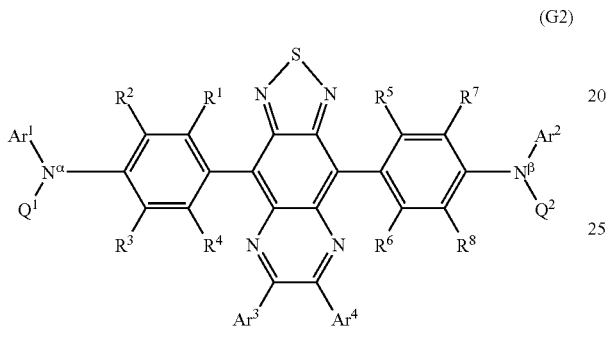

(G2)

In General Formula (G2), $Ar^1$ to $Ar^4$ each independently represent a substituted or unsubstituted aryl group having 6 to 13 carbon atoms in a ring. Furthermore, $R^1$ to $R^8$ each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring. Furthermore, $Q^1$ and $Q^2$ each independently represent a substituted or unsubstituted group having a carbazole skeleton or a substituted or unsubstituted group having a triarylamine skeleton and having 18 to 30 carbon atoms in a ring.

Note that $Q^1$ and $Q^2$ in General Formula (G2) are each independently represented by any one of General Formulae (Q-1), (Q-2), and (Q-3).

[Chemical Formulae 15]

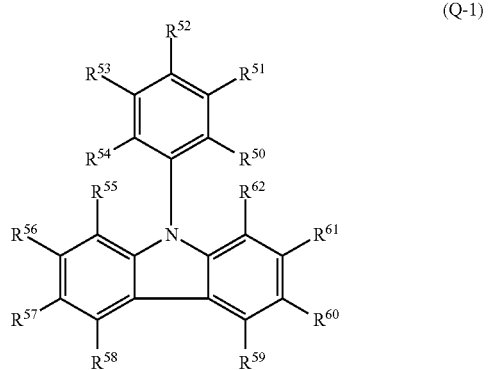

(Q-1)

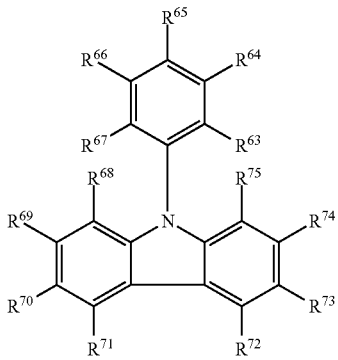

(Q-2)

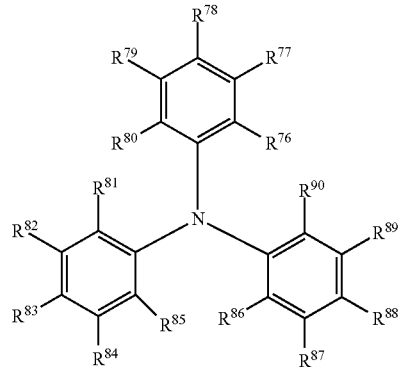

(Q-3)

In General Formula (Q-1), any one of $R^{50}$ to $R^{54}$ is bonded to nitrogen (either $N^\alpha$ or $N^\beta$) in General Formula (G2), and the others each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring.

In General Formula (Q-2), any one of $R^{72}$ to $R^{75}$ is bonded to nitrogen (either $N^\alpha$ or $N^\beta$) in General Formula (G2), and the others each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring.

Furthermore, in General Formula (Q-3), any one of $R^{76}$ to $R^{80}$ is bonded to nitrogen (either $N^\alpha$ or $N^\beta$) in General Formula (G2), and the others each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring. In addition, $R^{55}$ to $R^{62}$, $R^{63}$ to $R^{71}$, and $R^{81}$ to $R^{90}$ each independently represent any one of hydrogen, an alkyl group having 1 to 6 carbon atoms, a substituted or unsubstituted aryl group having 6 to 13 carbon atoms in a ring, a cycloalkyl group having 3 to 6 carbon atoms, and a substituted or unsubstituted heteroaryl group having 3 to 13 carbon atoms in a ring.

The organic compound represented by General Formula (G2) has a molecular structure in which two amine skeletons are each bonded to the dithiazoloquinoxaline skeleton via a phenylene group and thus has a high absorbance for a wavelength region of 600 nm or longer. Accordingly, it is preferable to use the organic compound represented by General Formula (G2) as a light-emitting substance of a light-emitting layer included in an EL layer, in which case energy transfer from a host material can be efficiently performed particularly in a wavelength region of 600 nm or longer. Furthermore, because the organic compound represented by General Formula (G2) has the molecular structure in which two amine skeletons are each bonded to the dithiazoloquinoxaline skeleton via a phenylene group, a shift in the emission wavelength to the longer wavelength side (a shift in the emission spectrum peak to the longer wavelength side), which would occur with the structure in which two amine skeletons are directly bonded to the dithiazoloquinoxaline skeleton, can be avoided. Thus, the emission wavelength can be controlled (slightly to the shorter wavelength side) so that light emission in a desired wavelength region can be obtained.

Another embodiment of the present invention is an organic compound represented by General Formula (G3) below. Note that the organic compound of one embodiment of the present invention has a molecular structure including a dithiazoloquinoxaline skeleton and two amine skeletons as shown by General Formula (G3) below.

[Chemical Formula 16]

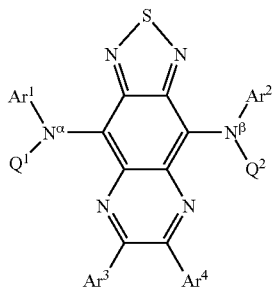

(G3)

In General Formula (G3), $Ar^1$ to $Ar^4$ each independently represent a substituted or unsubstituted aryl group having 6 to 13 carbon atoms in a ring. Furthermore, $Q^1$ and $Q^2$ each independently represent a substituted or unsubstituted group having a carbazole skeleton or a substituted or unsubstituted group having a triarylamine skeleton and having 18 to 30 carbon atoms in a ring.

Note that $Q^1$ and $Q^2$ in General Formula (G3) are each independently represented by any one of General Formulae (Q-1), (Q-2), and (Q-3).

[Chemical Formulae 17]

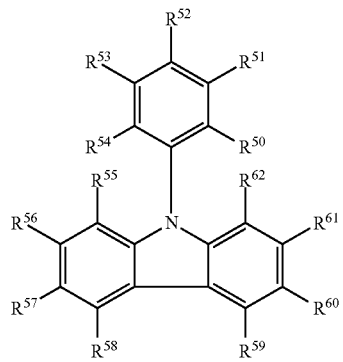

(Q-1)

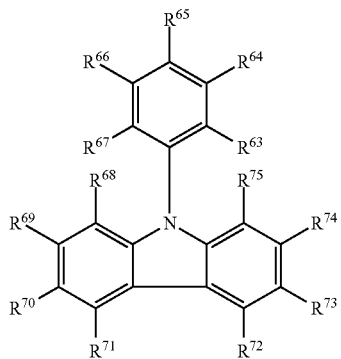

(Q-2)

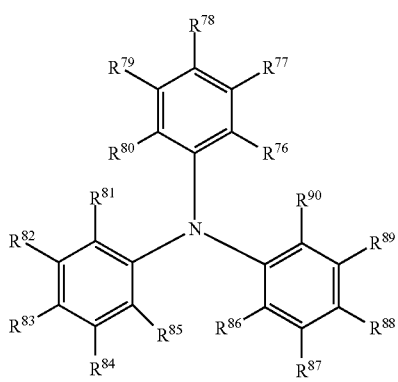

(Q-3)

In General Formula (Q-1), any one of $R^{50}$ to $R^{54}$ is bonded to nitrogen (either $N^\alpha$ or $N^\beta$) in General Formula (G3), and the others each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring.

Furthermore, in General Formula (Q-2), any one of $R^{72}$ to $R^{75}$ is bonded to nitrogen (either $N^\alpha$ or $N^\beta$) in General Formula (G3), and the others each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring.

Furthermore, in General Formula (Q-3), any one of $R^{76}$ to $R^{80}$ is bonded to nitrogen (either $N^\alpha$ or $N^\beta$) in General Formula (G3), and the others each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring. In addition, $R^{55}$ to $R^{62}$, $R^{63}$ to $R^{71}$, and $R^{81}$ to $R^{90}$ each independently represent any one of hydrogen, an alkyl group having 1 to 6 carbon atoms, a substituted or unsubstituted aryl group having 6 to 13 carbon atoms in a ring, a cycloalkyl group having 3 to 6 carbon atoms, and a substituted or unsubstituted heteroaryl group having 3 to 13 carbon atoms in a ring.

The organic compound represented by General Formula (G3) has a molecular structure in which the dithiazoloquinoxaline skeleton and two amine skeletons are directly bonded to each other and thus has a high absorbance for a wavelength region of 600 nm or longer, especially a wavelength region of 700 nm or longer. Accordingly, it is preferable to use the organic compound represented by General Formula (G3) as a light-emitting substance of a light-emitting layer included in an EL layer, in which case energy transfer from a host material can be efficiently performed particularly in a wavelength region of 700 nm or longer. Furthermore, because the organic compound represented by General Formula (G3) has the molecular structure in which two amine skeletons are each directly bonded to the dithiazoloquinoxaline skeleton, an emission peak is positioned in an extremely long wavelength region in the emission spectrum. Having the molecular structure in which two amine skeletons are each directly bonded to the dithiazoloquinoxaline skeleton without through a phenylene group unlike the organic compound represented by General Formula (G2), the organic compound represented by General Formula (G3) sublimates at a relatively low temperature, that is, has an excellent sublimation property.

Another embodiment of the present invention is an organic compound represented by General Formula (G4) below. Note that the organic compound of one embodiment of the present invention has a molecular structure including a dithiazoloquinoxaline skeleton and two amine skeletons as shown by General Formula (G4) below.

In General Formula (G4), $Ar^1$ to $Ar^4$ each independently represent a substituted or unsubstituted aryl group having 6 to 13 carbon atoms in a ring. Furthermore, $R^{63}$ to $R^{72}$ and $R^{74}$ to $R^{75}$ each independently represent any one of hydrogen, an alkyl group having 1 to 6 carbon atoms, a substituted or unsubstituted aryl group having 6 to 13 carbon atoms in a ring, a cycloalkyl group having 3 to 6 carbon atoms, and a substituted or unsubstituted heteroaryl group having 3 to 13 carbon atoms in a ring.

The organic compound represented by General Formula (G4) has a structure in which two amine skeletons are each bonded to the dithiazoloquinoxaline skeleton via a phenylene group and each of the 3-positions of carbazole skeletons is bonded to the amino group. Thus the organic compound represented by General Formula (G4) has a shallow HOMO level and a high absorbance for a wavelength region of 600 nm or longer. Accordingly, it is preferable to use the organic compound represented by General Formula (G4) as a light-emitting substance of a light-emitting layer included in an EL layer, in which case energy transfer from a host material can be efficiently performed particularly in a wavelength region of 600 nm or longer. Furthermore, because the organic compound represented by General Formula (G4) has the molecular structure in which two amine skeletons are each bonded to the dithiazoloquinoxaline skeleton via a phenylene group, a shift in the emission wavelength to the longer wavelength side (a shift in the emission spectrum peak to the longer wavelength side), which would occur with the structure in which two amine skeletons are directly bonded to the dithiazoloquinoxaline skeleton, can be avoided. Thus, the emission wavelength can be controlled (slightly to the shorter wavelength side) so that light emission in a desired wavelength region can be obtained.

Another embodiment of the present invention is an organic compound represented by General Formula (G5) below. Note that the organic compound of one embodiment of the present invention has a molecular structure including a dithiazoloquinoxaline skeleton and two amine skeletons as shown by General Formula (G5) below.

[Chemical Formula 18]

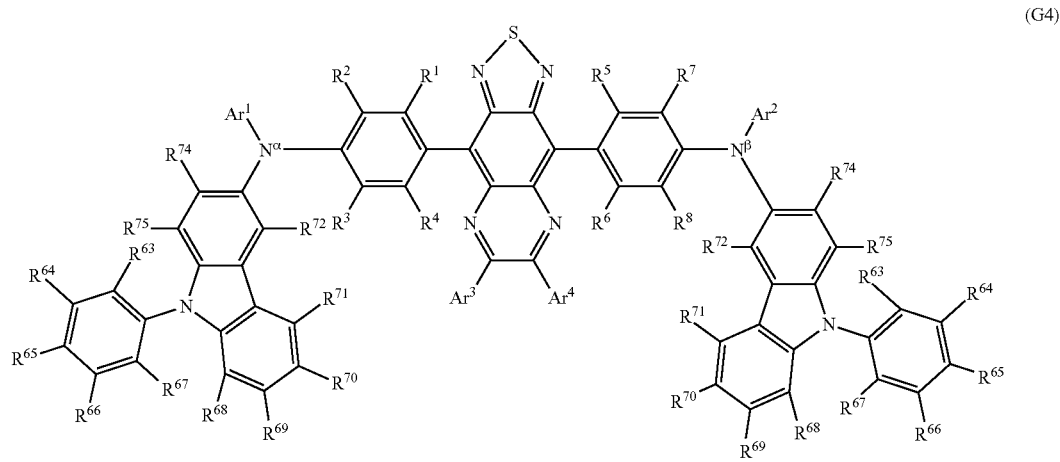

(G4)

[Chemical Formula 19]

(G5)

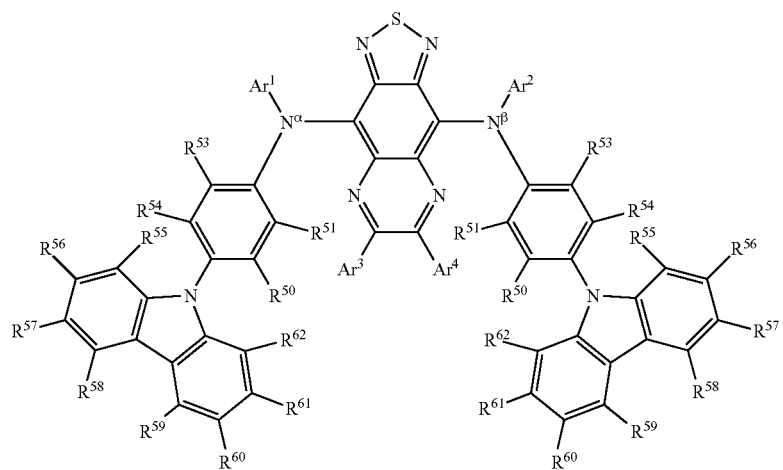

In General Formula (G5), $Ar^1$ to $Ar^4$ each independently represent a substituted or unsubstituted aryl group having 6 to 13 carbon atoms in a ring. Furthermore, $R^{50}$ to $R^{51}$ and $R^{53}$ to $R^{62}$ each independently represent any one of hydrogen, an alkyl group having 1 to 6 carbon atoms, a substituted or unsubstituted aryl group having 6 to 13 carbon atoms in a ring, a cycloalkyl group having 3 to 6 carbon atoms, and a substituted or unsubstituted heteroaryl group having 3 to 13 carbon atoms in a ring.

The organic compound represented by General Formula (G5) has a molecular structure in which the dithiazoloquinoxaline skeleton and two amine skeletons are directly bonded to each other and thus has a high absorbance for a wavelength region of 600 nm or longer, especially a wavelength region of 700 nm or longer. Accordingly, it is preferable to use the organic compound represented by General Formula (G5) as a light-emitting substance of a light-emitting layer included in an EL layer, in which case energy transfer from a host material can be efficiently performed particularly in a wavelength region of 700 nm or longer. Furthermore, because the organic compound represented by General Formula (G5) has the molecular structure in which two amine skeletons are each directly bonded to the dithiazoloquinoxaline skeleton and the 9-position of carbazole is bonded to an aminophenyl group, the effect of carbazole's electron-donating property can be suppressed and the HOMO level can be prevented from becoming excessively shallow. Accordingly, the organic compound represented by General Formula (G5) has an emission spectrum peak in the near-infrared region. Having the molecular structure in which two amine skeletons are each directly bonded to the dithiazoloquinoxaline skeleton without through a phenylene group unlike the organic compound represented by General Formula (G4), the organic compound represented by General Formula (G5) sublimates at a relatively low temperature, that is, has an excellent sublimation property.

Another embodiment of the present invention is an organic compound represented by General Formula (G6) below. Note that the organic compound of one embodiment of the present invention has a molecular structure including a dithiazoloquinoxaline skeleton and two amine skeletons as shown by General Formula (G6) below.

[Chemical Formula 20]

(G6)

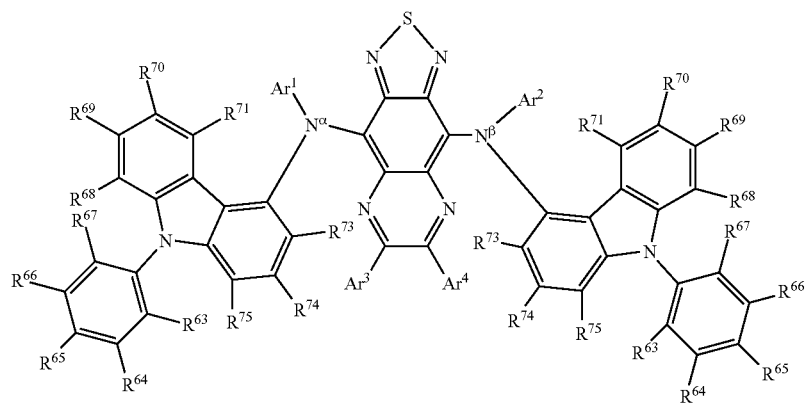

The organic compound represented by General Formula (G6) has a molecular structure in which the dithiazoloquinoxaline skeleton and two amine skeletons are directly bonded to each other and thus has a high absorbance for a wavelength region of 600 nm or longer, especially a wavelength region of 700 nm or longer. Accordingly, it is preferable to use the organic compound represented by General Formula (G6) as a light-emitting substance of a light-emitting layer included in an EL layer, in which case energy transfer from a host material can be efficiently performed particularly in a wavelength region of 700 nm or longer. Furthermore, because the organic compound represented by General Formula (G6) has the molecular structure in which two amine skeletons are each directly bonded to the dithiazoloquinoxaline skeleton and the 4-position of carbazole is bonded to an amino group, the effect of carbazole's electron-donating property can be suppressed and the HOMO level can be prevented from becoming excessively shallow. Accordingly, the organic compound represented by General Formula (G6) has an emission spectrum peak in the near-infrared region.

In General Formula (G6), $Ar^1$ to $Ar^4$ each independently represent a substituted or unsubstituted aryl group having 6 to 13 carbon atoms in a ring. Furthermore, $R^{63}$ to $R^{71}$ and $R^{73}$ to $R^{75}$ each independently represent any one of hydrogen, an alkyl group having 1 to 6 carbon atoms, a substituted or unsubstituted aryl group having 6 to 13 carbon atoms in a ring, a cycloalkyl group having 3 to 6 carbon atoms, and a substituted or unsubstituted heteroaryl group having 3 to 13 carbon atoms in a ring.

Note that $Ar^1$ to $Ar^4$ in General Formulae (G1) to (G6) are each independently represented by any one of General Formulae (Ar-1), (Ar-2), and (Ar-3).

[Chemical Formulae 21]

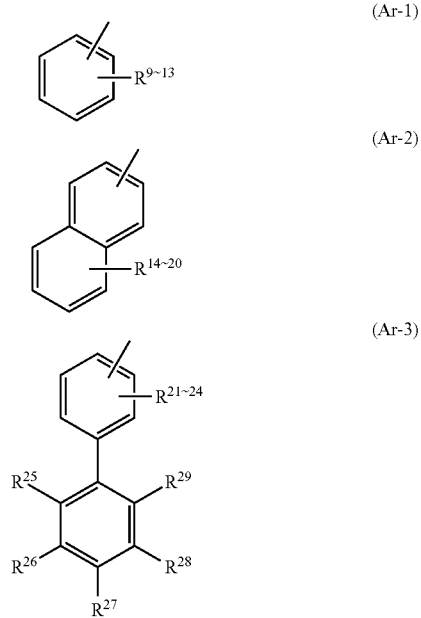

In General Formulae (Ar-1), (Ar-2), and (Ar-3), $R^9$ to $R^{29}$ each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring.

In the case where the substituted or unsubstituted aryl group having 6 to 13 carbon atoms in a ring or the substituted or unsubstituted heteroaryl group having 3 to 13 carbon atoms in a ring in any of General Formulae (G1) to (G6) and (Q-1) to (Q-3) has a substituent, the substituent can be an alkyl group having 1 to 6 carbon atoms, an alkoxy group having 1 to 6 carbon atoms, a cycloalkyl group having 3 to 7 carbon atoms, a polycyclic cycloalkyl group having 7 to 10 carbon atoms, or a cyano group, for example. Specifically, a methyl group, an ethyl group, a propyl group, an isopropyl group, a butyl group, an isobutyl group, a sec-butyl group, a tert-butyl group, a pentyl group, a methoxy group, an ethoxy group, a propoxy group, a cyclopentyl group, a cyclohexyl group, a cycloheptyl group, a 8,9,10-trinorbornanyl group, an adamantyl group, a phenyl group, an o-tolyl group, a m-tolyl group, a p-tolyl group, a mesityl group, an o-biphenyl group, a m-biphenyl group, a p-biphenyl group, a 1-naphthyl group, a 2-naphthyl group, a 9H-fluorenyl group, a 9,9-dimethyl-9H-fluorenyl group, a 9,9-diphenyl-9H-fluorenyl group, an o-pyridyl group, a m-pyridyl group, a p-pyridyl group, a diphenyltriazinyl, or the like can be used.

Specific examples of the alkyl group having 1 to 6 carbon atoms that can serve as $R^1$ to $R^{29}$ and $R^{50}$ to $R^{90}$ in General Formulae (G1) to (G6) and (Q-1) to (Q-3) include a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a 3-methylpentyl group, a 2-methylpentyl group, a 2-ethylbutyl group, a 1,2-dimethylbutyl group, and a 2,3-dimethylbutyl group.

Specific examples of the cycloalkyl group having 3 to 7 carbon atoms that can serve as $R^1$ to $R^{29}$ and $R^{50}$ to $R^{90}$ in General Formulae (G1) to (G6) and (Q-1) to (Q-3) include a cyclopropyl group, a cyclobutyl group, a cyclopentyl group, a cyclohexyl group, and a 1-methylcyclohexyl group.

Furthermore, specific examples of the aryl group having 6 to 13 carbon atoms that can serve as $R^1$ to $R^{29}$ and $R^{50}$ to $R^{90}$ in General Formulae (G1) to (G6) and (Q-1) to (Q-3) include a phenyl group, an o-tolyl group, a m-tolyl group, a p-tolyl group, a mesityl group, an o-biphenyl group, a m-biphenyl group, a p-biphenyl group, a 1-naphthyl group, a 2-naphthyl group, a 9H-fluorenyl group, a 9,9-dimethyl-9H-fluorenyl group, and a 9,9-diphenyl-9H-fluorenyl group.

Furthermore, specific examples of the heteroaryl group having 6 to 13 carbon atoms that can serve as $R^1$ to $R^{29}$ and $R^{50}$ to $R^{90}$ in General Formulae (G1) to (G6) and (Q-1) to (Q-3) include an o-pyridyl group, a m-pyridyl group, a p-pyridyl group, and a diphenyltriazinyl.

Next, specific structural formulae of the aforementioned organic compound of one embodiment of the present invention are shown below. Note that the present invention is not limited to these formulae.

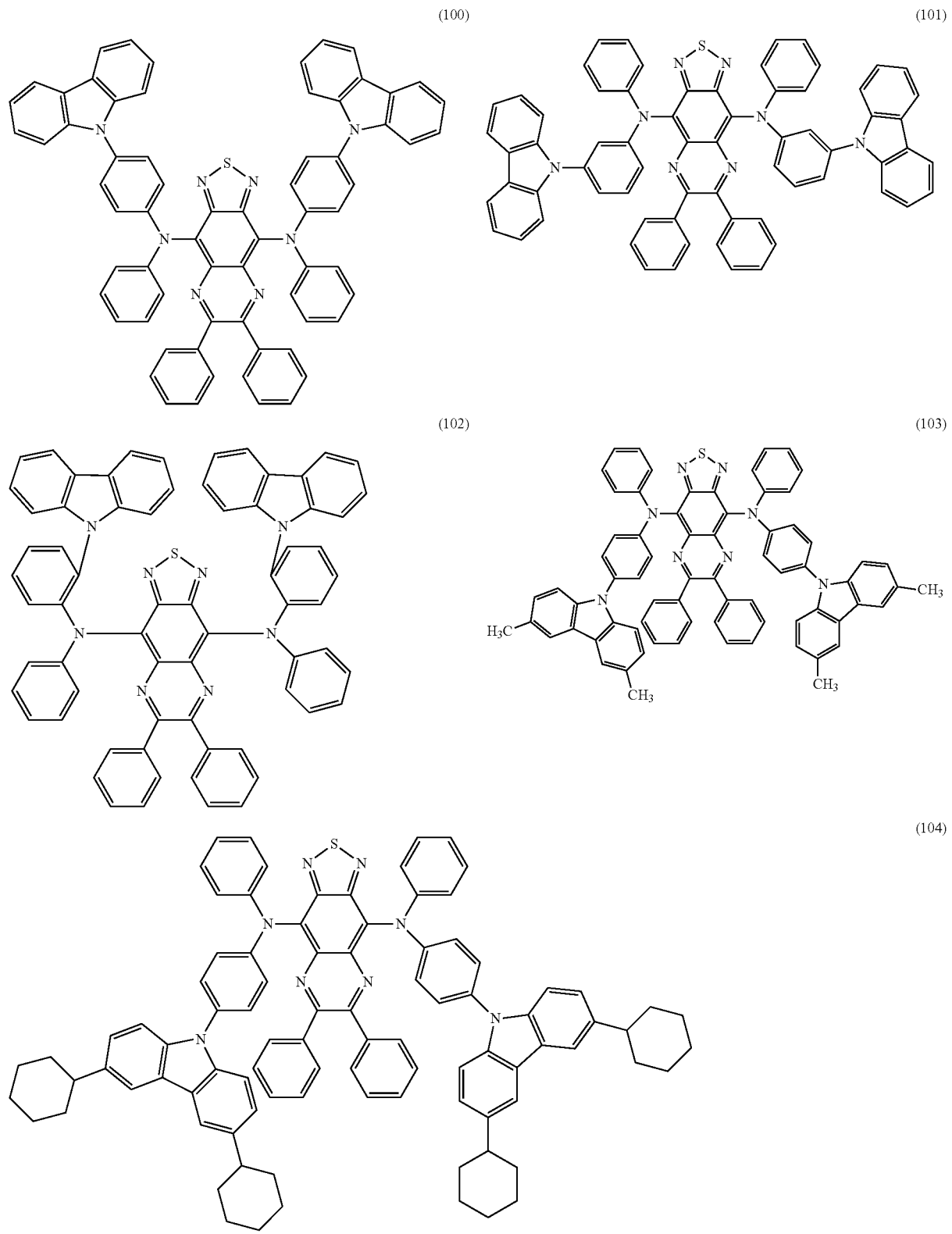

-continued
(105)
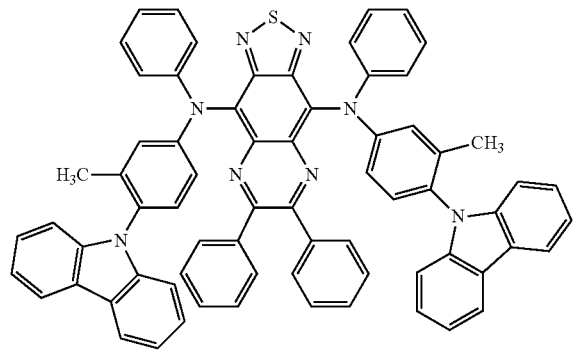
(106)
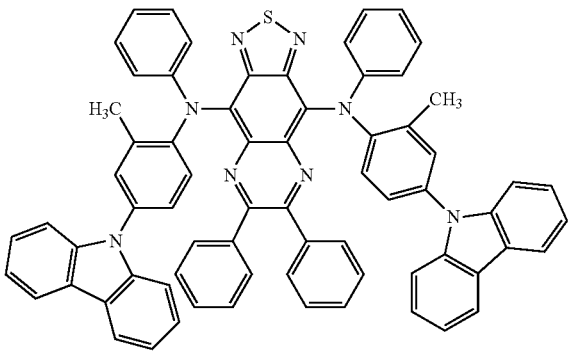
[Chemical Formulae 23]
(107)
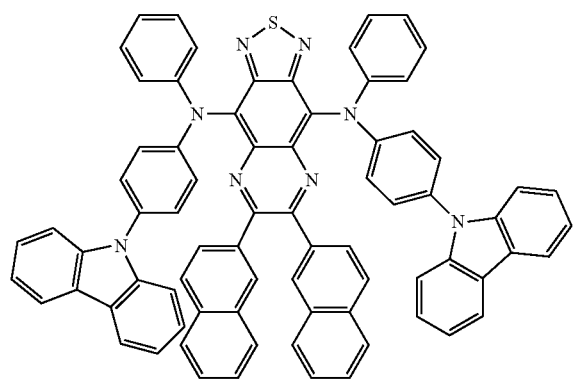
(108)
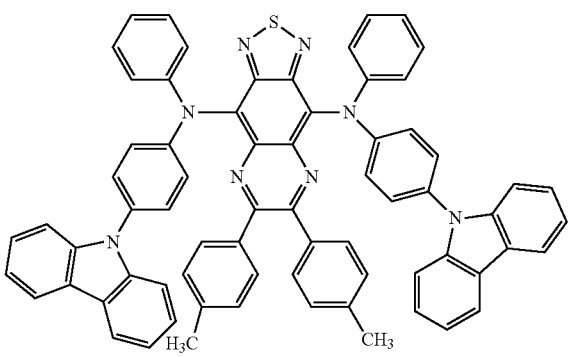
(109)
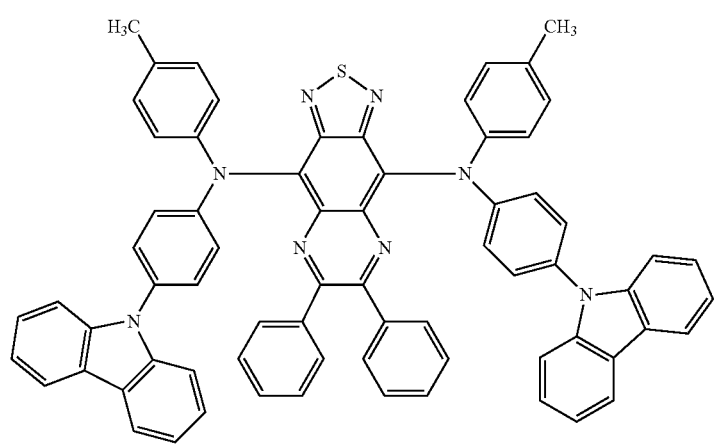
(110)
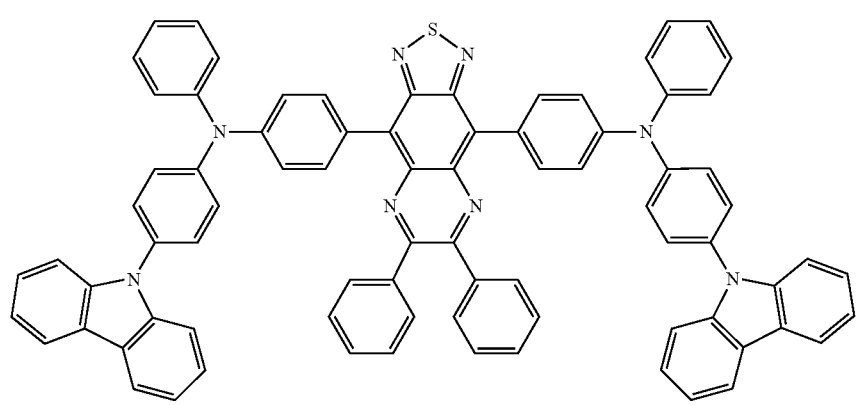

-continued
(111)
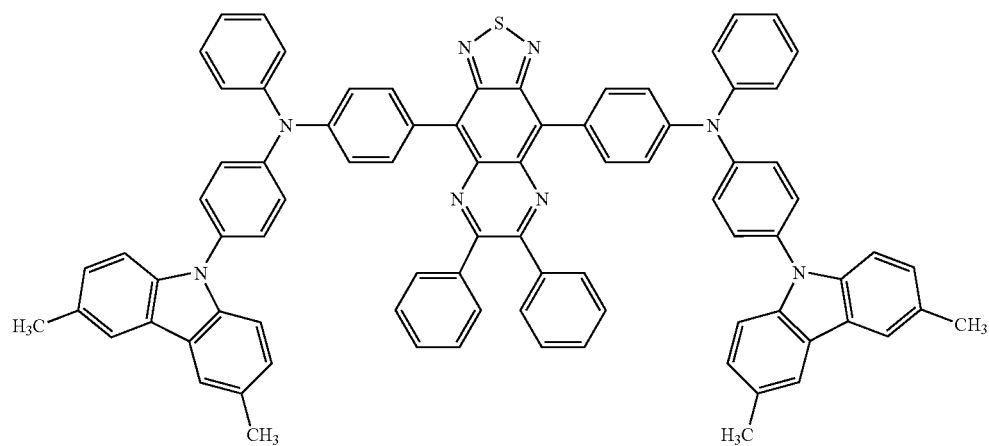
(112)
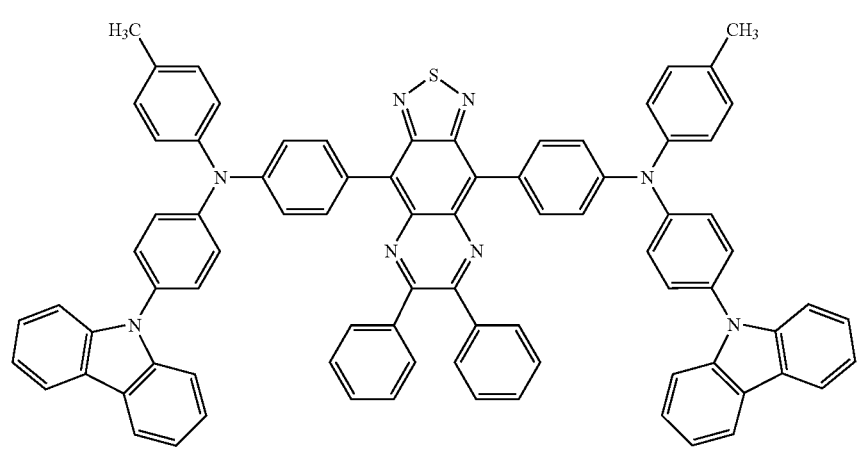
[Chemical Formulae 24]
(200)
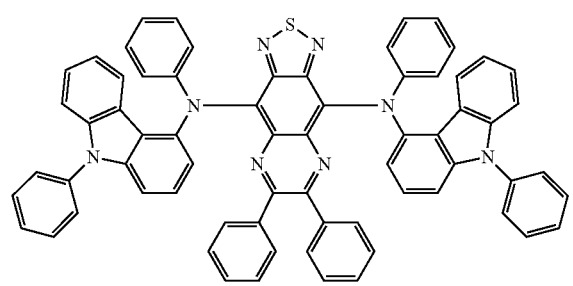
(201)
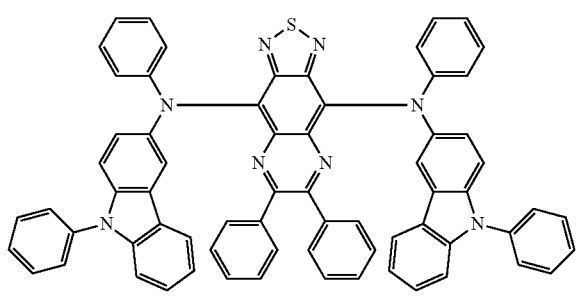
(202)
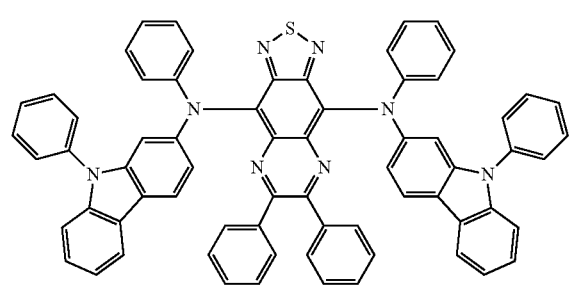
(203)
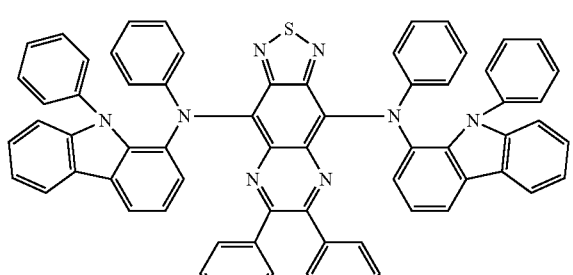

-continued
(204)
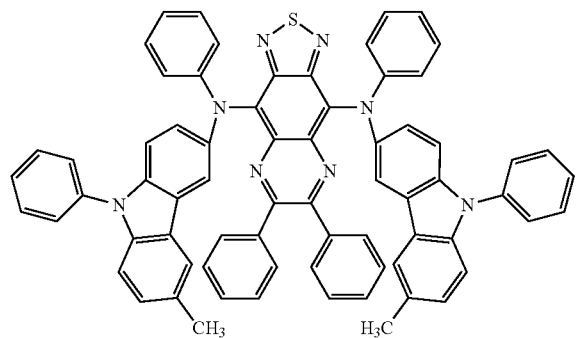
(205)
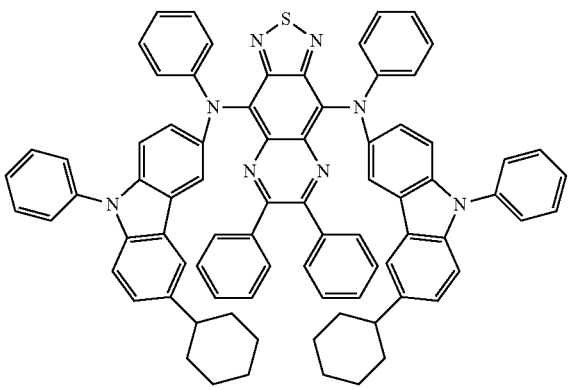
(206)
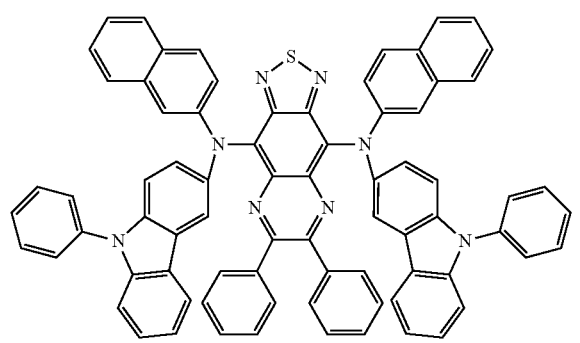
(207)
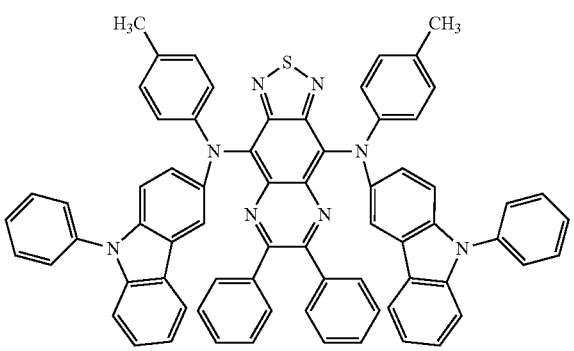
[Chemical Formulae 25]
(208)
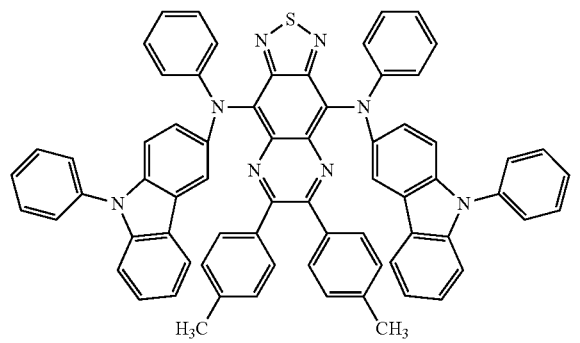
(209)
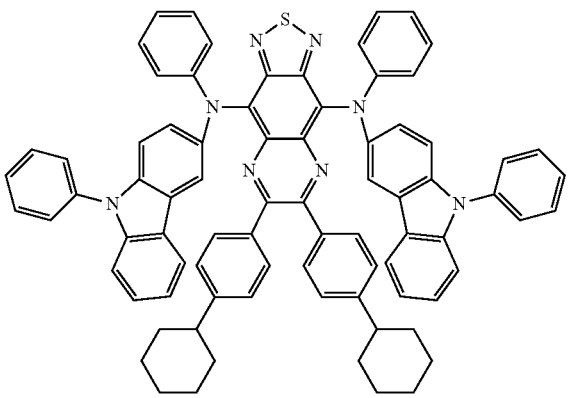
(210)
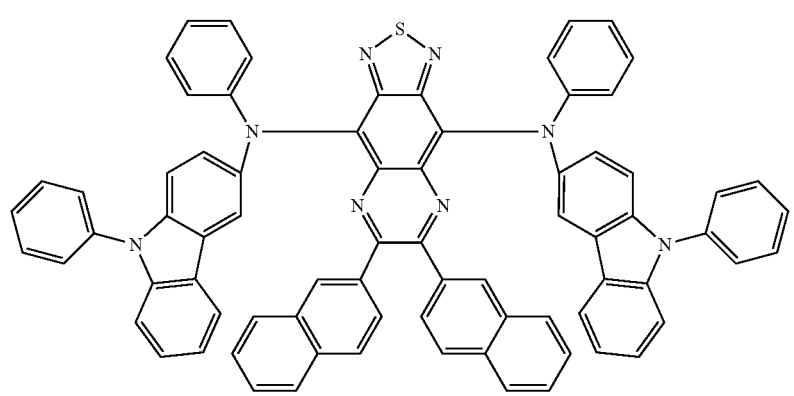

-continued
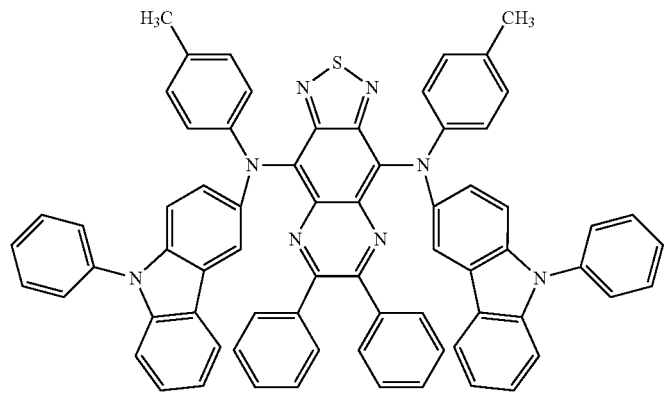
(211)
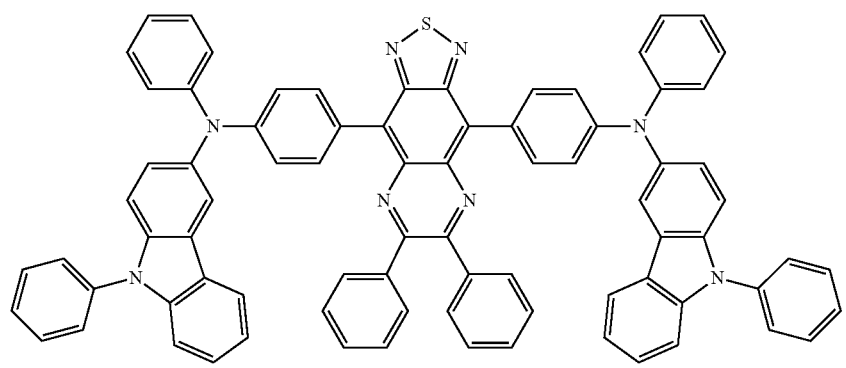
(300)
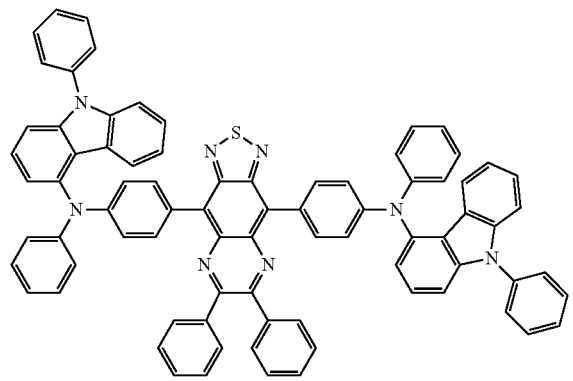
(301)
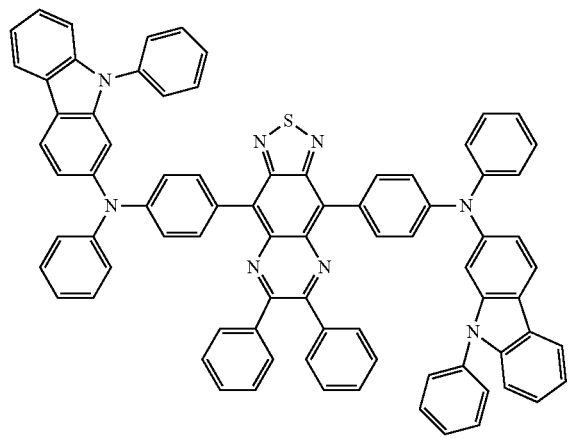
(302)
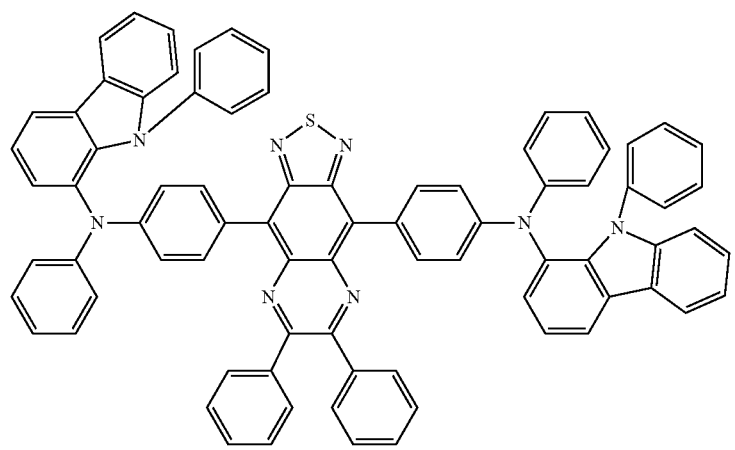
(303)

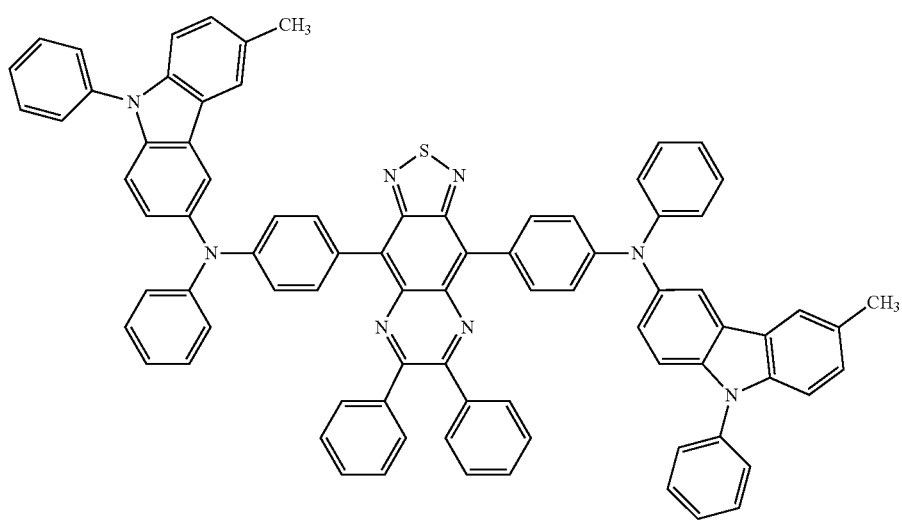
(304)
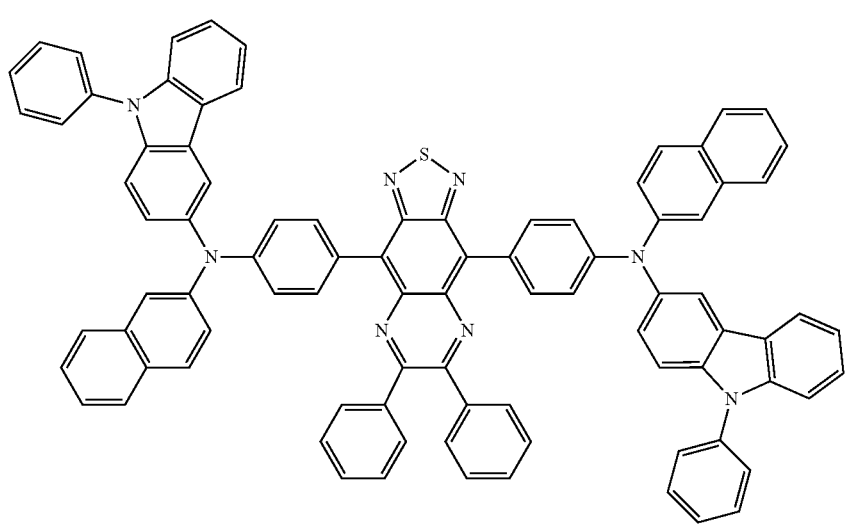
(305)
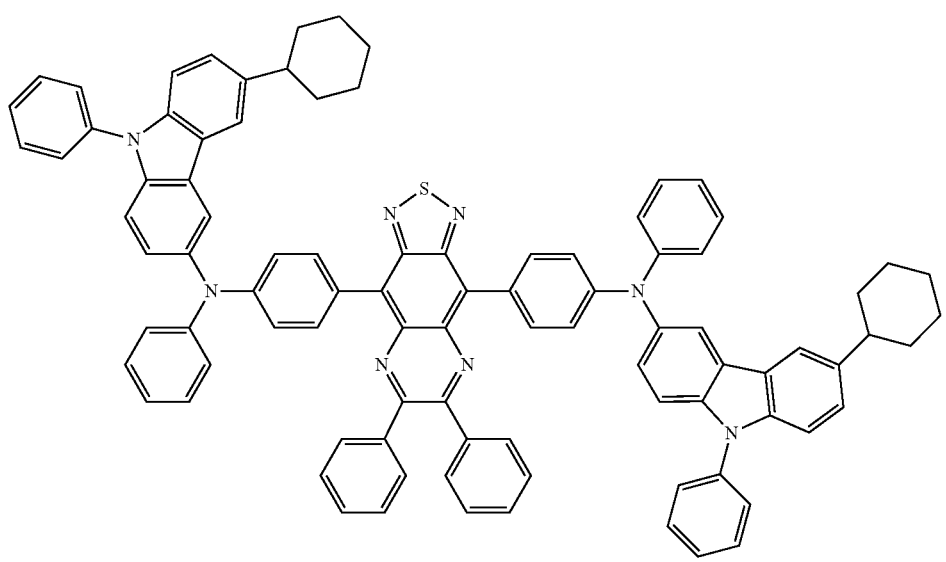
(306)

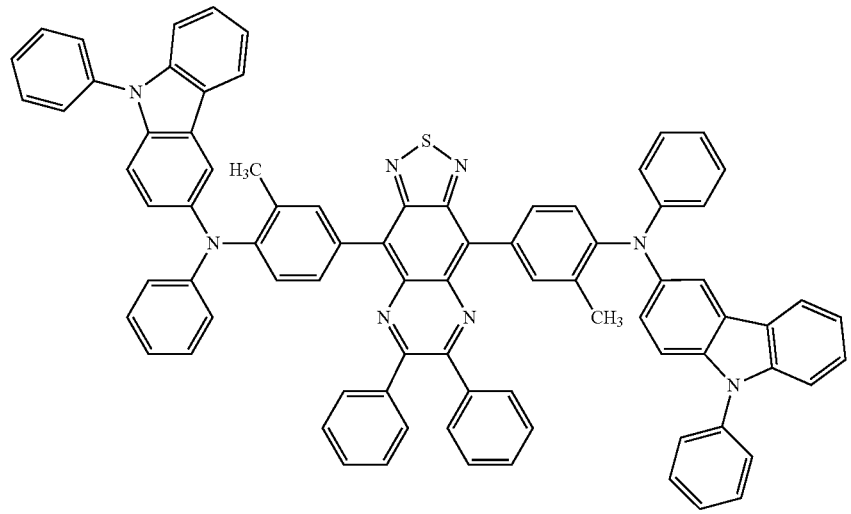
(307)
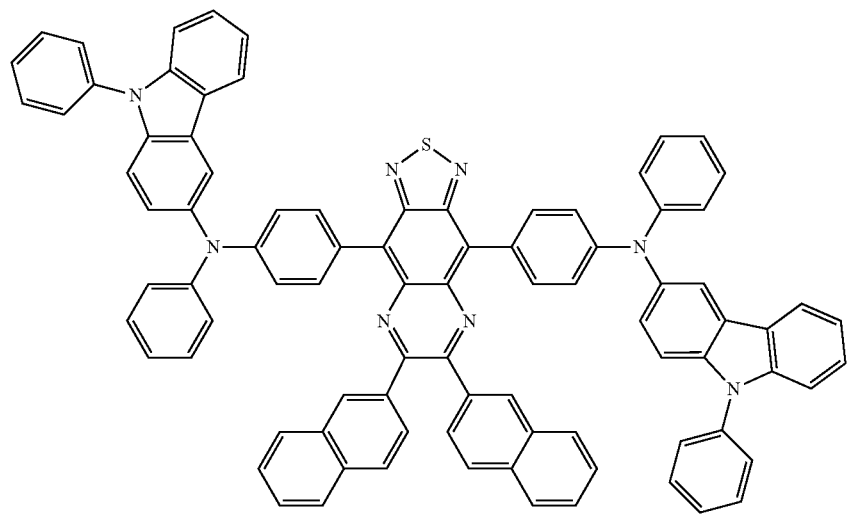
(308)
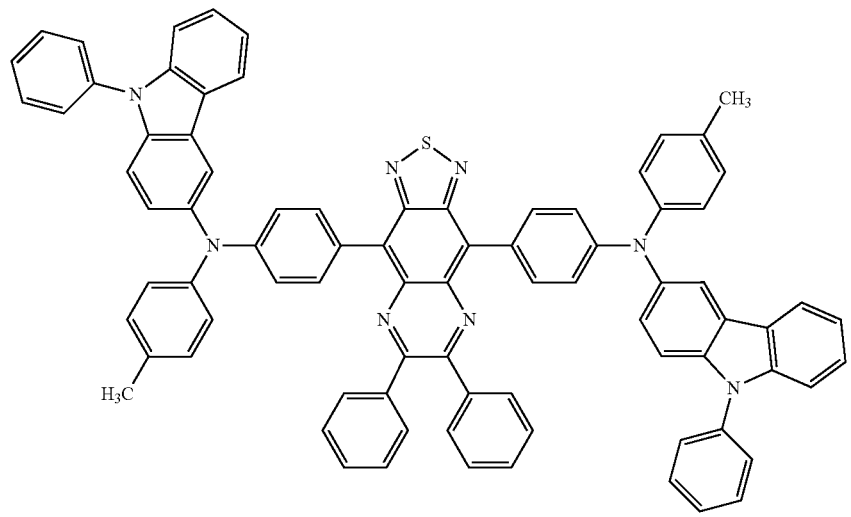
(309)

[Chemical Formulae 27]
(400)
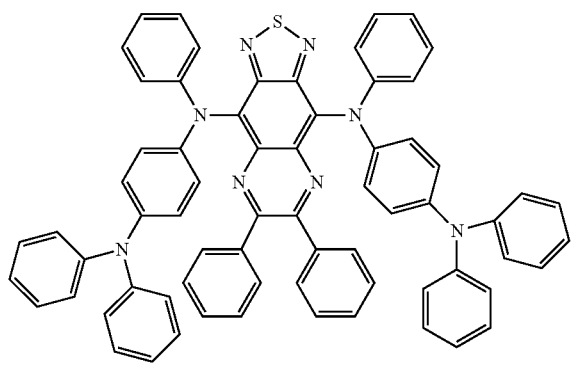
(401)
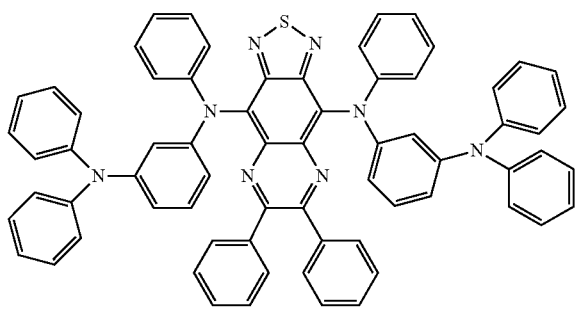
(402)
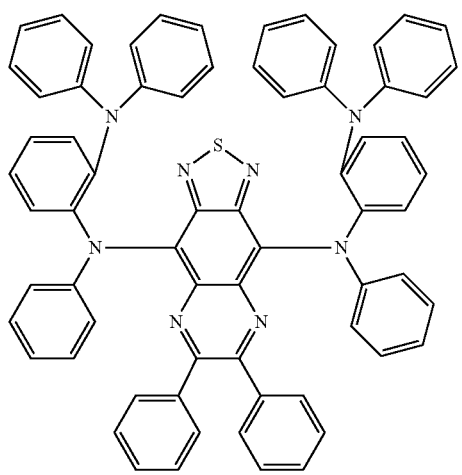
(403)
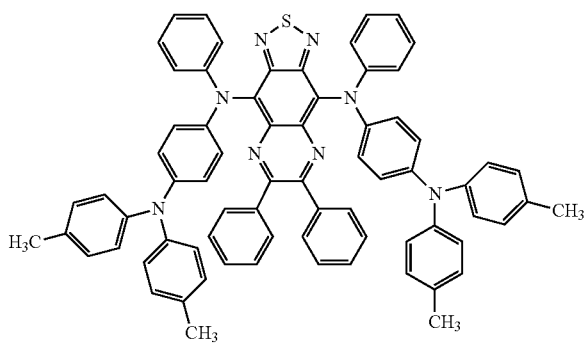
(404)
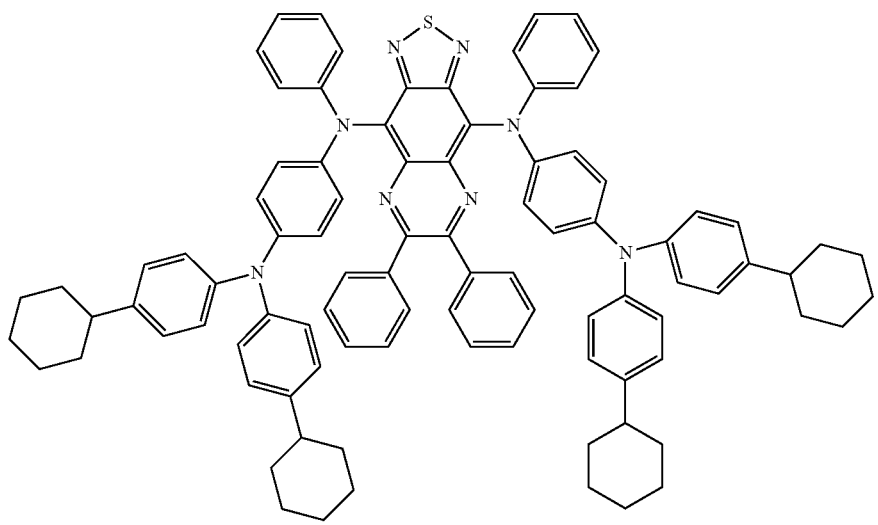

(405)
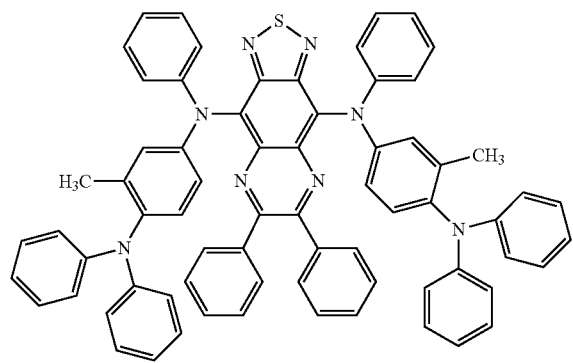
(406)
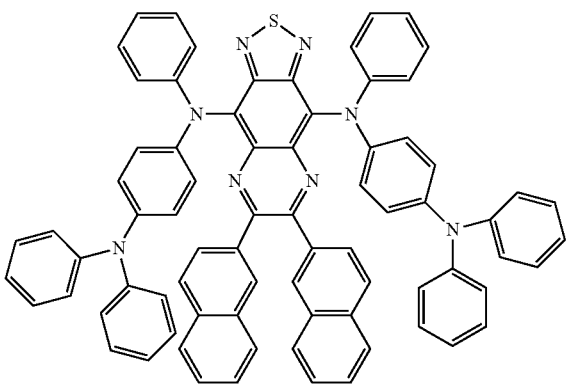
(407)
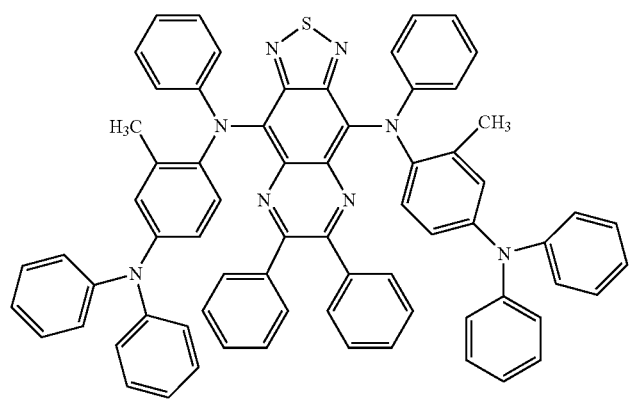
[Chemical Formulae 28]
(408)
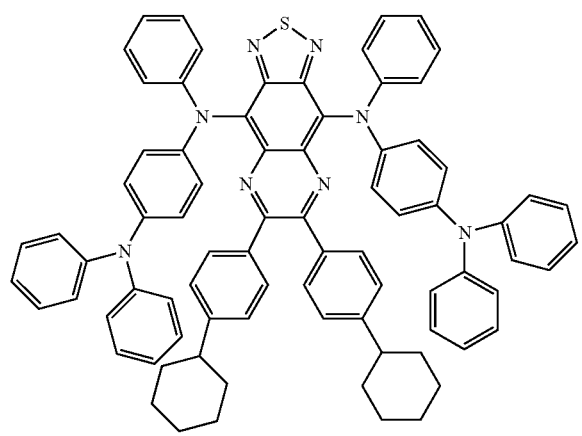
(409)
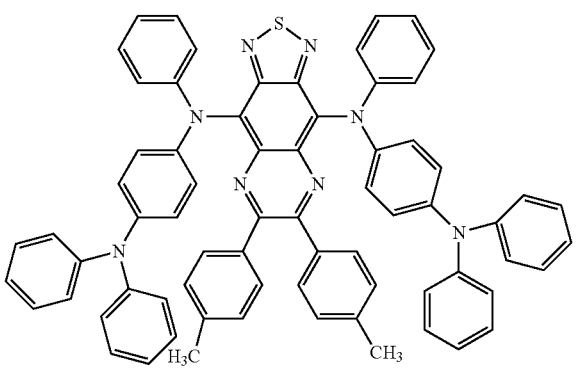

-continued (410)

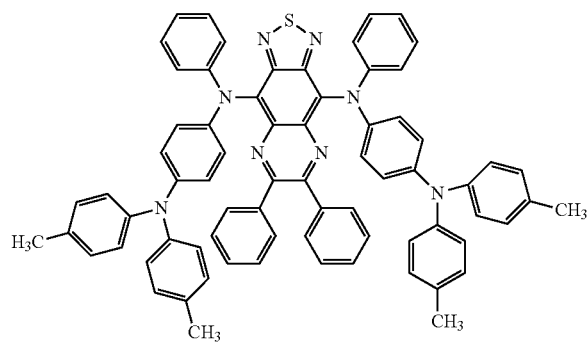

(411)

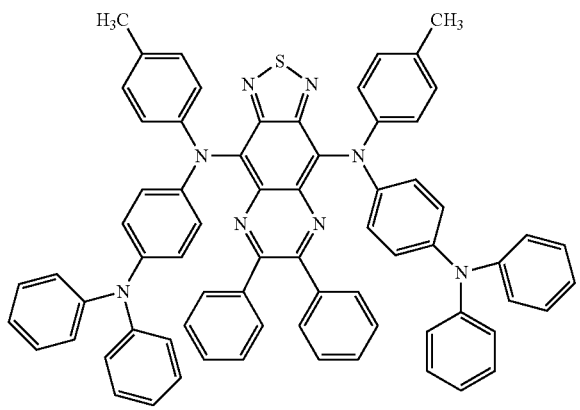

The organic compounds represented by Structural Formulae (100) to (112), (200) to (211), (300) to (309), and (400) to (411) are examples of the organic compound represented by General Formula (G1). The organic compound of one embodiment of the present invention is not limited thereto.

Next, a synthesis method of an organic compound of one embodiment of the present invention having m and n being 1 in General Formula (G1), that is, an organic compound represented by General Formula (G1-1) is described.

[Chemical Formula 29]

(G1)

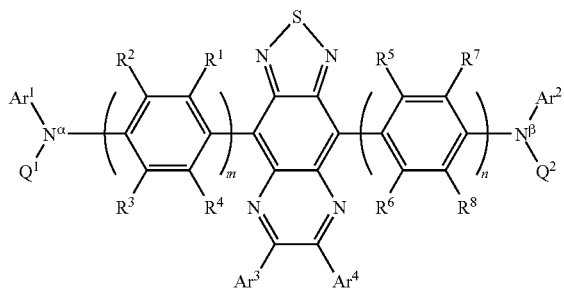

In General Formula (G1), $Ar^1$ to $Ar^4$ each independently represent a substituted or unsubstituted aryl group having 6 to 13 carbon atoms in a ring. Furthermore, $R^1$ to $R^8$ each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring. Furthermore, $Q^1$ and $Q^2$ each independently represent a substituted or unsubstituted group having a carbazole skeleton or a substituted or unsubstituted group having a triarylamine skeleton and having 18 to 30 carbon atoms in a ring. Note that three aryl groups in the triarylamine skeleton may have the same structure or different structures. In addition, m and n each represent 1.

[Chemical Formula 30]

(G1-1)

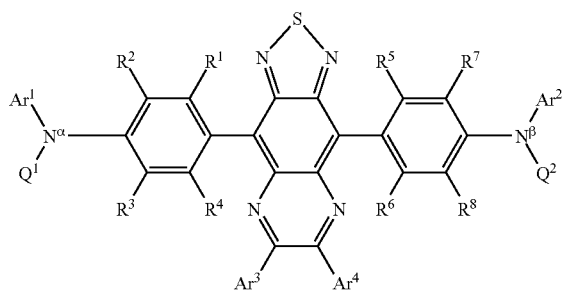

In General Formula (G1-1), $Ar^1$ to $Ar^4$ each independently represent a substituted or unsubstituted aryl group having 6 to 13 carbon atoms in a ring. Furthermore, $R^1$ to $R^8$ each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring. Furthermore, $Q^1$ and $Q^2$ each independently represent a substituted or unsubstituted group having a carbazole skeleton or a substituted or unsubstituted group having a triarylamine skeleton and having 18 to 30 carbon atoms in a ring. Note that three aryl groups in the triarylamine skeleton may have the same structure or different structures.

<<Synthesis Method of Organic Compound Represented by General Formula (G1-1)>>

An example of a synthesis method of the organic compound represented by General Formula (G1-1) is described below. A variety of reactions can be applied to the synthesis of this organic compound. For example, as shown in Synthesis Scheme (A-1), a dithiazoloquinoxaline compound (Compound 1) is coupled with a triarylamine compound (Compound 2) to obtain a dithiazoloquinoxaline compound (Compound 3). Then, as shown in Synthesis Scheme (A-2), the dithiazoloquinoxaline compound (Compound 3) is coupled with a triarylamine compound (Compound 4) to obtain the dithiazoloquinoxaline compound represented by General Formula (G1-1).

[Chemical Formula 31]

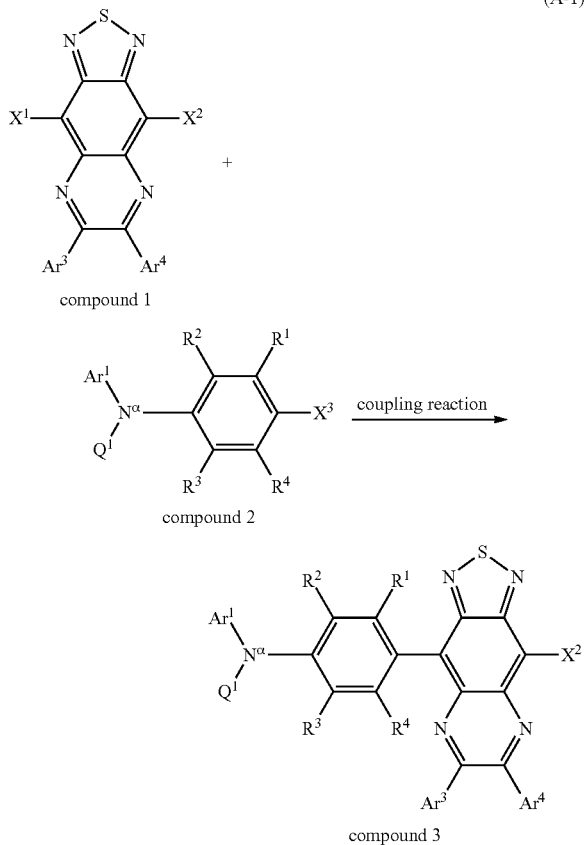

[Chemical Formula 32]

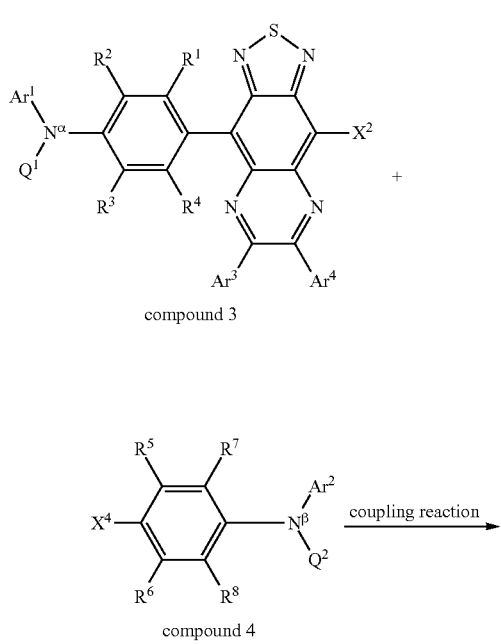

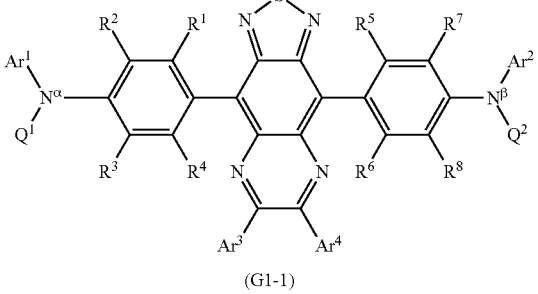

In Synthesis Schemes (A-1) and (A-2), $Ar^1$ to $Ar^4$ each independently represent a substituted or unsubstituted aryl group having 6 to 13 carbon atoms in a ring. Furthermore, $R^1$ to $R^8$ each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring. Furthermore, $Q^1$ and $Q^2$ each independently represent a substituted or unsubstituted group having a carbazole skeleton or a substituted or unsubstituted group having a triarylamine skeleton and having 18 to 30 carbon atoms in a ring. Note that three aryl groups in the triarylamine skeleton may have the same structure or different structures. In addition, $X^1$ to $X^4$ each independently represent any one of chlorine, bromine, iodine, a triflate group, an organoboron group, and a boronic acid.

Suzuki-Miyaura cross-coupling reaction using a palladium catalyst is performed in Synthesis Schemes (A-1) and (A-2). In the Suzuki-Miyaura cross-coupling reaction, bis(dibenzylideneacetone)palladium(0), palladium(II) acetate, [1,1'-bis(diphenylphosphino)ferrocene]palladium(II) dichloride, tetrakis(triphenylphosphine)palladium(0), or the like can be used as a palladium compound. In addition, a ligand such as tri(tert-butyl)phosphine, tri(n-hexyl)phosphine, tricyclohexylphosphine, di(1-adamantyl)-n-butylphosphine, 2-dicyclohexylphosphino-2',6'-dimethoxybiphenyl, or tri(ortho-tolyl)phosphine can be used.

In the reaction, an organic base such as sodium tert-butoxide, an inorganic base such as potassium carbonate, cesium carbonate, or sodium carbonate, or the like can be used. Furthermore, toluene, xylene, benzene, tetrahydrofuran, dioxane, ethanol, methanol, water, or the like can be used as a solvent. Note that reagents which can be used in the reaction are not limited to the above-described reagents.

The reaction performed under Synthesis Schemes (A-1) and (A-2) is not limited to a Suzuki-Miyaura coupling reaction; a Migita-Kosugi-Stille coupling reaction using an organotin compound, a Kumada-Tamao-Corriu coupling reaction using a Grignard reagent, a Negishi coupling reaction using an organozinc compound, a reaction using copper or a copper compound, or the like can also be employed.

In the case of using the Migita-Kosugi-Stille coupling reaction, either one of $X^1$ and a material cross-coupled with $X^1$ represents an organotin group, and the other represents a halogen group; either one of $X^4$ and a material cross-coupled with $X^4$ represents an organotin group, and the other represents a halogen group. In other words, either one of Compound 1 and Compound 2 is an organotin compound, and the other compound is a halide. In addition, either one of Compound 3 and Compound 4 is an organotin compound, and the other compound is a halide.

In the case of using the Kumada-Tamao-Corriu coupling reaction, either one of $X^1$ and a material cross-coupled with $X^1$ represents a magnesium halide group, and the other represents a halogen group; either one of $X^4$ and a material cross-coupled with $X^4$ represents a magnesium halide group, and the other represents a halogen group. In other words, either one of Compound 1 and Compound 2 is a Grignard reagent, and the other compound is a halide. In addition, either one of Compound 3 and Compound 4 is a Grignard reagent, and the other compound is a halide.

In the case of using the Negishi coupling reaction, either one of $X^1$ and a material cross-coupled with $X^1$ represents an organozinc group, and the other represents a halogen group; either one of $X^4$ and a material cross-coupled with $X^4$ represents an organozinc group, and the other represents a halogen group. In other words, either one of Compound 1 and Compound 2 is an organozinc compound, and the other compound is a halide. In addition, either one of Compound 3 and Compound 4 is an organozinc compound, and the other compound is a halide.

Next, a synthesis method of an organic compound of one embodiment of the present invention in which triarylamine skeletons have the identical molecular structure in General Formula (G1-1), that is, an organic compound represented by General Formula (G1-2) is described.

[Chemical Formula 33]

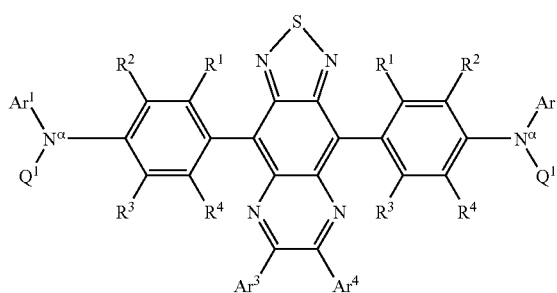

(G1-2)

In General Formula (G1-2), $Ar^1$, $Ar^3$, and $Ar^4$ represent a substituted or unsubstituted aryl group having 6 to 13 carbon atoms in a ring. Furthermore, $R^1$ to $R^4$ each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring. Furthermore, $Q^1$ represents a substituted or unsubstituted group having a carbazole skeleton or a substituted or unsubstituted group having a triarylamine skeleton and having 18 to 30 carbon atoms in a ring. Note that three aryl groups in the triarylamine skeleton have the same structure.

<<Synthesis Method of Organic Compound Represented by General Formula (G1-2)>>

An example of a synthesis method of the organic compound represented by General Formula (G1-2) is described below. A variety of reactions can be applied to the synthesis of this organic compound. For example, as shown in Synthesis Scheme (B-1), two equivalents of a triarylamine compound (Compound 2) are coupled with a dithiazoloquinoxaline compound (Compound 1) to obtain the dithiazoloquinoxaline compound (G1-2).

[Chemical Formula 34]

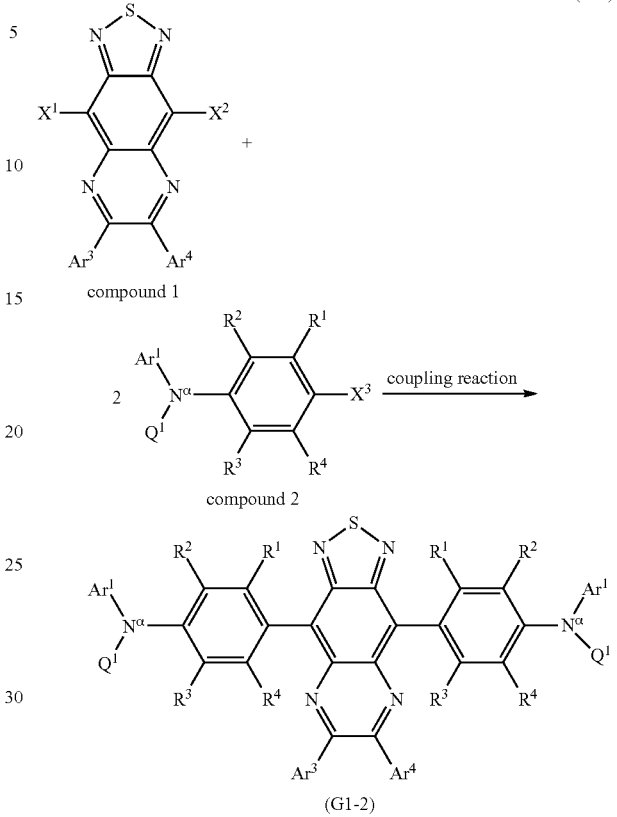

In Synthesis Scheme (B-1), $Ar^1$, $Ar^3$, and $Ar^4$ represent a substituted or unsubstituted aryl group having 6 to 13 carbon atoms in a ring. Furthermore, $R^1$ to $R^4$ each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring. Furthermore, $Q^1$ and $Q^2$ each independently represent a substituted or unsubstituted group having a carbazole skeleton or a substituted or unsubstituted group having a triarylamine skeleton and having 18 to 30 carbon atoms in a ring. Note that three aryl groups in the triarylamine skeleton may have the same structure or different structures. In addition, $X^1$ to $X^3$ each independently represent any one of chlorine, bromine, iodine, a triflate group, an organoboron group, and a boronic acid.

In Synthesis Scheme (B-1), in a manner similar to that of the synthesis method of General Formula (G1-1), a Suzuki-Miyaura cross-coupling reaction using a palladium catalyst is performed. The reaction performed under Synthesis Scheme (B-1) is, as in the synthesis method of General Formula (G1-1), not limited to a Suzuki-Miyaura coupling reaction; a Migita-Kosugi-Stille coupling reaction using an organotin compound, a Kumada-Tamao-Corriu coupling reaction using a Grignard reagent, a Negishi coupling reaction using an organozinc compound, a reaction using copper or a copper compound, or the like can also be employed.

Next, a synthesis method of an organic compound of one embodiment of the present invention having m and n being 0 in General Formula (G1), that is, an organic compound represented by General Formula (G1-3) is described.

[Chemical Formula 35]

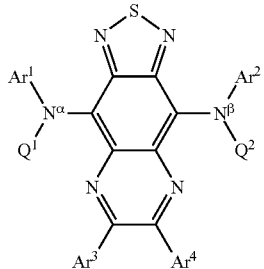

(G1-3)

In General Formula (G1-3), $Ar^1$ to $Ar^4$ each independently represent a substituted or unsubstituted aryl group having 6 to 13 carbon atoms in a ring. Furthermore, $Q^1$ and $Q^2$ each independently represent a substituted or unsubstituted group having a carbazole skeleton or a substituted or unsubstituted group having a triarylamine skeleton and having 18 to 30 carbon atoms in a ring.

<<Synthesis Method of Organic Compound Represented by General Formula (G1-3)>>

An example of a synthesis method of the organic compound represented by General Formula (G1-3) is described below. A variety of reactions can be applied to the synthesis of this organic compound. For example, as shown in Synthesis Scheme (C-1), a dithiazoloquinoxaline compound (Compound 1) is coupled with a diarylamine compound (Compound 5) to obtain a dithiazoloquinoxaline compound (Compound 6). Then, as shown in Synthesis Scheme (C-2), the dithiazoloquinoxaline compound (Compound 6) is coupled with a diarylamine compound (Compound 7) to obtain the dithiazoloquinoxaline compound represented by General Formula (G1-3).

[Chemical Formula 36]

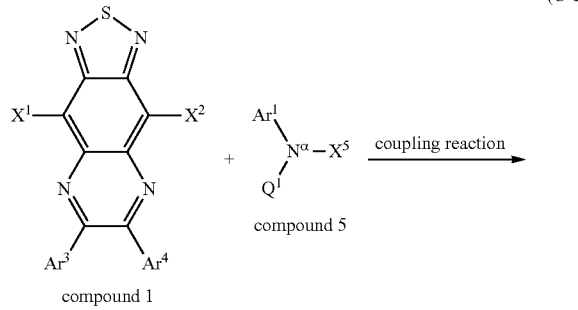

(C-1)

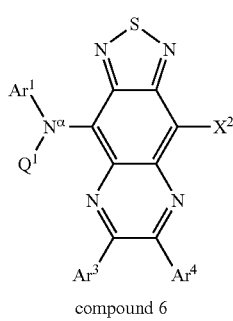

compound 6

[Chemical Formula 37]

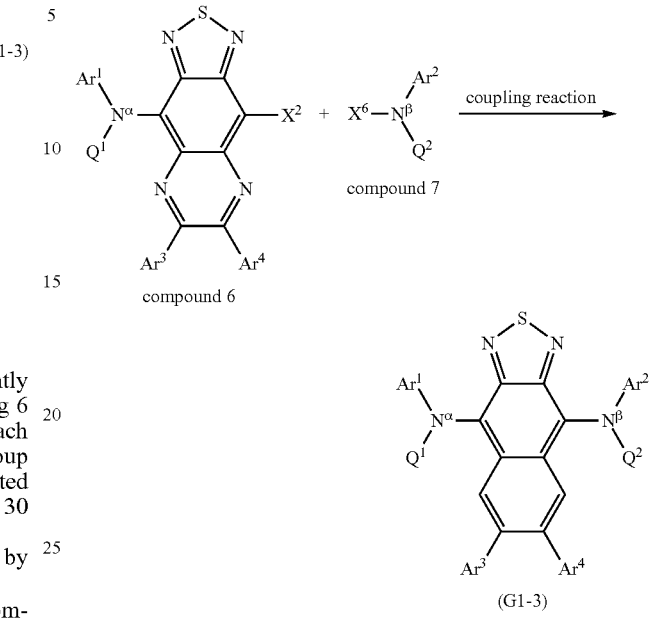

(C-2)

In Synthesis Schemes (C-1) and (C-2), $Ar^1$ to $Ar^4$ each independently represent a substituted or unsubstituted aryl group having 6 to 13 carbon atoms in a ring. Furthermore, $Q^1$ and $Q^2$ each independently represent a substituted or unsubstituted group having a carbazole skeleton or a substituted or unsubstituted group having a triarylamine skeleton and having 18 to 30 carbon atoms in a ring. Note that three aryl groups in the triarylamine skeleton may have the same structure or different structures. In addition, $X^1$ and $X^2$ each independently represent any one of chlorine, bromine, iodine, and a triflate group, and $X^5$ and $X^6$ each independently represent hydrogen or an organotin group.

In the case where a Buchwald-Hartwig reaction using a palladium catalyst is performed in Synthesis Schemes (C-1) and (C-2), a palladium compound such as bis(dibenzylideneacetone)palladium(0), palladium(II) acetate, [1,1-bis(diphenylphosphino)ferrocene]palladium(II) dichloride, tetrakis(triphenylphosphine)palladium(0), or allylpalladium(II) chloride (dimer) can be used. Furthermore, a ligand such as tri(tert-butyl)phosphine, tri(n-hexyl)phosphine, tricyclohexylphosphine, di(1-adamantyl)-n-butylphosphine, 2-dicyclohexylphosphino-2',6'-dimethoxybiphenyl, tri(ortho-tolyl)phosphine, or (S)-(6,6'-dimethoxybiphenyl-2,2'-diyl)bis(diisopropylphosphine) (abbreviation: cBRIDP) can be used.

In the reaction, an organic base such as sodium tert-butoxide, an inorganic base such as potassium carbonate, cesium carbonate, or sodium carbonate, or the like can be used. Furthermore, toluene, xylene, benzene, tetrahydrofuran, dioxane, or the like can be used as a solvent. Note that reagents which can be used in the reaction are not limited to the above-described reagents.

In the case where an Ullmann reaction using copper or a copper compound is performed in Synthesis Schemes (C-1) and (C-2), $X^1$ and $X^2$ each independently represent any one of chlorine, bromine, and iodine, and $X^5$ and $X^6$ represent hydrogen.

In the reaction, an inorganic base such as potassium carbonate can be used. As a solvent, 1,3-dimethyl-3,4,5,6-tetrahydro-2(1H)-pyrimidinone (DMPU), toluene, xylene, benzene, or the like can be used. It should be noted in the reaction (Ullmann reaction) that the target substance can be obtained in a shorter time and in a higher yield when the reaction temperature is 100° C. or higher; therefore, using DMPU or xylene with high boiling temperatures is preferable. Furthermore, a reaction temperature of 150° C. or higher is further preferred, and accordingly, DMPU is further preferably used. Note that reagents which can be used in the reaction are not limited to the above-described reagents.

Next, a synthesis method of an organic compound of one embodiment of the present invention which has m and n being 0 and triarylamine skeletons having the identical molecular structure in General Formula (G1), that is, an organic compound represented by General Formula (G1-4) is described.

[Chemical Formula 38]

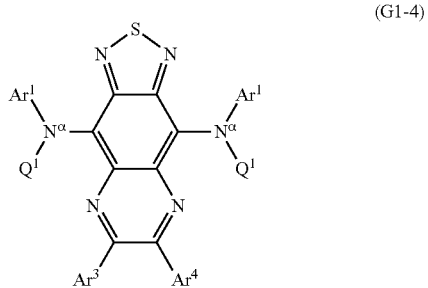

(G1-4)

In General Formula (G1-4), $Ar^1$, $Ar^3$, and $Ar^4$ represent a substituted or unsubstituted aryl group having 6 to 13 carbon atoms in a ring. Furthermore, each $Q^1$ independently represents a substituted or unsubstituted group having a carbazole skeleton or a substituted or unsubstituted group having a triarylamine skeleton and having 18 to 30 carbon atoms in a ring. Note that three aryl groups in the triarylamine skeleton may have the same structure or different structures.

<<Synthesis Method of Organic Compound Represented by General Formula (G1-4)>>

An example of a synthesis method of the organic compound represented by General Formula (G1-4) is described below. A variety of reactions can be applied to the synthesis of this organic compound. For example, as shown in Synthesis Scheme (D-1), two equivalents of a diarylamine compound (Compound 5) are coupled with a dithiazoloquinoxaline compound (Compound 1) to obtain the dithiazoloquinoxaline compound represented by General Formula (G1-4).

[Chemical Formula 39]

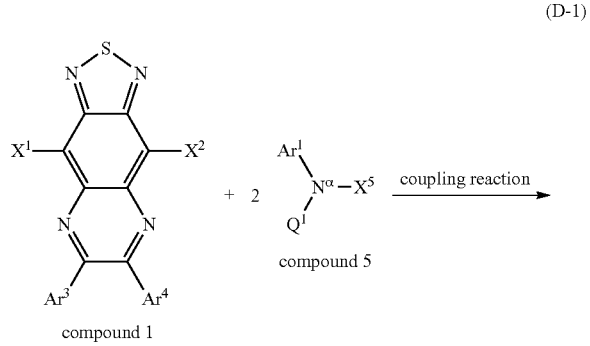

(D-1)

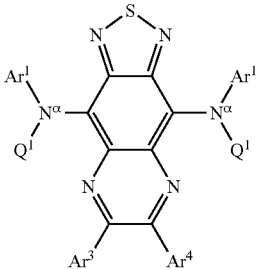

In Synthesis Scheme (D-1), $Ar^1$, $Ar^3$, and $Ar^4$ represent a substituted or unsubstituted aryl group having 6 to 13 carbon atoms in a ring. Furthermore, $Q^1$ represents a substituted or unsubstituted group having a carbazole skeleton or a substituted or unsubstituted group having a triarylamine skeleton and having 18 to 30 carbon atoms in a ring. Note that three aryl groups in the triarylamine skeleton may have the same structure or different structures. In addition, $X^1$ and $X^2$ each independently represent any one of chlorine, bromine, iodine, and a triflate group, and $X^5$ represents hydrogen or an organotin group.

In the case where an Ullmann reaction using copper or a copper compound is performed in Synthesis Scheme (C-1) in a manner similar to that of the synthesis method of General Formula (G1-3), $X^1$ and $X^2$ each independently represent any one of chlorine, bromine, and iodine, and $X^5$ represents hydrogen.

Although an example of a method for synthesizing the organic compound of one embodiment of the present invention is described above, the present invention is not limited thereto and any other synthesis methods may be employed.

The structures described in this embodiment can be used in combination with any of the structures described in the other embodiments, as appropriate.

Embodiment 2

In this embodiment, an embodiment of a light-emitting device in which an organic compound of an embodiment of the present invention can be used will be described.

<Structure Example of Light-Emitting Device>

FIG. 1A illustrates an example of a light-emitting device including an EL layer that includes a light-emitting layer between a pair of electrodes. Specifically, an EL layer 103 is interposed between a first electrode 101 and a second electrode 102. For example, in the case where the first electrode 101 is an anode, the EL layer 103 has a structure in which a hole-injection layer 111, a hole-transport layer 112, a light-emitting layer 113, an electron-transport layer 114, and an electron-injection layer 115 are stacked as functional layers in this order.

Figure 1B:
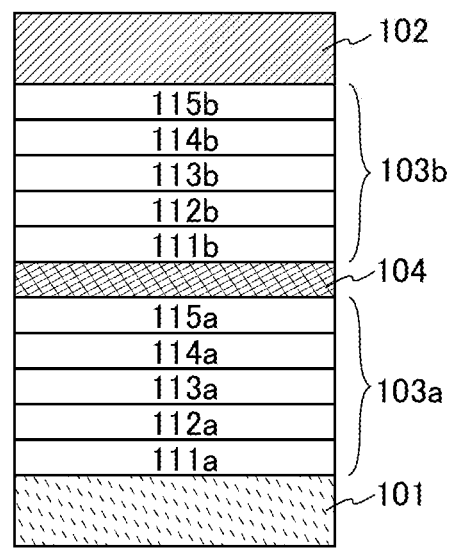

Embodiments of the present invention also include light-emitting devices having other structures, such as a light-emitting device that can be driven at low voltage by having a structure (tandem structure) in which a plurality of EL layers are provided between a pair of electrodes and a charge-generation layer 104 is provided between the EL layers as illustrated in FIG. 1B, and a light-emitting device having a micro-optical resonator (microcavity) structure between a pair of electrodes and thus having improved optical characteristics. The charge-generation layer has a function of injecting electrons into one of the adjacent EL layers and injecting holes into the other of the EL layers when a voltage is applied between the first electrode 101 and the second electrode 102.

At least one of the first electrode 101 and the second electrode 102 of the light-emitting device is a light-transmitting electrode (e.g., a transparent electrode or a transflective electrode). In the case where the light-transmitting electrode is a transparent electrode, the transparent electrode has a visible light transmittance higher than or equal to 40%. In the case where the light-transmitting electrode is a transflective electrode having both a transmitting property and a reflective property, the transflective electrode has a visible light reflectance higher than or equal to 20% and lower than or equal to 80%, preferably higher than or equal to 40% and lower than or equal to 70%. These electrodes preferably have a resistivity of $1 \times 10^{-2}$ Ωcm or less.

Furthermore, when one of the first electrode 101 and the second electrode 102 is a reflective electrode in the above-described light-emitting device, the visible light reflectance of the reflective electrode is higher than or equal to 40% and lower than or equal to 100%, preferably higher than or equal to 70% and lower than or equal to 100%. This electrode preferably has a resistivity of $1 \times 10^{-2}$ Ωcm or less.

The above-described tandem structure includes a plurality of EL layers between which a charge-generation layer is formed, and the plurality of EL layers each include a light-emitting layer. The combination of emission colors of the light-emitting layers can be determined freely. For example, the emission color of a first light-emitting layer included in a first EL layer stacked over the first electrode 101 can be any of red, green, yellow, and blue; the emission color of a second light-emitting layer included in a second EL layer stacked over the first EL layer with a charge-generation layer interposed therebetween can be any of red, green, yellow, and blue; and the emission color of a third light-emitting layer included in a third EL layer stacked over the second EL layer with another charge-generation layer interposed therebetween can be any of red, green, yellow, and blue.

To form the above-described microcavity structure, a reflective electrode is formed as the first electrode 101 of the light-emitting device, and a transflective electrode is formed as the second electrode 102, for example. In other words, when the first electrode 101 of the light-emitting device is a reflective electrode having a stacked structure of a reflective conductive material and a light-transmitting conductive material (transparent conductive film), optical adjustment can be performed by adjusting the thickness of the transparent conductive film. Specifically, when the wavelength of light obtained from the light-emitting layer 113 is λ, the distance between the first electrode 101 and the second electrode 102 is preferably adjusted to be in the neighborhood of mλ/2 (m is a natural number). Thus, light emitted by the EL layer 103 can be intensified.

To amplify desired light (wavelength: λ) obtained from the light-emitting layer 113, the optical path length from the first electrode 101 to a region where the desired light is obtained in the light-emitting layer 113 (light-emitting region) and the optical path length from the second electrode 102 to the region where the desired light is obtained in the light-emitting layer 113 (light-emitting region) are preferably adjusted to be in the neighborhood of (2m'+1)λ/4 (m' is a natural number). Here, the light-emitting region means a region where holes and electrons are recombined in the light-emitting layer 113.

By such optical adjustment, the spectrum of specific monochromatic light obtained from the light-emitting layer 113 can be narrowed and light emission with high color purity can be obtained.

In that case, the optical path length between the first electrode 101 and the second electrode 102 is, to be exact, the total thickness from a reflective region in the first electrode 101 to a reflective region in the second electrode 102. However, it is difficult to precisely determine the reflective regions in the first electrode 101 and the second electrode 102; thus, it is assumed that the above effect can be sufficiently obtained wherever the reflective regions may be set in the first electrode 101 and the second electrode 102. Furthermore, the optical path length between the first electrode 101 and the light-emitting layer that emits the desired light is, to be exact, the optical path length between the reflective region in the first electrode 101 and the light-emitting region in the light-emitting layer that emits the desired light. However, it is difficult to precisely determine the reflective region in the first electrode 101 and the light-emitting region in the light-emitting layer that emits the desired light; thus, it is assumed that the above effect can be sufficiently obtained wherever the reflective region and the light-emitting region may be set in the first electrode 101 and the light-emitting layer that emits the desired light, respectively.

In the case where the light-emitting device has a microcavity structure in the above-described manner, even when an EL layer is shared, light (monochromatic light) with different wavelengths can be extracted by changing the optical path length between electrodes. Thus, side-by-side patterning to obtain light emissions of different colors (e.g., RGB) is not needed, leading to higher resolution. Furthermore, a combination with coloring layers (color filters) is also possible. Moreover, the emission intensity of light with a specific wavelength in the front direction can be increased, whereby power consumption can be reduced.

<First Electrode and Second Electrode>

As materials for the first electrode 101 and the second electrode 102, any of the following materials can be used in an appropriate combination as long as the above functions of the electrodes can be fulfilled. For example, a metal, an alloy, an electrically conductive compound, a mixture of these, and the like can be used as appropriate. Specifically, an In—Sn oxide (also referred to as ITO), an In—Si—Sn oxide (also referred to as ITSO), an In—Zn oxide, or an In—W—Zn oxide can be used. In addition, it is possible to use a metal such as aluminum (Al), titanium (Ti), chromium (Cr), manganese (Mn), iron (Fe), cobalt (Co), nickel (Ni), copper (Cu), gallium (Ga), zinc (Zn), indium (In), tin (Sn), molybdenum (Mo), tantalum (Ta), tungsten (W), palladium (Pd), gold (Au), platinum (Pt), silver (Ag), yttrium (Y), or neodymium (Nd) or an alloy containing an appropriate combination of any of these metals. It is also possible to use a Group 1 element or a Group 2 element in the periodic table that is not described above (e.g., lithium (Li), cesium (Cs), calcium (Ca), or strontium (Sr)), a rare earth metal such as europium (Eu) or ytterbium (Yb), an alloy containing an appropriate combination of any of these elements, graphene, or the like.

For fabrication of these electrodes, a sputtering method or a vacuum evaporation method can be used.

<Hole-Injection Layer>

The hole-injection layer 111 injects holes from the first electrode 101 that is an anode and the charge-generation layer 104 to the EL layers (103, 103a, and 103b) and contain an organic acceptor material (electron-accept material).

For the hole-injection layer 111, an organic acceptor material (electron-accept material) and a hole-transport material can be used. In that case, the organic acceptor material exhibits an electron-accepting property with respect to the hole-transport material. Specific examples of the organic acceptor material include transition metal oxides such as molybdenum oxide, vanadium oxide, ruthenium oxide, tungsten oxide, and manganese oxide. It is also possible to use a phthalocyanine-based compound such as phthalocyanine (abbreviation: $H_2Pc$) or copper phthalocyanine (abbreviation: CuPc), a low-molecular compound, a high-molecular compound, or the like. As the hole-transport material, a material having a deep HOMO level, specifically a relatively deep HOMO level higher than or equal to −5.7 eV and lower than or equal to −5.4 eV is preferable. The hole-transport material with a relatively deep HOMO level facilitates hole injection into the hole-transport layer 112.

As the organic acceptor material, an organic compound having an electron-withdrawing group (particularly a cyano group or a halogen group such as a fluoro group) can be used, for example. The hole-injection layer 111 may be formed of such an organic acceptor material alone or in combination with a hole-transport material.

Examples of such an organic compound having an electron-withdrawing group include 7,7,8,8-tetracyano-2,3,5,6-tetrafluoroquinodimethane (abbreviation: F4-TCNQ), chloranil, 2,3,6,7,10,11-hexacyano-1,4,5,8,9,12-hexaazatriphenylene (abbreviation: HAT-CN), 1,3,4,5,7,8-hexafluorotetracyano-naphthoquinodimethane (abbreviation: F6-TCNNQ), and 2-(7-dicyanomethylene-1,3,4,5,6,8,9,10-octafluoro-7H-pyren-2-ylidene)malononitrile. A compound in which electron-withdrawing groups are bonded to a condensed heterocyclic compound having a plurality of heteroatoms, such as HAT-CN, is preferred because it is thermally stable. A [3]radialene derivative having an electron-withdrawing group (in particular, a cyano group or a halogen group such as a fluoro group) has a very high electron-accepting property and thus is preferred. Specific examples include α,α',α"-1,2,3-cyclopropanetriylidenetris[4-cyano-2,3,5,6-tetrafluorobenzeneacetonitrile], α,α',α"-1,2,3-cyclopropanetriylidenetris[2,6-dichloro-3,5-difluoro-4-(trifluoromethyl)benzeneacetonitrile], and α,α',α"-1,2,3-cyclopropanetriylidenetris[2,3,4,5,6-pentafluorobenzeneacetonitrile].

As the hole-transport material, a known material can be used; particularly in the case of using a hole-transport material with a deep HOMO level, the hole-transport material preferably has any of a carbazole skeleton, a dibenzofuran skeleton, a dibenzothiophene skeleton, and an anthracene skeleton. In particular, an aromatic amine having a substituent that includes a dibenzofuran ring or a dibenzothiophene ring, an aromatic monoamine that includes a naphthalene ring, or an aromatic monoamine in which a 9-fluorenyl group is bonded to nitrogen of amine through an arylene group may be used.

As the hole-transport material (including the hole-transport material with a deep HOMO level), it is preferable to use a substance having a hole mobility higher than or equal to $1\times10^{-6}$ $cm^2/Vs$ in the case where the square root of the electric field strength [V/cm] is 600. Note that other substances can also be used as long as the substances have a hole-transport property higher than an electron-transport property. Note that the substances preferably have an N,N-bis(4-biphenyl)amino group in order to fabricate a light-emitting device having a long lifetime.

Specific examples of the hole-transport material include N-(4-biphenyl)-6,N-diphenylbenzo[b]naphtho[1,2-d]furan-8-amine (abbreviation: BnfABP), N,N-bis(4-biphenyl)-6-phenylbenzo[b]naphtho[1,2-d]furan-8-amine (abbreviation: BBABnf), 4,4'-bis(6-phenylbenzo[b]naphtho[1,2-d]furan-8-yl)-4"-phenyltriphenylamine (abbreviation: BnfBB1BP), N,N-bis(4-biphenyl)benzo[b]naphtho[1,2-d]furan-6-amine (abbreviation: BBABnf(6)), N,N-bis(4-biphenyl)benzo[b]naphtho[1,2-d]furan-8-amine (abbreviation: BBABnf(8)), N,N-bis(4-biphenyl)benzo[b]naphtho[2,3-d]furan-4-amine (abbreviation: BBABnf(II)(4)), N,N-bis[4-(dibenzofuran-4-yl)phenyl]-4-amino-p-terphenyl (abbreviation: DBfBB1TP), N-[4-(dibenzothiophen-4-yl)phenyl]-N-phenyl-4-biphenylamine (abbreviation: ThBA1BP), 4-(2-naphthyl)-4',4"-diphenyltriphenylamine (abbreviation: BBAβNB), 4-[4-(2-naphthyl)phenyl]-4',4"-diphenyltriphenylamine (abbreviation: BBAβNBi), 4,4'-diphenyl-4"-(6;1'-binaphthyl-2-yl)triphenylamine (abbreviation: BBAαNβNB), 4,4'-diphenyl-4"-(7;1'-binaphthyl-2-yl)triphenylamine (abbreviation: BBAαNβNB-03), 4,4'-diphenyl-4"-(7-phenyl)naphthyl-2-yltriphenylamine (abbreviation: BBAPβNB-03), 4,4'-diphenyl-4"-(6;2-binaphthyl-2-yl)triphenylamine (abbreviation: BBA(βN2)B), 4,4'-diphenyl-4"-(7;2'-binaphthyl-2-yl)triphenylamine (abbreviation: BBA(βN2)B-03), 4,4'-diphenyl-4"-(4;2'-binaphthyl-1-yl)triphenylamine (abbreviation: BBAβNαNB), 4,4'-diphenyl-4"-(5;2'-binaphthyl-1-yl)triphenylamine (abbreviation: BBAβNαNB-02), 4-(4-biphenylyl)-4'-(2-naphthyl)-4"-phenyltriphenylamine (abbreviation: TPBiAβNB), 4-(3-biphenylyl)-4'-[4-(2-naphthyl)phenyl]-4"-phenyltriphenylamine (abbreviation: mTPBiAβNBi), 4-(4-biphenylyl)-4'-[4-(2-naphthyl)phenyl]-4"-phenyltriphenylamine (abbreviation: TPBiAβNBi), 4-phenyl-4'-(1-naphthyl)-triphenylamine (abbreviation: αNBA1BP), 4,4'-bis(1-naphthyl)triphenylamine (abbreviation: αNBB1BP), 4,4'-diphenyl-4"-[4'-(carbazol-9-yl)biphenyl-4-yl]triphenylamine (abbreviation: YGTBi1BP), 4'-[4-(3-phenyl-9H-carbazol-9-yl)phenyl]tris(1,1'-biphenyl-4-yl)amine (abbreviation: YGTBi1BP-02), 4-[4'-(carbazol-9-yl)biphenyl-4-yl]-4'-(2-naphthyl)-4"-phenyltriphenylamine (abbreviation: YGTBiβNB), N-[4-(9-phenyl-9H-carbazol-3-yl)phenyl]-N-[4-(1-naphthyl)phenyl]-9,9'-spirobi[9H-fluoren]-2-amine (abbreviation: PCBNBSF), N,N-bis(4-biphenylyl)-9,9'-spirobi[9H-fluoren]-2-amine (abbreviation: BBASF), N,N-bis(1,1'-biphenyl-4-yl)-9,9'-spirobi[9H-fluoren]-4-amine (abbreviation: BBASF(4)), N-(1,1'-biphenyl-2-yl)-N-(9,9-dimethyl-9H-fluoren-2-yl)-9,9'-spirobi[9H-fluoren]-4-amine (abbreviation: oFBiSF), N-(4-biphenyl)-N-(9,9-dimethyl-9H-fluoren-2-yl)dibenzofuran-4-amine (abbreviation: FrBiF), N-[4-(1-naphthyl)phenyl]-N-[3-(6-phenyldibenzofuran-4-yl)phenyl]-1-naphthylamine (abbreviation: mPDBfBNBN), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-[4-(9-phenylfluoren-9-yl)phenyl]triphenylamine (abbreviation: BPAFLBi), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), N-phenyl-N-[4-(9-phenyl-9H-carbazol-3-yl)phenyl]spiro-9,9'-bifluoren-2-amine (abbreviation: PCBASF), and N-(1,1'-biphenyl-4-yl)-9,9-dimethyl-N-[4-(9-phenyl-9H-carbazol-3-yl)phenyl]-9H-fluoren-2-amine (abbreviation: PCBBiF).

The hole-injection layer 111 can be formed by any of known deposition methods such as a vacuum evaporation method.

<Hole-Transport Layer>

The hole-transport layer 112 transports holes injected from the first electrode 101 through the hole-injection layer 111, to the light-emitting layer 113.

The hole-transport layer 112 can be formed using a known hole-transport material other than the above-described hole-transport material. The hole-transport layer 112 may have a stacked-layer structure. Note that in the case where the hole-transport layer 112 has a stacked-layer structure, a layer on the light-emitting layer side may function as an electron-blocking layer.

It is preferable that materials be selected so that the HOMO level of the hole-transport material used in the hole-transport layer 112 is deeper than that of the hole-transport material used in the hole-injection layer 111 and a difference between the HOMO levels is less than or equal to 0.2 eV. It is further preferable that the hole-transport materials are the same material, which leads to smooth hole injection.

In the case where the hole-transport layer 112 has a stacked-layer structure, the HOMO level of the hole-transport material used in the hole-transport layer formed on the light-emitting layer 113 side is preferably deeper than that of the hole-transport material used in the hole-transport layer formed on the hole-injection layer 111 side. It is preferable that the materials be selected so that a difference between the HOMO levels is less than or equal to 0.2 eV. Owing to the above-described relation between the HOMO levels of the hole-transport materials used for the hole-injection layer 111 and the hole-transport layer 112 having a stacked-layer structure, holes are injected into each layer smoothly, which prevents an increase in driving voltage and deficiency of holes in the light-emitting layer 113.

Preferably, the hole-transport materials used for the hole-injection layer 111 and the hole-transport layer 112 each have a hole-transport skeleton. A carbazole skeleton, a dibenzofuran skeleton, a dibenzothiophene skeleton, and an anthracene skeleton, with which the HOMO levels of the hole-transport materials do not become too shallow, are preferably used as the hole-transport skeleton. The hole-transport materials used for adjacent layers in the hole-injection layer 111 and the hole-transport layer 112 having a stacked-layer structure preferably have the same hole-transport skeleton, in which case holes can be injected smoothly. In particular, a dibenzofuran skeleton is preferably used as the hole-transport skeleton.

The hole-transport materials used for adjacent layers in the hole-injection layer 111 and the hole-transport layer 112 having a stacked-layer structure are preferably the same, in which case holes can be injected more smoothly from a layer into an adjacent layer in the cathode direction.

<Light-Emitting Layer>

The organic compound of one embodiment of the present invention is preferably used for the light-emitting layer, particularly as a light-emitting substance (guest material) in the light-emitting layer. In the light-emitting device described in this embodiment, the light-emitting layer 113 may have a single-layer structure or a stacked-layer structure of a plurality of light-emitting layers. In the case where a plurality of light-emitting layers are stacked, the light-emitting layers are preferably formed to have functions different from each other.

For the light-emitting layer 113, a light-emitting substance (guest material) and one or more kinds of host materials in which the light-emitting substance is dispersed are preferably used.

As the light-emitting substance (guest material), in addition to the organic compound of one embodiment of the present invention, a substance emitting fluorescence (fluorescent substance), a substance emitting phosphorescence (phosphorescent substance), a substance exhibiting thermally activated delayed fluorescence (TADF material), other light-emitting substances, or the like can be used. As an organic compound (host material), various carrier-transport materials such as the TADF material can be used in addition to electron-transport materials and hole-transport materials. Specifically, one or more kinds of materials appropriately selected from the materials described in this specification or known materials can be used as the hole-transport materials, the electron-transport materials, or the like, for example.

Examples of the fluorescent substance that can be used as a guest material in the light-emitting layer 113 are as follows. Other fluorescent substances can also be used.

The examples include 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), —N,N'-diphenyl-N,N'-bis[4-(9-phenyl-9H-fluoren-9-yl)phenyl]pyrene-1,6-diamine (abbreviation: 1,6FLPAPrn), N,N'-bis(3-methylphenyl)-N,N'-bis[3-(9-phenyl-9H-fluoren-9-yl)phenyl]pyrene-1,6-diamine (abbreviation: 1,6mMemFLPAPrn), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), —N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tertbutyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), N,N'-diphenyl-N,N'-(1,6-pyrene-diyl)bis[(6-phenylbenzo[b]naphtho[1,2-d]furan)-8-amine] (abbreviation: 1,6BnfAPrn-03), 3,10-bis[N-(9-phenyl-9H-carbazol-2-yl)-N-phenylamino]naphtho[2,3-b;6,7-b']bisbenzofuran (abbreviation: 3,10PCA2Nbf(IV)-02), and 3,10-bis[N-(dibenzofuran-3-yl)-N-phenylamino]naphtho[2,3-b;6,7-b']bisbenzofuran (abbreviation: 3,10FrA2Nbf(IV)-02). Condensed aromatic diamine compounds typified by pyrenediamine compounds such as 1,6FLPAPrn, 1,6mMemFLPAPrn, and 1,6BnfAPrn-03 are particularly preferred because of their high hole-trapping properties, high emission efficiency, and high reliability.

Examples of the phosphorescent substance that can be used as a guest material in the light-emitting layer 113 are as follows.

The examples include an organometallic iridium complex having a 4H-triazole skeleton, such as tris{2-[5-(2-methylphenyl)-4-(2,6-dimethylphenyl)-4H-1,2,4-triazol-3-yl-κN2]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), and tris[4-(3-biphenyl)-5-isopropyl-3-phenyl-4H-1,2,4-triazolato]iridium(III) (abbreviation: [Ir(iPrptz-3b)$_3$]); an organometallic iridium complex having a 1H-triazole skeleton, such as tris[3-methyl-1-(2-methylphenyl)-5-phenyl-1H-1,2,4-triazolato]iridium(III) (abbreviation: [Ir(Mptz1-mp)$_3$]) and tris(1-methyl-5-phenyl-3-propyl-1H-1,2,4-triazolato)iridium(III) (abbreviation: [Ir(Prptz1-Me)$_3$]); an organometallic iridium complex having an imidazole skeleton, such as fac-tris[1-(2,6-diisopropylphenyl)-2-phenyl-1H-imidazole]iridium(III) (abbreviation: [Ir(iPrpmi)$_3$]) and tris[3-(2,6-dimethylphenyl)-7-methylimidazo[1,2-f]phenanthridinato]iridium(III) (abbreviation: [Ir(dmpimpt-Me)$_3$]); and an organometallic iridium complex in which a phenylpyridine derivative having an electron-withdrawing group is a ligand, such as bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis{2-[3',5'-bis(trifluoromethyl)phenyl]pyridinato-N,C$^{2'}$}iridium(III) picolinate (abbreviation: [Ir(CF$_3$ppy)$_2$(pic)]), and bis[2-(4',6'-difluorophenyl)pyridinato-N,C$^{2'}$]iridium(III) acetylacetonate (abbreviation: FIr(acac)). These compounds emit blue phosphorescence and have an emission peak at 440 nm to 520 nm.

Other examples include organometallic iridium complexes having a pyrimidine skeleton, such as tris(4-methyl-6-phenylpyrimidinato)iridium(III) (abbreviation: [Ir(mppm)$_3$]), tris(4-tert-butyl-6-phenylpyrimidinato)iridium(III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), and (acetylacetonato)bis(4,6-diphenylpyrimidinato)iridium(III) (abbreviation: [Ir(dppm)$_2$(acac)]); organometallic iridium complexes having a pyrazine skeleton, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); organometallic iridium complexes having a pyridine skeleton, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$]), and bis(2-phenylquinolinato-N,C$^{2'}$)iridium(III) acetylacetonate (abbreviation: [Ir(pq)$_2$(acac)]); and a rare earth metal complex such as tris(acetylacetonato)(monophenanthroline)terbium(III) (abbreviation: [Tb(acac)$_3$(Phen)]). These are mainly compounds that emit green phosphorescence and have an emission peak at 500 nm to 600 nm. Note that organometallic iridium complexes having a pyrimidine skeleton have distinctively high reliability and emission efficiency and thus are especially preferable.

Other examples include organometallic iridium complexes having a pyrimidine skeleton, such as (diisobutyryl-methanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), and bis[4,6-di(naphthalen-1-yl)pyrimidinato(dipivaloylmethanato)iridium(III) (abbreviation: [Ir(d1npm)$_2$(dpm)]); organometallic iridium complexes having a pyrazine skeleton, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), and (acetylacetonato)bis[2,3-bis(4-fluorophenyl)quinoxalinato]iridium(III) (abbreviation: [Ir(Fdpq)$_2$(acac)]); organometallic iridium complexes having a pyridine skeleton, such as tris(1-phenylisoquinolinato-N,C$^{2'}$)iridium(III) (abbreviation: [Ir(piq)$_3$]) and bis(1-phenylisoquinolinato-N,C$^{2'}$)iridium(III)acetylacetonate (abbreviation: [Ir(piq)$_2$(acac)]); platinum complexes such as 2,3,7,8,12,13,17,18-octaethyl-21H,23H-porphyrinplatinum(II) (abbreviation: [PtOEP]); and rare earth metal complexes such as tris(1,3-diphenyl-1,3-propanedionato) (monophenanthroline)europium(III) (abbreviation: [Eu(DBM)$_3$(Phen)]) and tris[1-(2-thenoyl)-3,3,3-trifluoroacetonato (monophenanthroline)europium(III) (abbreviation: [Eu(TTA)$_3$(Phen)]). These compounds emit red phosphorescence and have an emission peak at 600 nm to 700 nm. Furthermore, the organometallic iridium complexes having a pyrazine skeleton can provide red light emission with favorable chromaticity.

Besides the above-described materials, known phosphorescent substances can also be used.

Examples of the TADF material that can be used as the guest material in the light-emitting layer 113 are as follows.

Examples of the TADF material include a fullerene, a derivative thereof, an acridine, a derivative thereof, and an eosin derivative. Furthermore, a metal-containing porphyrin, such as a porphyrin containing magnesium (Mg), zinc (Zn), cadmium (Cd), tin (Sn), platinum (Pt), indium (In), or palladium (Pd), can be given. Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octaethylporphyrin-tin fluoride complex (SnF$_2$(OEP)), an etioporphyrin-tin fluoride complex (SnF$_2$(Etio I)), and an octaethylporphyrin-platinum chloride complex (PtCl$_2$OEP), which are represented by the following structural formulae.
[Chemical Formulae 40]
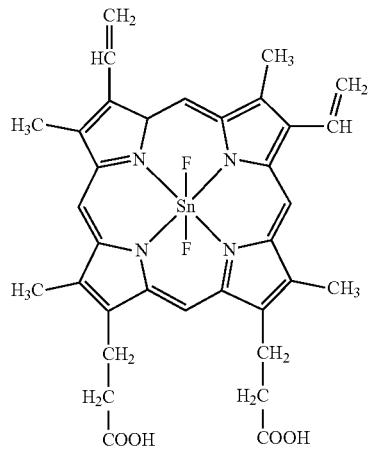
SnF$_2$(Proto IX)
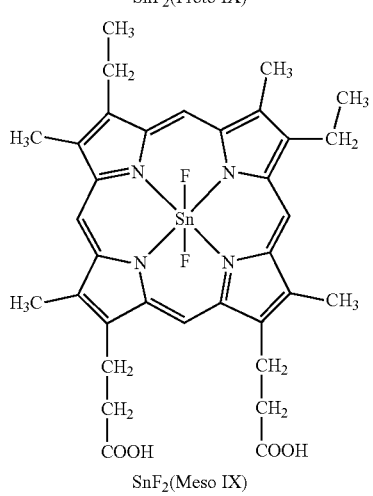
SnF$_2$(Meso IX)
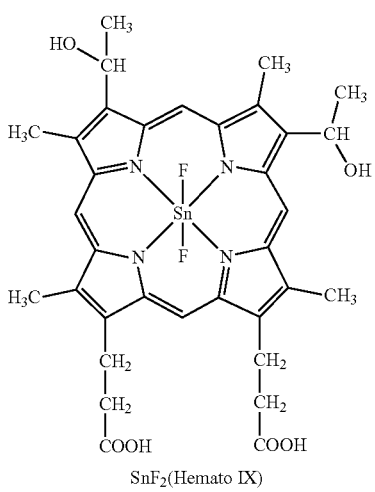
SnF$_2$(Hemato IX)
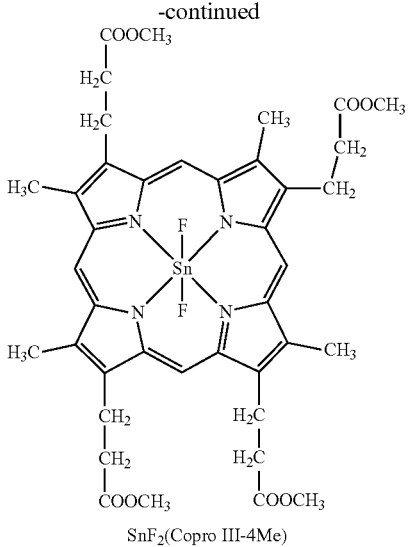
SnF$_2$(Copro III-4Me)
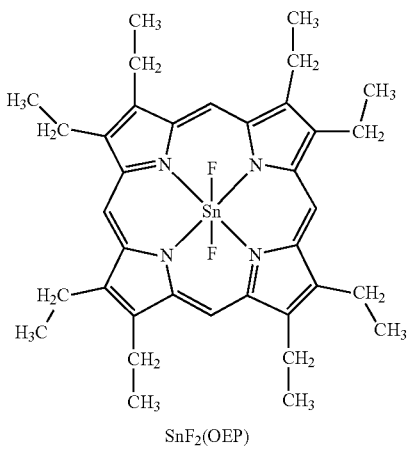
SnF$_2$(OEP)
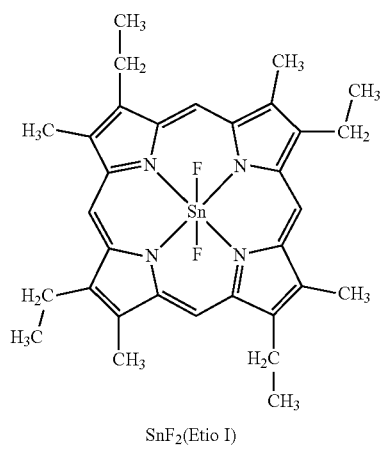
SnF$_2$(Etio I)

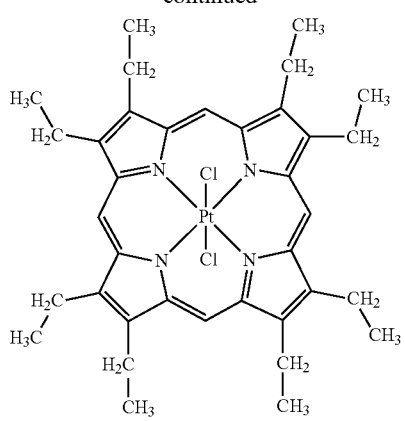

PtCl₂OEP

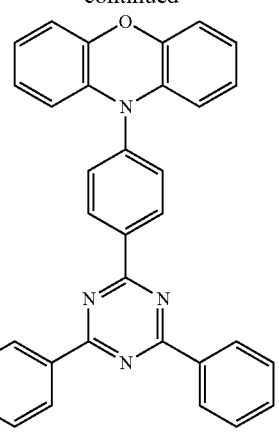

PXZ-TRZ

In addition, a heterocyclic aromatic compound having one or both of a π-electron rich heteroaromatic ring and a π-electron deficient heteroaromatic ring that is represented by the following structural formulae, such as 2-(biphenyl-4-yl)-4,6-bis(12-phenylindolo[2,3-a]carbazol-11-yl)-1,3,5-triazine (abbreviation: PIC-TRZ), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazin-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), 10-phenyl-10H,10'H-spiro[acridin-9,9'-anthracen]-10'-one (abbreviation: ACRSA), 4-(9'-phenyl-3,3'-bi-9H-carbazol-9-yl)benzofuro[3,2-d]pyrimidine (abbreviation: 4PCCzBfpm), 4-[4-(9'-phenyl-3,3'-bi-9H-carbazol-9-yl)phenyl]benzofuro[3,2-d]pyrimidine (abbreviation: 4PCCzPBfpm), or 9-[3-(4,6-diphenyl-1,3,5-triazin-2-yl)phenyl]-9'-phenyl-2,3'-bi-9H-carbazole (abbreviation: mPCCzPTzn-02) may be used.

[Chemical Formulae 41]

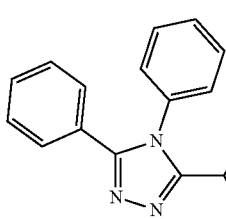

PPZ-3TPT

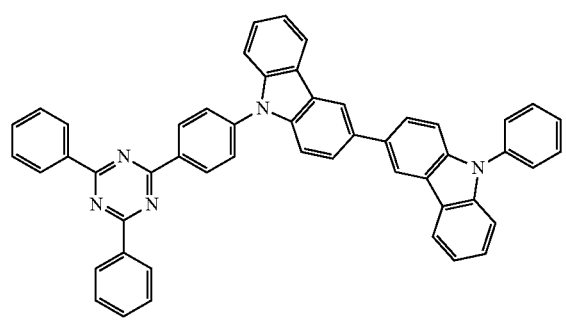

PCCzPTzn

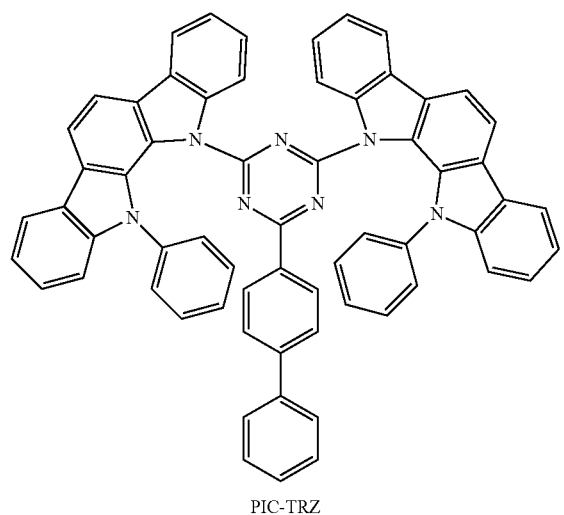

PIC-TRZ

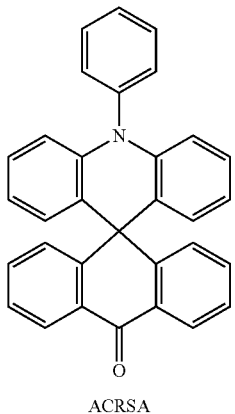

ACRSA

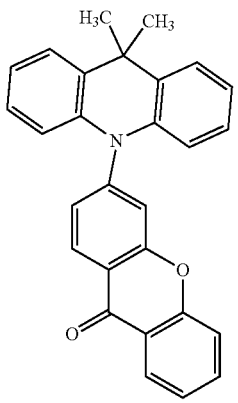

ACRXTN

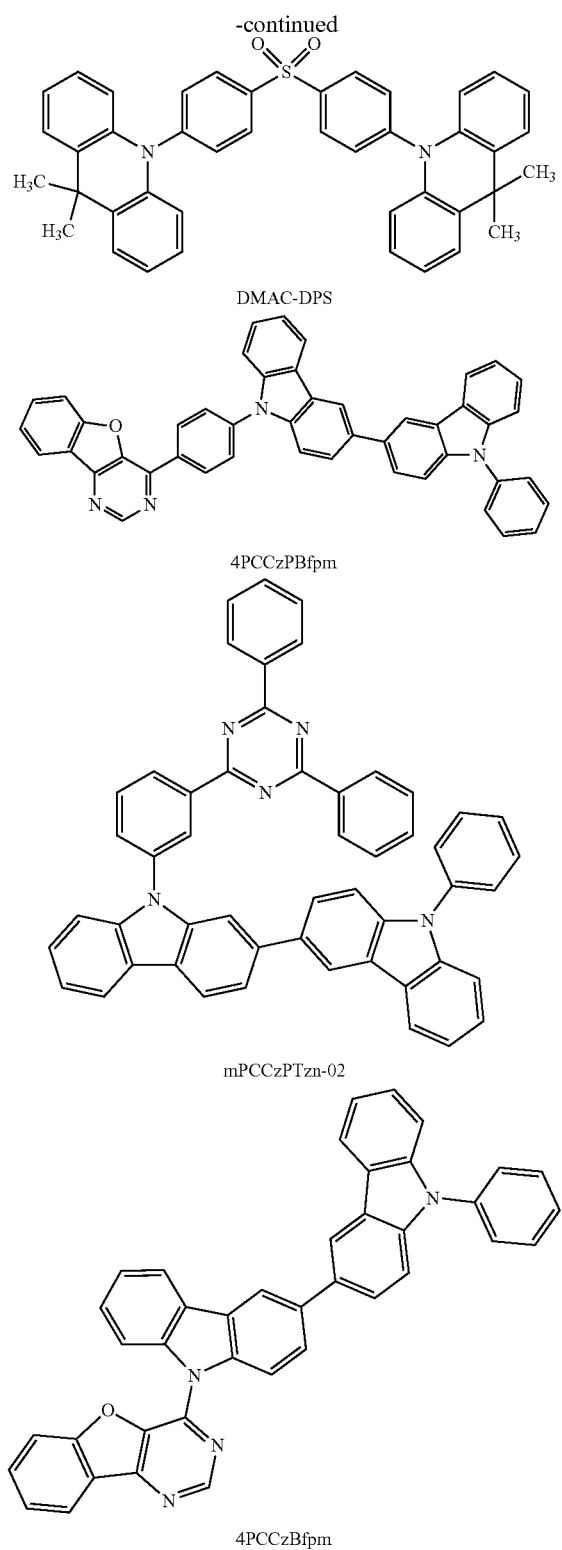

DMAC-DPS

4PCCzPBfpm mPCCzPTzn-02

4PCCzBfpm

Such a heterocyclic aromatic compound is preferred because of having excellent electron-transport and hole-transport properties owing to a π-electron rich heteroaromatic ring and a π-electron deficient heteroaromatic ring. Among skeletons having the π-electron deficient heteroaromatic ring, a pyridine skeleton, a diazine skeleton (a pyrimidine skeleton, a pyrazine skeleton, and a pyridazine skeleton), and a triazine skeleton are preferred because of their high stability and reliability. In particular, a benzofuropyrimidine skeleton, a benzothienopyrimidine skeleton, a benzofuropyrazine skeleton, and a benzothienopyrazine skeleton are preferred because of their high accepting properties and reliability.

Among skeletons having the π-electron rich heteroaromatic ring, an acridine skeleton, a phenoxazine skeleton, a phenothiazine skeleton, a furan skeleton, a thiophene skeleton, and a pyrrole skeleton have high stability and reliability; therefore, at least one of these skeletons is preferably included. As a furan skeleton, a dibenzofuran skeleton is preferable. As a thiophene skeleton, a dibenzothiophene skeleton is preferable. As a pyrrole skeleton, an indole skeleton, a carbazole skeleton, an indolocarbazole skeleton, a bicarbazole skeleton, and a 3-(9-phenyl-9H-carbazol-3-yl)-9H-carbazole skeleton are particularly preferable.

Note that a substance in which the π-electron rich heteroaromatic ring is directly bonded to the π-electron deficient heteroaromatic ring is particularly preferred because the electron-donating property of the π-electron rich heteroaromatic ring and the electron-accepting property of the π-electron deficient heteroaromatic ring are both improved, the energy difference between the S1 level and the T1 level becomes small, and thus thermally activated delayed fluorescence can be obtained with high efficiency. Note that an aromatic ring to which an electron-withdrawing group such as a cyano group is bonded may be used instead of the π-electron deficient heteroaromatic ring. As a π-electron rich skeleton, an aromatic amine skeleton, a phenazine skeleton, or the like can be used. As a π-electron deficient skeleton, a xanthene skeleton, a thioxanthene dioxide skeleton, an oxadiazole skeleton, a triazole skeleton, an imidazole skeleton, an anthraquinone skeleton, a skeleton containing boron such as phenylborane or boranthrene, an aromatic ring or a heteroaromatic ring having a cyano group or a nitrile group such as benzonitrile or cyanobenzene, a carbonyl skeleton such as benzophenone, a phosphine oxide skeleton, a sulfone skeleton, or the like can be used.

As described above, a π-electron deficient skeleton and a π-electron rich skeleton can be used instead of at least one of the π-electron deficient heteroaromatic ring and the π-electron rich heteroaromatic ring.

Note that a TADF material is a material having a small difference between the S1 level and the T1 level and a function of converting triplet excitation energy into singlet excitation energy by reverse intersystem crossing. Thus, a TADF material can upconvert triplet excitation energy into singlet excitation energy (i.e., reverse intersystem crossing) using a small amount of thermal energy and efficiently generate a singlet excited state. In addition, the triplet excitation energy can be converted into luminescence.

An exciplex whose excited state is formed of two kinds of substances has an extremely small difference between the S1 level and the T1 level and has the same function as a TADF material capable of converting triplet excitation energy into singlet excitation energy.

A phosphorescent spectrum observed at a low temperature (e.g., 77 K to 10 K) is used for an index of the T1 level. The TADF material preferably has a difference between the S1 level and the T1 level of 0.3 eV or smaller, further preferably 0.2 eV or smaller, where the S1 level is the energy of a wavelength at the intersection of the x-axis and a tangent drawn to a tail on the short wavelength side of the fluorescent spectrum, and the T1 level is the energy of a wavelength at the intersection of the x-axis and a tangent drawn to a tail on the short wavelength side of the phosphorescent spectrum.

When the TADF material is used as the guest material in the light-emitting layer 113, the S1 level and the T1 level of the host material are preferably higher than the S1 level and the T1 level of the TADF material, respectively.

As the hole-transport material that can be used as the host material in the light-emitting layer 113, it is preferable to use a substance having a hole mobility higher than or equal to $1 \times 10^{-6}$ cm/Vs in the case where the square root of the electric field strength [V/cm] is 600. Examples of the substance are shown below.

Examples of the substance include compounds having an aromatic amine skeleton such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), and N-phenyl-N-[4-(9-phenyl-9H-carbazol-3-yl)phenyl]spiro-9,9'-bifluoren-2-amine (abbreviation: PCBASF); compounds having a carbazole skeleton such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), and 3,3'-bis(9-phenyl-9H-carbazole) (abbreviation: PCCP); compounds having a thiophene skeleton such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having a furan skeleton such as 4,4',4"-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II). Among the above materials, the compound having an aromatic amine skeleton and the compound having a carbazole skeleton are preferred because these compounds are highly reliable and have high hole-transport properties to contribute to a reduction in driving voltage. In addition, the organic compounds given as examples of the above hole-transport material can also be used.

As the electron-transport material that can be used as the host material in the light-emitting layer 113, it is preferable to use a substance having an electron mobility higher than or equal to $1 \times 10^{-6}$ cm$^2$/Vs in the case where the square root of the electric field strength [V/cm] is 600. Examples of the substance are shown below. In addition, an electron-transport material that can be used in the electron-transport layer 114, which is described later, can also be used.

Examples of the electron-transport material include metal complexes such as bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds having a polyazole skeleton, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2"-(1,3,5-benzenetriyl)tris(1-phenyl-1H-benzimidazole) (abbreviation: TPBI), and 2-[3-(dibenzothiophen-4-yl)phenyl]-1-phenyl-1H-benzimidazole (abbreviation: mDBTBIm-II); heteroaryl compounds having a diazine skeleton, such as 2-[3-(dibenzothiophen-4-yl)phenyl]dibenzo[fh]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 4,4'-(2,3-dicyanodibenzo[f,h]quinoxaline-7,10-diyl)bis(triphenylamine) (abbreviation: 2,3CN-7,10TPA2DBq), 4,6-bis[3-(phenanthren-9-yl)phenyl]pyrimidine (abbreviation: 4,6mPnP2Pm), and 4,6-bis[3-(4-dibenzothienyl)phenyl]pyrimidine (abbreviation: 4,6mDBTP2Pm-II); and heteroaryl compounds having a pyridine skeleton, such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB). Among the above materials, the heteroaryl compound having a diazine skeleton and the heteroaryl compound having a pyridine skeleton have high reliability and thus are preferable. In particular, the heteroaryl compound having a diazine (pyrimidine or pyrazine) skeleton has an excellent electron-transport property to contribute to a reduction in driving voltage.

In the case where the TADF material is used as the host material in the light-emitting layer 113, the above-described materials can also be used. When the TADF material is used as the host material, triplet excitation energy generated in the TADF material is converted into singlet excitation energy by reverse intersystem crossing and transferred to the emission center substance, whereby the emission efficiency of the light-emitting device can be increased. Here, the TADF material functions as an energy donor, and the emission center substance functions as an energy acceptor. Therefore, the use of the TADF material as the host material is very effective in the case where a fluorescent substance is used as the guest material. In that case, it is preferable that the S1 level of the TADF material be higher than the S1 level of the fluorescent substance in order that high emission efficiency be achieved. Furthermore, the T1 level of the TADF material is preferably higher than the S1 level of the fluorescent substance. Therefore, the T1 level of the TADF material is preferably higher than the T1 level of the fluorescent substance.

A TADF material that emits light whose wavelength overlaps with the a lowest-energy-side absorption band of the fluorescent substance is preferably used, in which case excitation energy is transferred smoothly from the TADF material to the fluorescent substance and light emission can be obtained efficiently.

In addition, in order to efficiently generate singlet excitation energy from the triplet excitation energy by reverse intersystem crossing, carrier recombination preferably occurs in the TADF material. It is also preferable that the triplet excitation energy generated in the TADF material not be transferred to the triplet excitation energy of the fluorescent substance. For that reason, the fluorescent substance preferably has a protective group around a luminophore (a skeleton which causes light emission) of the fluorescent substance. As the protective group, a substituent having no π bond and a saturated hydrocarbon are preferably used. Specific examples include an alkyl group having 3 to 10 carbon atoms, a substituted or unsubstituted cycloalkyl group having 3 to 10 carbon atoms in a ring, and a trialkylsilyl group having 3 to 10 carbon atoms. It is further preferable that the fluorescent substance have a plurality of protective groups. The substituents having no π bond are poor in carrier transport performance, whereby the TADF material and the luminophore of the fluorescent substance can be made away from each other with little influence on carrier transportation or carrier recombination. Here, the luminophore refers to an atomic group (skeleton) that causes light emission in a fluorescent substance. The luminophore is preferably a skeleton having a π bond, further preferably includes an aromatic ring, and still further preferably includes a condensed aromatic ring or a condensed heteroaromatic ring. Examples of the condensed aromatic ring or the condensed heteroaromatic ring include a phenanthrene skeleton, a stilbene skeleton, an acridone skeleton, a phenoxazine skeleton, and a phenothiazine skeleton. Specifically, a fluorescent substance having any of a naphthalene skeleton, an anthracene skeleton, a fluorene skeleton, a chrysene skeleton, a triphenylene skeleton, a tetracene skeleton, a pyrene skeleton, a perylene skeleton, a coumarin skeleton, a quinacridone skeleton, and a naphthobisbenzofuran skeleton is preferred because of its high fluorescence quantum yield.

In the case where a fluorescent substance is used as the guest material in the light-emitting layer 113, a material having an anthracene skeleton is favorably used as the host material. The use of a substance having an anthracene skeleton makes it possible to obtain a light-emitting layer with high emission efficiency and high durability. Among the substances having an anthracene skeleton, a substance having a diphenylanthracene skeleton, in particular, a substance having a 9,10-diphenylanthracene skeleton, is chemically stable and thus is preferable.

The host material preferably has a carbazole skeleton because the hole-injection and hole-transport properties are improved; further preferably, the host material has a benzocarbazole skeleton in which a benzene ring is further condensed to carbazole because the HOMO level thereof is shallower than that of carbazole by approximately 0.1 eV and thus holes enter the host material easily. In particular, the host material preferably has a dibenzocarbazole skeleton because the HOMO level thereof is shallower than that of carbazole by approximately 0.1 eV so that holes enter the host material easily, the hole-transport property is improved, and the heat resistance is increased.

Thus, a substance having both of a 9,10-diphenylanthracene skeleton, which is an anthracene skeleton, and a carbazole skeleton (or a benzocarbazole skeleton or a dibenzocarbazole skeleton) is further preferable as the host material. Note that in terms of an improvement in the hole-injection and hole-transport properties described above, instead of a carbazole skeleton, a benzofluorene skeleton or a dibenzo fluorene skeleton may be used. Examples of such a substance include 9-phenyl-3-[4-(10-phenyl-9-anthryl) phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d] furan (abbreviation: 2mBnfPPA), 9-phenyl-10-{4-(9-phenyl-9H-fluoren-9-yl)biphenyl-4'-yl}anthracene (abbreviation: FLPPA), and 9-(1-naphthyl)-10-[4-(2-naphthyl)phenyl]anthracene (abbreviation: BH513). Note that CzPA, cgDBCzPA, 2mBnfPPA, and PCzPA have excellent characteristics and thus are preferable.

Note that the host material may be a mixture of a plurality of kinds of substances; in the case of using a mixed host material, it is preferable to mix an electron-transport material with a hole-transport material. By mixing the electron-transport material with the hole-transport material, the transport property of the light-emitting layer 113 can be easily adjusted and a recombination region can be easily controlled. The weight ratio of the content of the hole-transport material to the content of the electron-transport material may be 1:19 to 19:1.

Note that a phosphorescent substance can be used as part of the host material in the case where the host material is formed by mixing a plurality of kinds of substances as described above. When a fluorescent substance is used as the emission center substance, a phosphorescent substance can be used as an energy donor for supplying excitation energy to the fluorescent substance.

An exciplex may be formed of these mixed materials. When these mixed materials are selected so as to form an exciplex that exhibits light emission whose wavelength overlaps with a lowest-energy-side absorption band of the light-emitting substance, energy can be transferred smoothly and light emission can be obtained efficiently. The use of such a structure is preferred because the driving voltage can be reduced.

Note that at least one of the materials forming an exciplex may be a phosphorescent substance. In this case, triplet excitation energy can be efficiently converted into singlet excitation energy by reverse intersystem crossing.

Combination of an electron-transport material and a hole-transport material whose HOMO level is higher than or equal to that of the electron-transport material is preferable for forming an exciplex. In addition, the LUMO level of the hole-transport material is preferably higher than or equal to that of the electron-transport material. Note that the LUMO levels and the HOMO levels of the materials can be derived from the electrochemical characteristics (the reduction potentials and the oxidation potentials) of the materials that are measured by cyclic voltammetry (CV).

The formation of an exciplex can be confirmed by a phenomenon in which the emission spectrum of the mixed film in which the hole-transport material and the electron-transport material are mixed is shifted to the longer wavelength side than the emission spectra of each of the materials (or has another peak on the longer wavelength side) observed by comparison of the emission spectra of the hole-transport material, the electron-transport material, and the mixed film of these materials, for example. Alternatively, the formation of an exciplex can be confirmed by a difference in transient response, such as a phenomenon in which the transient PL lifetime of the mixed film has more long lifetime components or has a larger proportion of delayed components than that of each of the materials, observed by comparison of transient photoluminescence (PL) of the hole-transport material, the electron-transport material, and the mixed film of the materials. The transient PL can be rephrased as transient electroluminescence (EL). That is, the formation of an exciplex can also be confirmed by a difference in transient response observed by comparison of the transient EL of the hole-transport material, the electron-transport material, and the mixed film of the materials.

<Electron-Transport Layer>

The electron-transport layer 114 transfers electrons injected from the second electrode 102 to the light-emitting layer 113 and is in contact with the light-emitting layer 113. Note that the electron-transport layer 114 contains an electron-transport material. It is preferable that the electron-transport material contained in the electron-transport layer 114 be a substance with an electron mobility of higher than or equal to $1\times10^{-6}$ cm$^2$/Vs. Note that any other substance can also be used as long as the substance transports electrons more easily than it transports holes. An electron-transport material and an organometallic complex that is an alkali metal or an alkaline earth metal may be used for the electron-transport layer 114. In that case, an electron-transport material having a HOMO level higher than or equal to −6.0 eV is preferably used as the electron-transport material. The electron mobility of the electron-transport material with a HOMO level higher than or equal to −6.0 eV is preferably higher than or equal to $1\times10^{-7}$ cm$^2$/Vs and lower than or equal to $1\times10^{-5}$ cm$^2$, further preferably higher than or equal to $1\times10^{-7}$ cm$^2$/Vs and lower than or equal to $5\times10^{-5}$ cm$^2$ in the case where the square root of the electric field strength [V/cm] is 600.

As the electron-transport material with a HOMO level higher than or equal to −6.0 eV, an organic compound having an anthracene skeleton, an organic compound having an anthracene skeleton and a heterocyclic skeleton, or the like is preferably used. Therefore, the quinoxaline derivative of one embodiment of the present invention is preferably used as the electron-transport material. In addition, some of the above-described electron-transport materials that can be used as the host material, or the above-described materials given as materials that can be used as the host material in combination with the above-described fluorescent substance can be used in the electron-transport layer 114.

The organic metal complex of an alkali metal or an alkaline earth metal is preferably an organic complex of lithium or sodium, and particularly preferably 8-quinolinolato-lithium (abbreviation: Liq).

Furthermore, the electron mobility of the electron-transport material with a HOMO level higher than or equal to −6.0 eV that is used for the electron-transport layer 114 in the case where the square root of the electric field strength [V/cm] is 600 is preferably lower than the electron mobility of the host material in the light-emitting layer 113. The amount of electrons injected into the light-emitting layer can be controlled by the reduction in the electron-transport property of the electron-transport layer, whereby the light-emitting layer can be prevented from having excess electrons.

In the case where the electron-transport layer 114 includes an organic metal complex of an alkali metal or an alkaline earth metal, the electron-transport layer 114 may be formed of two or more layers with different amounts of the organic metal complex; it is particularly preferable that the amount of the organic metal complex be large at an interface with the light-emitting layer.

<Electron-Injection Layer>

The electron-injection layer 115 is a layer for increasing the efficiency of electron injection from the second electrode 102 and is preferably formed using a material whose value of the LUMO level has a small difference (0.5 eV or less) from the work function of a material of the second electrode 102. Thus, the electron-injection layer 115 can be formed using an alkali metal, an alkaline earth metal, or a compound thereof, such as lithium, cesium, lithium fluoride (LiF), cesium fluoride (CsF), calcium fluoride (CaF$_2$), 8-quinolinolato-lithium (abbreviation: Liq), 2-(2-pyridyl)phenolato-lithium (abbreviation: LiPP), 2-(2-pyridyl)-3-pyridinolato lithium (abbreviation: LiPPy), 4-phenyl-2-(2-pyridyl)phenolato lithium (abbreviation: LiPPP), lithium oxide (LiO$_x$), or cesium carbonate. A rare earth metal compound like erbium fluoride (ErF$_3$) can also be used.

When a charge-generation layer 104 is provided between two EL layers 103a and 103b as in the light-emitting device in FIG. 1B, a structure in which a plurality of EL layers are stacked between the pair of electrodes (the structure is also referred to as a tandem structure) can be obtained. Note that in this embodiment, functions and materials of the hole-injection layer 111, the hole-transport layer 112, the light-emitting layer 113, the electron-transport layer 114, and the electron-injection layer 115 that are illustrated in FIG. 1A are the same as those of hole-injection layers 111a and 111b, hole-transport layers 112a and 112b, light-emitting layers 113a and 113b, electron-transport layers 114a and 114b, and electron-injection layers 115a and 115b that are illustrated in FIG. 1B.

<Charge-Generation Layer>

In the light-emitting device in FIG. 1B, the charge-generation layer 104 has a function of injecting electrons into the EL layer 103a on the first electrode 101 (anode) side and injecting holes into the EL layer 103b on the second electrode 102 (cathode) side when a voltage is applied between the first electrode (anode) 101 and the second electrode (cathode) 102. The charge-generation layer 104 may be either a p-type layer in which an electron acceptor (acceptor) is added to a hole-transport material or an n-type layer in which an electron donor (donor) is added to an electron-transport material. Alternatively, both of these layers may be stacked. Alternatively, the p-type layer and either one or both of an electron-relay layer and an electron-injection buffer layer, which are described later, may be combined. Note that forming the charge-generation layer 104 with the use of any of the above materials can inhibit an increase in driving voltage caused by the stack of the EL layers.

In the case where the charge-generation layer 104 is a p-type layer in which an electron acceptor is added to a hole-transport material, any of the materials described in this embodiment can be used as the hole-transport material. As the electron acceptor, it is possible to use 7,7,8,8-tetracyano-2,3,5,6-tetrafluoroquinodimethane (abbreviation: F4-TCNQ), chloranil, and the like. Other examples include oxides of metals that belong to Group 4 to Group 8 of the periodic table. Specific examples are vanadium oxide, niobium oxide, tantalum oxide, chromium oxide, molybdenum oxide, tungsten oxide, manganese oxide, and rhenium oxide.

In the case where the charge-generation layer 104 is an n-type layer in which an electron donor is added to an electron-transport material, any of the materials described in this embodiment can be used as the electron-transport material. As the electron donor, it is possible to use an alkali metal, an alkaline earth metal, a rare earth metal, metals that belong to Group 2 and Group 13 of the periodic table, or an oxide or carbonate thereof. Specifically, lithium (Li), cesium (Cs), magnesium (Mg), calcium (Ca), ytterbium (Yb), indium (In), lithium oxide, cesium carbonate, or the like is preferably used. An organic compound such as tetrathianaphthacene may be used as the electron donor.

When the electron-relay layer which is preferably combined with the p-type layer as described above is provided between the electron-injection buffer layer and the p-type layer, the electron-relay layer has a function of preventing an interaction between the electron-injection buffer layer and the p-type layer and smoothly transferring electrons. The electron-relay layer includes at least an electron-transport material, and the LUMO level of the electron-transport material is preferably between the LUMO level of the electron-accepting substance in the p-type layer and the LUMO level of a substance in the electron-injection buffer layer. Specifically, the LUMO level of the electron-transport material in the electron-relay layer is preferably higher than or equal to −5.0 eV, further preferably higher than or equal to −5.0 eV and lower than or equal to −3.0 eV Note that as the electron-transport material in the electron-relay layer, a phthalocyanine-based material or a metal complex having a metal-oxygen bond and an aromatic ligand is preferably used.

A substance having an excellent electron-injection property can be used for the electron-injection buffer layer. For example, an alkali metal, an alkaline earth metal, a rare earth metal, or a compound thereof (an alkali metal compound (including an oxide such as lithium oxide, a halide, and a carbonate such as lithium carbonate and cesium carbonate), an alkaline earth metal compound (including an oxide, a halide, and a carbonate), or a rare earth metal compound (including an oxide, a halide, and a carbonate)) can be used.

In the case where the electron-injection buffer layer includes the electron-transport material and an electron-donating substance, an organic compound such as tetrathianaphthacene (abbreviation: TTN), nickelocene, or decamethylnickelocene can be used as the electron-donating substance, as well as an alkali metal, an alkaline earth metal, a rare earth metal, a compound thereof (an alkali metal compound (including an oxide such as lithium oxide, a halide, and a carbonate such as lithium carbonate and cesium carbonate), an alkaline earth metal compound (including an oxide, a halide, and a carbonate), or a rare earth metal compound (including an oxide, a halide, and a carbonate)). As the electron-transport material, a material similar to the above-described material for the electron-transport layer can be used.

Although FIG. 1B illustrates the structure of the light-emitting device in which two EL layers 103 are stacked, three or more EL layers may be stacked with charge-generation layers each provided between two adjacent EL layers.

The above-described charge-generation layer can be used instead of the above-described electron-injection layer. In that case, the electron-injection buffer layer, the electron-relay layer, and the p-type layer are preferably stacked in this order from the anode side.

<Substrate>

The light-emitting device described in this embodiment can be formed over any of a variety of substrates. Note that the type of substrate is not limited to a certain type. Examples of the substrate include semiconductor substrates (e.g., a single crystal substrate and a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, and a base material film.

Examples of the glass substrate include a barium borosilicate glass substrate, an aluminoborosilicate glass substrate, and a soda lime glass substrate. Examples of the flexible substrate, the attachment film, and the base material film include plastics typified by polyethylene terephthalate (PET), polyethylene naphthalate (PEN), and polyether sulfone (PES); a synthetic resin such as an acrylic resin; polypropylene; polyester; polyvinyl fluoride; polyvinyl chloride; polyamide; polyimide; an aramid resin; an epoxy resin; an inorganic vapor deposition film; and paper.

For fabrication of the light-emitting device in this embodiment, a vacuum process such as an evaporation method or a solution process such as a spin coating method or an ink-jet method can be used. When an evaporation method is used, a physical vapor deposition method (PVD method) such as a sputtering method, an ion plating method, an ion beam evaporation method, a molecular beam evaporation method, or a vacuum evaporation method, a chemical vapor deposition method (CVD method), or the like can be used. Specifically, the functional layers included in the EL layers (the hole-injection layers 111, 11a, and 111b, the hole-transport layers 112, 112a, and 112b, the light-emitting layers 113, 113a, and 113b, the electron-transport layers 114, 114a, and 114b, and the electron-injection layers 115, 115a, and 115b) and the charge-generation layer 104 of the light-emitting device can be formed by an evaporation method (e.g., a vacuum evaporation method), a coating method (e.g., a dip coating method, a die coating method, a bar coating method, a spin coating method, or a spray coating method), a printing method (e.g., an ink-jet method, screen printing (stencil), offset printing (planography), flexography (relief printing), gravure printing, micro-contact printing, or nano-imprint lithography), or the like.

Note that materials that can be used for the functional layers included in the EL layers 103, 103a, and 103b (the hole-injection layers 111, 11a, and 111b, the hole-transport layers 112, 112a, and 112b, the light-emitting layers 113, 113a, and 113b, the electron-transport layers 114, 114a, and 114b, and the electron-injection layers 115, 115a, and 115b) and the charge-generation layer 104 of the light-emitting device described in this embodiment are not limited to the above materials, and other materials can be used in combination as long as the functions of the layers are fulfilled. For example, a high-molecular compound (e.g., an oligomer, a dendrimer, and a polymer), a middle molecular compound (a compound between a low molecular compound and a high-molecular compound with a molecular weight of 400 to 4000), or an inorganic compound (e.g., a quantum dot material) can be used. The quantum dot material may be a colloidal quantum dot material, an alloyed quantum dot material, a core-shell quantum dot material, a core quantum dot material, or the like.

With the above-described structure where the organic compound of one embodiment of the present invention is used in an EL layer (specifically, a light-emitting layer), a novel light-emitting device having an emission spectrum peak in a region with wavelengths longer than 850 nm and an absorption spectrum peak in a region with wavelengths longer than 600 nm can be formed. Furthermore, using the organic compound of one embodiment of the present invention in an active layer of a light-receiving device allows the light-receiving device to be a sensor which senses light of the red to near-infrared region (light having an emission spectrum peak in a region with wavelengths longer than 850 nm).

The structures described in this embodiment can be used in combination with any of the structures described in the other embodiments, as appropriate.

Embodiment 3

Figure 2A:
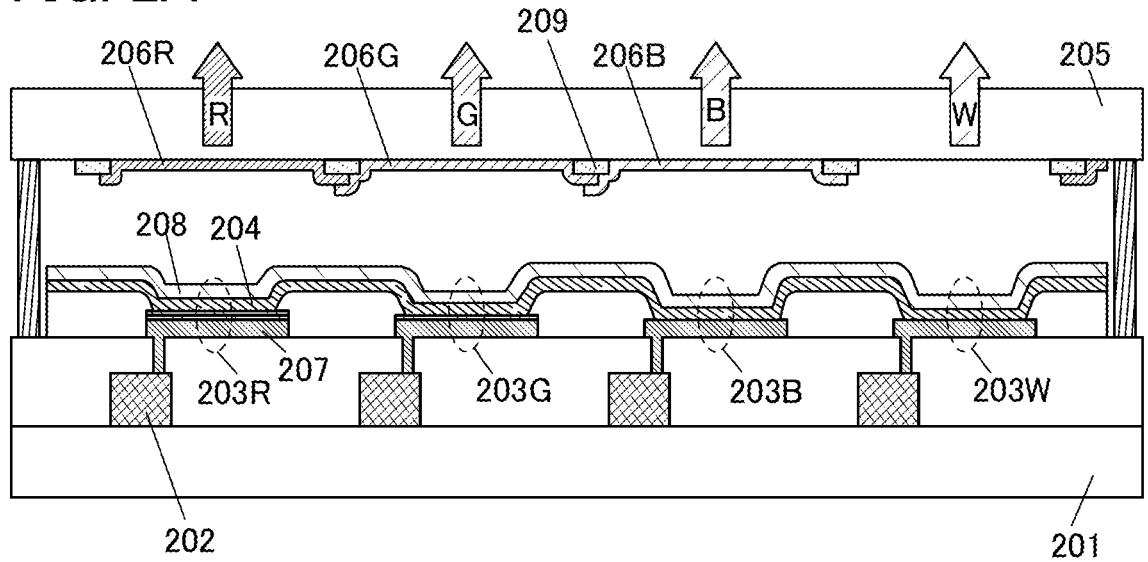
FIGS. 2A to 2C are each a view illustrating a light-emitting apparatus.

In this embodiment, light-emitting apparatuses according to one embodiment of the present invention will be described. Note that a light-emitting apparatus illustrated in FIG. 2A is an active-matrix light-emitting apparatus in which transistors (FETs) 202 over a first substrate 201 are electrically connected to light-emitting devices (203R, 203G, 203B, and 203W). The light-emitting devices (203R, 203G, 203B, and 203W) include a common EL layer 204 and have a microcavity structure in which the optical path length between electrodes is adjusted according to the emission color of the light-emitting device. The light-emitting apparatus is a top-emission light-emitting apparatus in which light is emitted from the EL layer 204 through color filters (206R, 206G, and 206B) formed on a second substrate 205.

The light-emitting apparatus illustrated in FIG. 2A is fabricated such that a first electrode 207 functions as a reflective electrode and a second electrode 208 functions as a transflective electrode. Note that description in any of the other embodiments can be referred to as appropriate for electrode materials for the first electrode 207 and the second electrode 208.

Figure 2B:
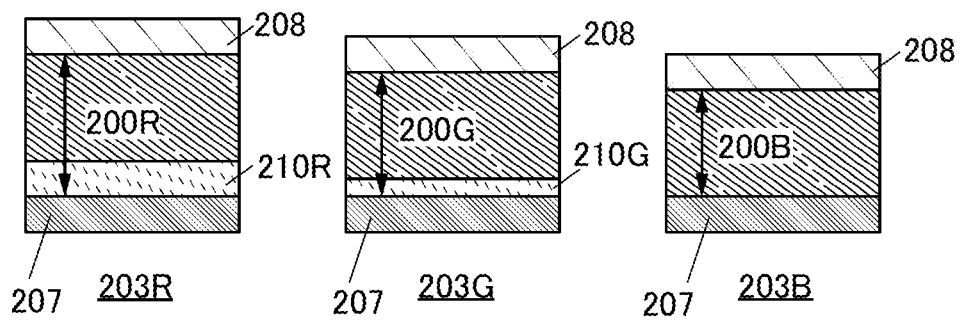

In the case where the light-emitting device 203R functions as a red light-emitting device, the light-emitting device 203G functions as a green light-emitting device, the light-emitting device 203B functions as a blue light-emitting device, and the light-emitting device 203W functions as a white light-emitting device in FIG. 2A, for example, a gap between the first electrode 207 and the second electrode 208 in the light-emitting device 203R is adjusted to have an optical path length 200R, a gap between the first electrode 207 and the second electrode 208 in the light-emitting device 203G is adjusted to have an optical path length 200G, and a gap between the first electrode 207 and the second electrode 208 in the light-emitting device 203B is adjusted to have an optical path length 200B as illustrated in FIG. 2B. Note that optical adjustment can be performed in such a manner that a conductive layer 210R is stacked over the first electrode 207 in the light-emitting device 203R and a conductive layer 210G is stacked over the first electrode 207 in the light-emitting device 203G as illustrated in FIG. 2B.

The second substrate 205 is provided with the color filters (206R, 206G, and 206B). Note that the color filters each transmit visible light in a specific wavelength range and blocks visible light in a specific wavelength range. Thus, as illustrated in FIG. 2A, the color filter 206R that transmits only light in the red wavelength range is provided in a position overlapping with the light-emitting device 203R, whereby red light emission can be obtained from the light-emitting device 203R. Furthermore, the color filter 206G that transmits only light in the green wavelength range is provided in a position overlapping with the light-emitting device 203G, whereby green light emission can be obtained from the light-emitting device 203G. Moreover, the color filter 206B that transmits only light in the blue wavelength range is provided in a position overlapping with the light-emitting device 203B, whereby blue light emission can be obtained from the light-emitting device 203B. Note that the light-emitting device 203W can emit white light without a color filter. Note that a black layer (black matrix) 209 may be provided at an end portion of each color filter. The color filters (206R, 206G, and 206B) and the black layer 209 may be covered with an overcoat layer formed using a transparent material.

Figure 2C:
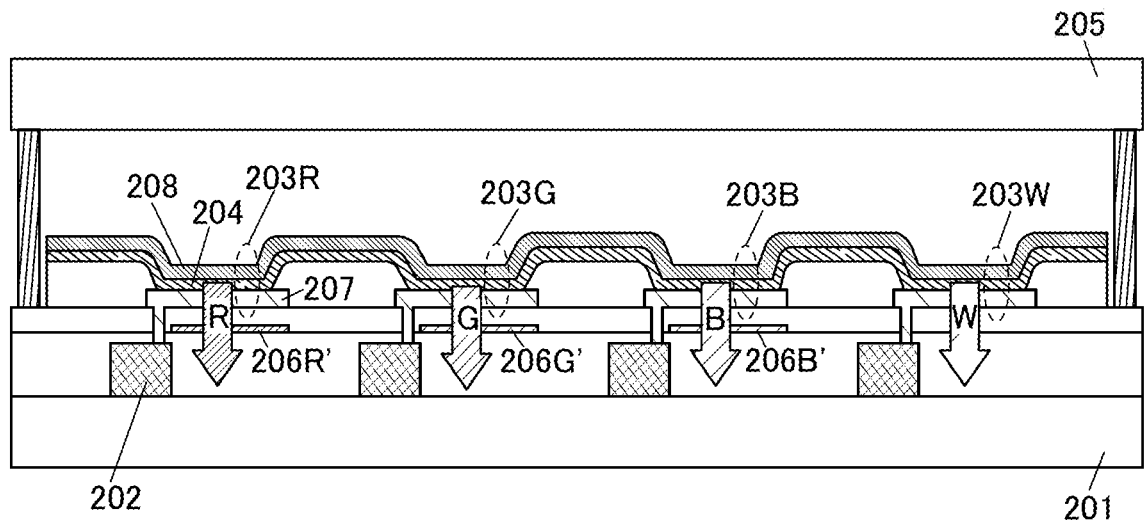

Although the light-emitting apparatus in FIG. 2A has a structure in which light is extracted from the second substrate 205 side (top emission structure), a structure in which light is extracted from the first substrate 201 side where the FETs 202 are formed (bottom emission structure) may be employed as illustrated in FIG. 2C. In the case of a bottom-emission light-emitting apparatus, the first electrode 207 is formed as a transflective electrode and the second electrode 208 is formed as a reflective electrode. As the first substrate 201, a substrate having at least a light-transmitting property is used. As illustrated in FIG. 2C, color filters (206R', 206G', and 206B') are provided closer to the first substrate 201 than the light-emitting devices (203R, 203G, and 203B) are.

In FIG. 2A, the light-emitting devices are the red light-emitting device, the green light-emitting device, the blue light-emitting device, and the white light-emitting device; however, the light-emitting devices of one embodiment of the present invention are not limited to the above, and a yellow light-emitting device or an orange light-emitting device may be used. Note that description in any of the other embodiments can be referred to as appropriate for materials that are used for the EL layers (a light-emitting layer, a hole-injection layer, a hole-transport layer, an electron-transport layer, an electron-injection layer, a charge-generation layer, and the like) to fabricate each of the light-emitting devices. In that case, a color filter needs to be appropriately selected according to the emission color of the light-emitting device.

With the above structure, a light-emitting apparatus including light-emitting devices that exhibit a plurality of emission colors can be fabricated.

The structures described in this embodiment can be used in combination with any of the structures described in the other embodiments, as appropriate.

Embodiment 4

In this embodiment, a light-emitting apparatus of one embodiment of the present invention will be described.

The use of the device structure of the light-emitting device of one embodiment of the present invention allows fabrication of an active-matrix light-emitting apparatus or a passive-matrix light-emitting apparatus. Note that an active-matrix light-emitting apparatus has a structure including a combination of a light-emitting device and a transistor (FET). Thus, each of a passive-matrix light-emitting apparatus and an active-matrix light-emitting apparatus is one embodiment of the present invention. Note that any of the light-emitting devices described in other embodiments can be used in the light-emitting apparatus described in this embodiment.

In this embodiment, an active-matrix light-emitting apparatus will be described with reference to FIGS. 3A and 3B.

Figure 3A:
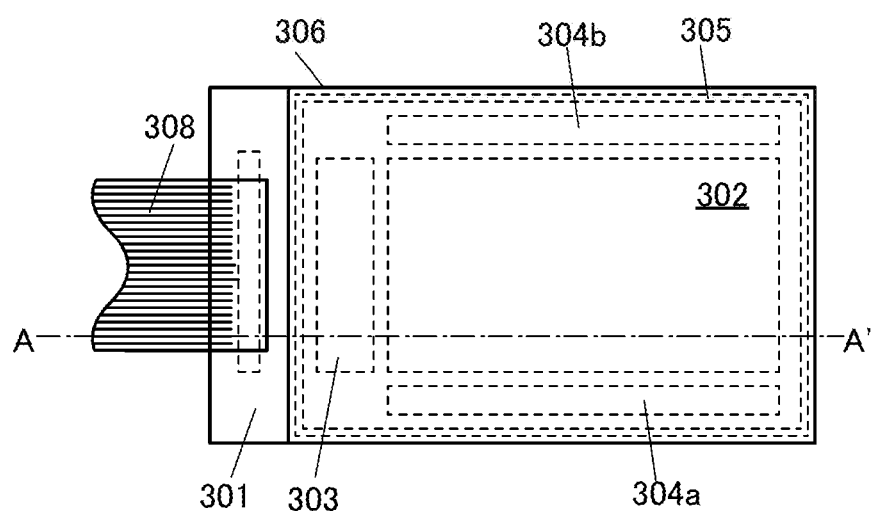
FIGS. 3A and 3B are a top view and a cross-sectional view of a light-emitting apparatus, respectively.
Figure 3B:
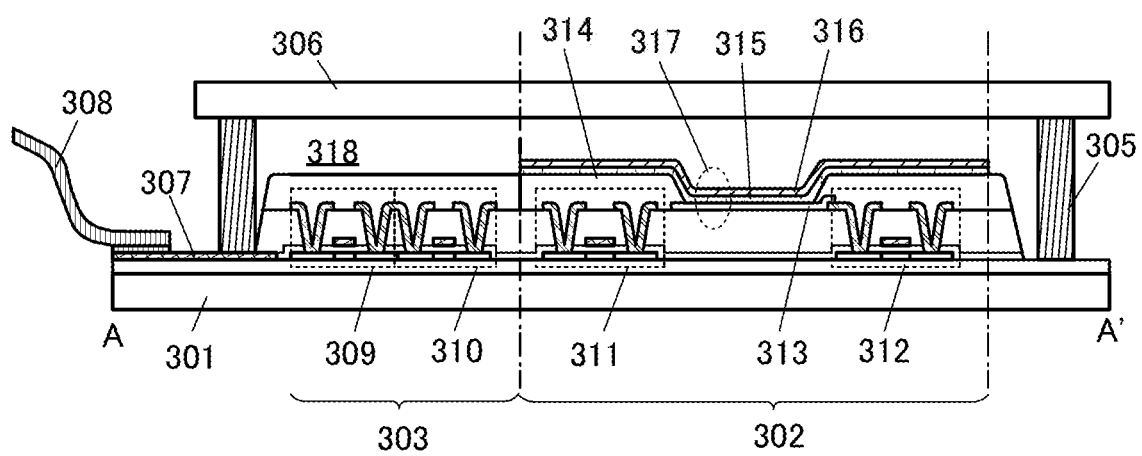

FIG. 3A is a top view illustrating the light-emitting apparatus, and FIG. 3B is a cross-sectional view taken along chain line A-A' in FIG. 3A. The active-matrix light-emitting apparatus includes a pixel portion 302, a driver circuit portion (source line driver circuit) 303, and driver circuit portions (gate line driver circuits) (304a and 304b) that are provided over a first substrate 301. The pixel portion 302 and the driver circuit portions (303, 304a, and 304b) are sealed between the first substrate 301 and a second substrate 306 with a sealant 305.

A lead wiring 307 is provided over the first substrate 301. The lead wiring 307 is electrically connected to an FPC 308 that is an external input terminal. Note that the FPC 308 transmits a signal (e.g., a video signal, a clock signal, a start signal, or a reset signal) or a potential from the outside to the driver circuit portions (303, 304a, and 304b). The FPC 308 may be provided with a printed wiring board (PWB). Note that the light-emitting apparatus provided with an FPC or a PWB is included in the category of a light-emitting apparatus.

FIG. 3B illustrates a cross-sectional structure of the light-emitting apparatus.

The pixel portion 302 includes a plurality of pixels each of which includes an FET (switching FET) 311, an FET (current control FET) 312, and a first electrode 313 electrically connected to the FET 312. Note that the number of FETs included in each pixel is not particularly limited and can be set appropriately.

As FETs 309, 310, 311, and 312, for example, a staggered transistor or an inverted staggered transistor can be used without particular limitation. A top-gate transistor, a bottom-gate transistor, or the like may be used.

Note that there is no particular limitation on the crystallinity of a semiconductor that can be used for the FETs 309, 310, 311, and 312, and an amorphous semiconductor or a semiconductor having crystallinity (a microcrystalline semiconductor, a polycrystalline semiconductor, a single crystal semiconductor, or a semiconductor partly including crystal regions) may be used. A semiconductor having crystallinity is preferably used, in which case deterioration of the transistor characteristics can be inhibited.

For the semiconductor, a Group 14 element, a compound semiconductor, an oxide semiconductor, an organic semiconductor, or the like can be used, for example. As a typical example, a semiconductor containing silicon, a semiconductor containing gallium arsenide, or an oxide semiconductor containing indium can be used.

The driver circuit portion 303 includes the FET 309 and the FET 310. The driver circuit portion 303 may be formed with a circuit including transistors having the same conductivity type (either n-channel transistors or p-channel transistors) or a CMOS circuit including an n-channel transistor and a p-channel transistor. Furthermore, a driver circuit may be provided outside.

An end portion of the first electrode 313 is covered with an insulator 314. The insulator 314 can be formed using an organic compound such as a negative photosensitive resin or a positive photosensitive resin (acrylic resin), or an inorganic compound such as silicon oxide, silicon oxynitride, or silicon nitride. The insulator 314 preferably has a curved surface with curvature at an upper end portion or a lower end portion thereof. In that case, favorable coverage with a film formed over the insulator 314 can be obtained.

An EL layer 315 and a second electrode 316 are stacked over the first electrode 313. The EL layer 315 includes a light-emitting layer, a hole-injection layer, a hole-transport layer, an electron-transport layer, an electron-injection layer, a charge-generation layer, and the like.

The structure and materials described in any of the other embodiments can be used for the components of a light-emitting device 317 described in this embodiment. Although not illustrated, the second electrode 316 is electrically connected to the FPC 308 that is an external input terminal.

Although the cross-sectional view in FIG. 3B illustrates only one light-emitting device 317, a plurality of light-emitting devices are arranged in a matrix in the pixel portion 302. Light-emitting devices that emit light of three kinds of colors (R, G, and B) are selectively formed in the pixel portion 302, whereby a light-emitting apparatus capable of displaying a full-color image can be obtained. In addition to the light-emitting devices that emit light of three kinds of colors (R, G, and B), for example, light-emitting devices that emit light of white (W), yellow (Y), magenta (M), cyan (C), and the like may be formed. For example, when the light-emitting devices that emit light of some of the above colors are used in combination with the light-emitting devices that emit light of three kinds of colors (R, G, and B), effects such as an improvement in color purity and a reduction in power consumption can be achieved. Alternatively, a light-emitting apparatus which is capable of displaying a full-color image may be fabricated by a combination with color filters. As color filters, red (R), green (G), blue (B), cyan (C), magenta (M), and yellow (Y) color filters and the like can be used.

When the second substrate 306 and the first substrate 301 are bonded to each other with the sealant 305, the FETs (309, 310, 311, and 312) and the light-emitting device 317 over the first substrate 301 are provided in a space 318 surrounded by the first substrate 301, the second substrate 306, and the sealant 305. Note that the space 318 may be filled with an inert gas (e.g., nitrogen or argon) or an organic substance (including the sealant 305).

An epoxy resin, glass frit, or the like can be used for the sealant 305. It is preferable to use a material that is permeable to as little moisture and oxygen as possible for the sealant 305. As the second substrate 306, a substrate that can be used as the first substrate 301 can be similarly used. Thus, any of the various substrates described in the other embodiments can be appropriately used. As the substrate, a glass substrate, a quartz substrate, or a plastic substrate made of fiber-reinforced plastic (FRP), polyvinyl fluoride (PVF), polyester, an acrylic resin, or the like can be used. In the case where glass frit is used for the sealant, the first substrate 301 and the second substrate 306 are preferably glass substrates in terms of adhesion.

Accordingly, the active-matrix light-emitting apparatus can be obtained.

In the case where the active-matrix light-emitting apparatus is provided over a flexible substrate, the FETs and the light-emitting device may be directly formed over the flexible substrate; alternatively, the FETs and the light-emitting device may be formed over a substrate provided with a separation layer and then separated at the separation layer by application of heat, force, laser, or the like to be transferred to a flexible substrate. For the separation layer, a stack including inorganic films such as a tungsten film and a silicon oxide film, or an organic resin film of polyimide or the like can be used, for example. Examples of the flexible substrate include, in addition to a substrate over which a transistor can be formed, a paper substrate, a cellophane substrate, an aramid film substrate, a polyimide film substrate, a cloth substrate (including a natural fiber (silk, cotton, or hemp), a synthetic fiber (nylon, polyurethane, or polyester), a regenerated fiber (acetate, cupro, rayon, or regenerated polyester), or the like), a leather substrate, and a rubber substrate. With the use of any of these substrates, an increase in durability, an increase in heat resistance, a reduction in weight, and a reduction in thickness can be achieved.

The structures described in this embodiment can be used in combination with any of the structures described in the other embodiments, as appropriate.

Embodiment 5

In this embodiment, examples of a variety of electronic devices and an automobile manufactured using the light-emitting device of one embodiment of the present invention or a light-emitting apparatus including the light-emitting device of one embodiment of the present invention will be described. Note that the light-emitting apparatus can be used mainly in a display portion of the electronic device described in this embodiment.

Electronic devices illustrated in FIGS. 4A to 4E can include a housing 7000, a display portion 7001, a speaker 7003, an LED lamp 7004, operation keys 7005 (including a power switch or an operation switch), a connection terminal 7006, a sensor 7007 (a sensor having a function of measuring force, displacement, position, speed, acceleration, angular velocity, rotational frequency, distance, light, liquid, magnetism, temperature, a chemical substance, sound, time, hardness, an electric field, current, voltage, electric power, radiation, flow rate, humidity, gradient, oscillation, odor, or infrared ray), a microphone 7008, and the like.

Figure 4A:
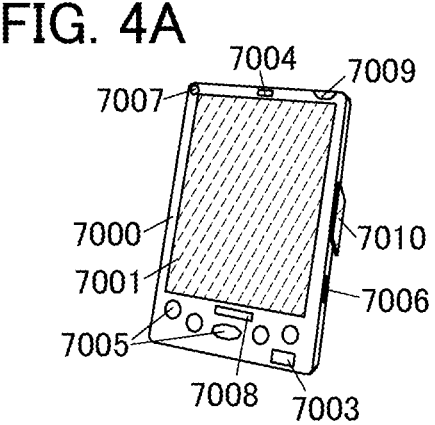
FIGS. 4A, 4B, 4C, 4D, 4E, 4F, and 4G are views illustrating a mobile computer, a portable image reproducing device, a digital camera, a portable information terminal, another portable information terminal, a television set, and another portable information terminal, respectively.

FIG. 4A illustrates a mobile computer that can include a switch 7009, an infrared port 7010, and the like in addition to the above components.

Figure 4B:
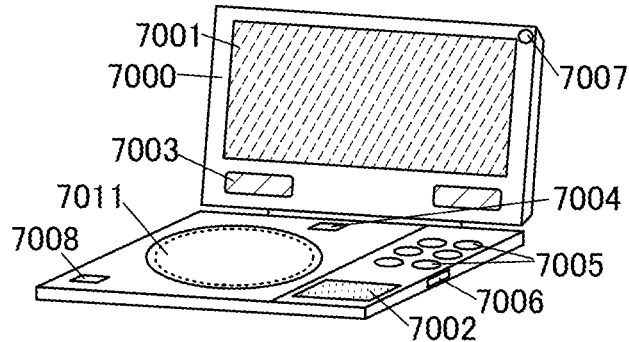

FIG. 4B illustrates a portable image reproducing device (e.g., a DVD player) that is provided with a recording medium and can include a second display portion 7002, a recording medium reading portion 7011, and the like in addition to the above components.

Figure 4C:
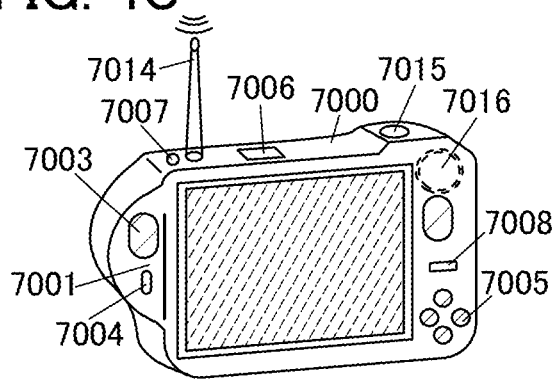

FIG. 4C illustrates a digital camera that has a television reception function and can include an antenna 7014, a shutter button 7015, an image receiving portion 7016, and the like in addition to the above components.

Figure 4D:
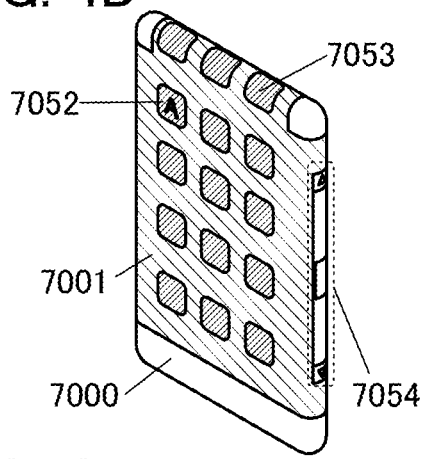

FIG. 4D illustrates a portable information terminal. The portable information terminal has a function of displaying information on three or more surfaces of the display portion 7001. Here, information 7052, information 7053, and information 7054 are displayed on different surfaces. For example, a user of the portable information terminal can check the information 7053 displayed such that it can be seen from above the portable information terminal, with the portable information terminal put in a breast pocket of his/her clothes. Thus, the user can see the display without taking out the portable information terminal from the pocket and decide whether to answer the call, for example.

Figure 4E:
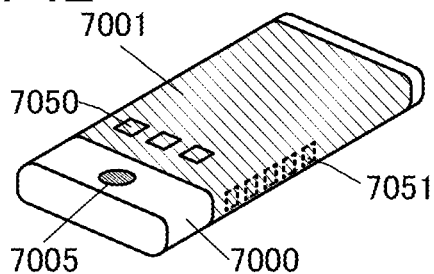

FIG. 4E illustrates a portable information terminal (e.g., a smartphone) and can include the display portion 7001, the operation key 7005, and the like in the housing 7000. Note that the portable information terminal may include a speaker 7003, a connection terminal 7006, a sensor 7007, or the like. The portable information terminal can display text and image data on its plurality of surfaces. Here, three icons 7050 are displayed. Furthermore, information 7051 indicated by dashed rectangles can be displayed on another surface of the display portion 7001. Examples of the information 7051 include notification of reception of an e-mail, an SNS message, an incoming call, or the like, the title and sender of an e-mail, an SNS message, or the like, the date, the time, remaining battery, and the reception strength of an antenna. The icon 7050 or the like may be displayed at the position where the information 7051 is displayed.

Figure 4F:
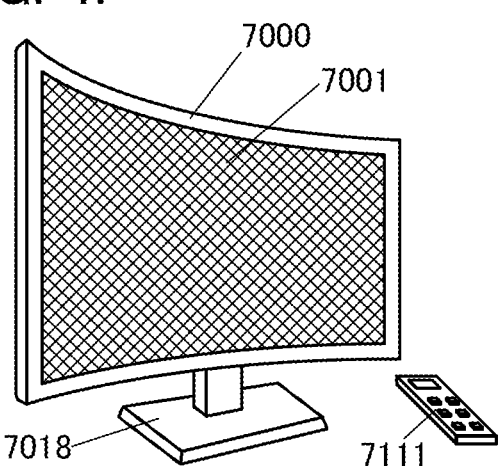

FIG. 4F illustrates a large-size television set (also referred to as TV or a television receiver) and can include the housing 7000, the display portion 7001, and the like. In addition, here, the housing 7000 is supported by a stand 7018. The television set can be operated with a separate remote controller 7111 or the like. The display portion 7001 may include a touch sensor. The television set can be operated by touching the display portion 7001 with a finger or the like. The remote controller 7111 may be provided with a display portion for displaying information output from the remote controller 7111. With operation keys or a touch panel of the remote controller 7111, channels and volume can be controlled and images displayed on the display portion 7001 can be controlled.

The electronic devices illustrated in FIGS. 4A to 4F can have a variety of functions, such as a function of displaying a variety of information (a still image, a moving image, a text image, and the like) on the display portion, a touch panel function, a function of displaying a calendar, date, time, and the like, a function of controlling processing with a variety of types of software (programs), a wireless communication function, a function of being connected to a variety of computer networks with a wireless communication function, a function of transmitting and receiving a variety of data with a wireless communication function, and a function of reading a program or data stored in a recording medium and displaying the program or data on the display portion. Furthermore, the electronic device including a plurality of display portions can have a function of displaying image data mainly on one display portion while displaying text data mainly on another display portion, a function of displaying a three-dimensional image by displaying images on a plurality of display portions with a parallax taken into account, or the like. Furthermore, the electronic device including an image receiving portion can have a function of shooting a still image, a function of shooting a moving image, a function of automatically or manually correcting a shot image, a function of storing a shot image in a recording medium (an external recording medium or a recording medium incorporated in the camera), a function of displaying a shot image on the display portion, or the like. Note that functions that can be provided for the electronic devices illustrated in FIGS. 4A to 4F are not limited to those described above, and the electronic devices can have a variety of functions.

Figure 4G:
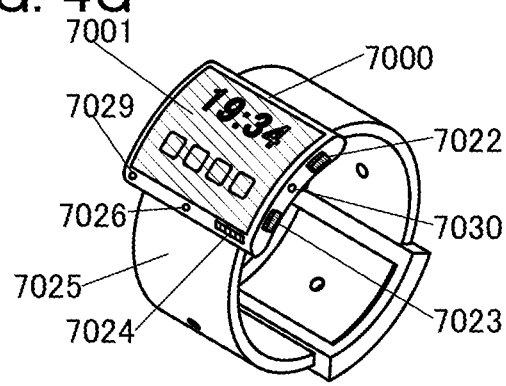

FIG. 4G illustrates a watch-type portable information terminal, which can be used as a smart watch, for example. The watch-type portable information terminal includes the housing 7000, the display portion 7001, operation buttons 7022 and 7023, a connection terminal 7024, a band 7025, a microphone 7026, a sensor 7029, a speaker 7030, and the like. The display surface of the display portion 7001 is curved, and images can be displayed on the curved display surface. Furthermore, mutual communication between the portable information terminal and, for example, a headset capable of wireless communication can be performed, and thus hands-free calling is possible with the portable information terminal. Note that the connection terminal 7024 allows mutual data transmission with another information terminal and charging. Wireless power feeding can also be employed for the charging operation.

The display portion 7001 mounted in the housing 7000 serving as a bezel includes a non-rectangular display region. The display portion 7001 can display an icon indicating time, another icon, and the like. The display portion 7001 may be a touch panel (input/output device) including a touch sensor (input device).

The smart watch illustrated in FIG. 4G can have a variety of functions, such as a function of displaying a variety of information (a still image, a moving image, a text image, and the like) on the display portion, a touch panel function, a function of displaying a calendar, date, time, and the like, a function of controlling processing with a variety of types of software (programs), a wireless communication function, a function of being connected to a variety of computer networks with a wireless communication function, a function of transmitting and receiving a variety of data with a wireless communication function, and a function of reading a program or data stored in a recording medium and displaying the program or data on the display portion.

The housing 7000 can include a speaker, a sensor (a sensor having a function of measuring force, displacement, position, speed, acceleration, angular velocity, rotational frequency, distance, light, liquid, magnetism, temperature, a chemical substance, sound, time, hardness, an electric field, current, voltage, electric power, radiation, flow rate, humidity, gradient, oscillation, odor, or infrared rays), a microphone, and the like.

Note that the light-emitting apparatus of one embodiment of the present invention and the display device including the light-emitting device of one embodiment of the present invention can be used in the display portion of each electronic device described in this embodiment, so that a long-lifetime electronic device can be obtained.

Figure 5A:
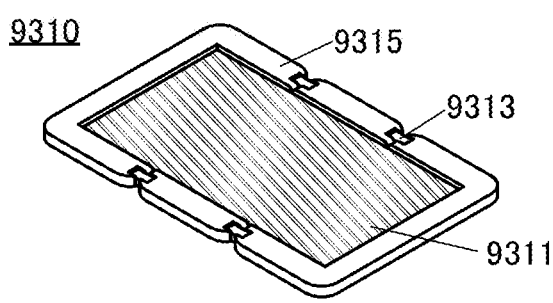
FIGS. 5A to 5C are each a view illustrating an electronic device.
Figure 5B:
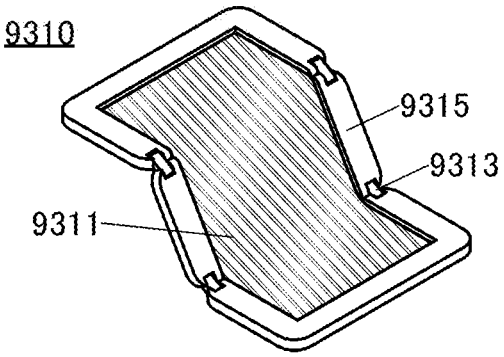
Figure 5C:
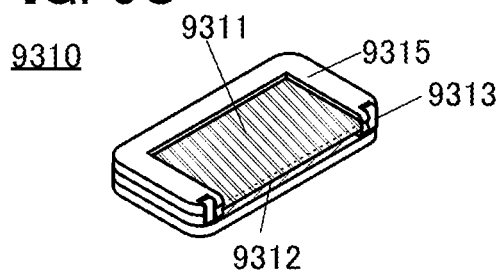

Another electronic device including the light-emitting apparatus is a foldable portable information terminal illustrated in FIGS. 5A to 5C. FIG. 5A illustrates a portable information terminal 9310 which is opened. FIG. 5B illustrates the portable information terminal 9310 which is being opened or being folded. FIG. 5C illustrates the portable information terminal 9310 which is folded. The portable information terminal 9310 is highly portable when folded. The portable information terminal 9310 is highly browsable when opened because of a seamless large display region.

A display portion 9311 is supported by three housings 9315 joined together by hinges 9313. Note that the display portion 9311 may be a touch panel (input/output device) including a touch sensor (input device). By bending the display portion 9311 at a connection portion between two housings 9315 with the use of the hinges 9313, the portable information terminal 9310 can be reversibly changed in shape from an opened state to a folded state. The light-emitting apparatus of one embodiment of the present invention can be used for the display portion 9311. In addition, a long-lifetime electronic device can be obtained. A display region 9312 in the display portion 9311 is a display region that is positioned at a side surface of the portable information terminal 9310 which is folded. On the display region 9312, information icons, file shortcuts of frequently used applications or programs, and the like can be displayed, and confirmation of information and start of application and the like can be smoothly performed.

Figure 6A:
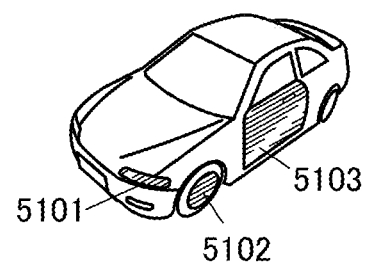
FIGS. 6A and 6B are each a view illustrating an automobile.
Figure 6B:
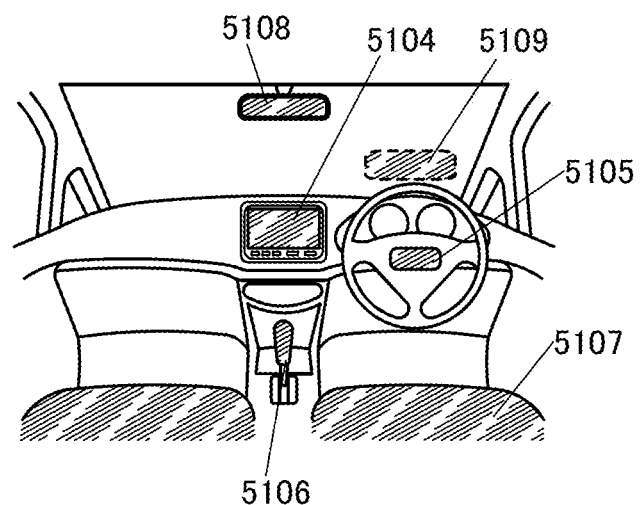

FIGS. 6A and 6B illustrate an automobile including the light-emitting apparatus. The light-emitting apparatus can be incorporated in the automobile, and specifically, can be included in lights 5101 (including lights of the rear part of the car), a wheel cover 5102, a part or whole of a door 5103, or the like on the outer side of the automobile which is illustrated in FIG. 6A. The light-emitting apparatus can also be included in a display portion 5104, a steering wheel 5105, a gear lever 5106, a seat 5107, an inner rearview mirror 5108, a windshield 5109, or the like on the inner side of the automobile which is illustrated in FIG. 6B, or in a part of a glass window.

In the above manner, the electronic devices and automobiles can be obtained using the light-emitting apparatus or the display device of one embodiment of the present invention. In that case, a long-lifetime electronic device can be obtained. Note that the light-emitting apparatus or the display device can be used for electronic devices and automobiles in a variety of fields without being limited to those described in this embodiment.

The structures described in this embodiment can be used in combination with any of the structures described in the other embodiments, as appropriate.

Embodiment 6

In this embodiment, the structure of a lighting device fabricated using the light-emitting apparatus of one embodiment of the present invention or the light-emitting device which is part of the light-emitting apparatus will be described with reference to FIGS. 7A and 7B.

Figure 7A:
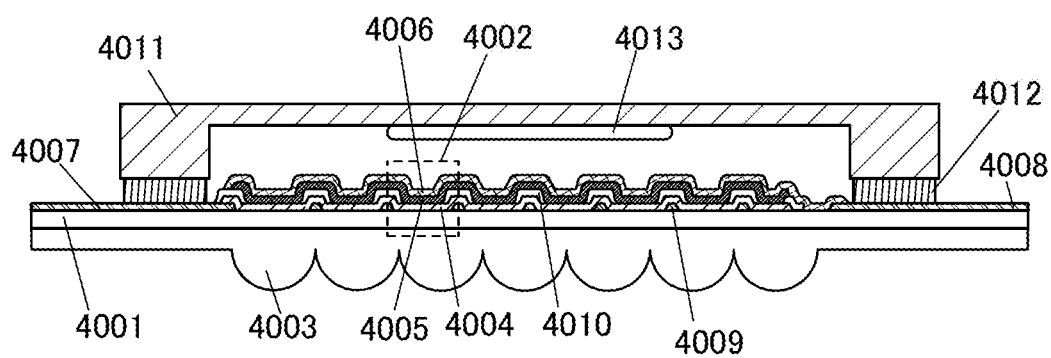
FIGS. 7A and 7B are each a view illustrating a lighting device.
Figure 7B:
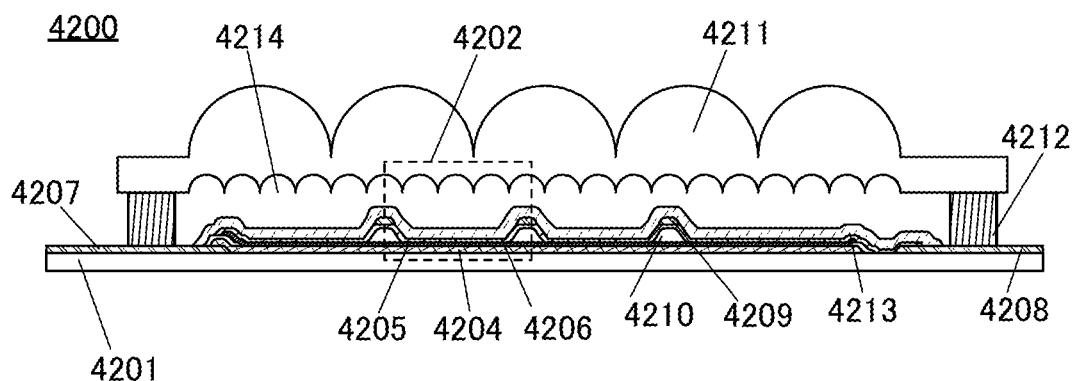

FIGS. 7A and 7B are examples of cross-sectional views of lighting devices. FIG. 7A illustrates a bottom-emission lighting device in which light is extracted from the substrate side, and FIG. 7B illustrates a top-emission lighting device in which light is extracted from the sealing substrate side.

A lighting device 4000 illustrated in FIG. 7A includes a light-emitting device 4002 over a substrate 4001. In addition, the lighting device 4000 includes a substrate 4003 with unevenness on the outside of the substrate 4001. The light-emitting device 4002 includes a first electrode 4004, an EL layer 4005, and a second electrode 4006.

The first electrode 4004 is electrically connected to an electrode 4007, and the second electrode 4006 is electrically connected to an electrode 4008. In addition, an auxiliary wiring 4009 electrically connected to the first electrode 4004 may be provided. Note that an insulating layer 4010 is formed over the auxiliary wiring 4009.

The substrate 4001 and a sealing substrate 4011 are bonded to each other with a sealant 4012. A desiccant 4013 is preferably provided between the sealing substrate 4011 and the light-emitting device 4002. The substrate 4003 has the unevenness illustrated in FIG. 7A, whereby the extraction efficiency of light emitted from the light-emitting device 4002 can be increased.

A lighting device 4200 illustrated in FIG. 7B includes a light-emitting device 4202 over a substrate 4201. The light-emitting device 4202 includes a first electrode 4204, an EL layer 4205, and a second electrode 4206.

The first electrode 4204 is electrically connected to an electrode 4207, and the second electrode 4206 is electrically connected to an electrode 4208. An auxiliary wiring 4209 electrically connected to the second electrode 4206 may be provided. An insulating layer 4210 may be provided under the auxiliary wiring 4209.

The substrate 4201 and a sealing substrate 4211 with unevenness are bonded to each other with a sealant 4212. A barrier film 4213 and a planarization film 4214 may be provided between the sealing substrate 4211 and the light-emitting device 4202. The sealing substrate 4211 has the unevenness illustrated in FIG. 7B, whereby the extraction efficiency of light emitted from the light-emitting device 4202 can be increased.

Examples of such lighting devices include a ceiling light as an indoor lighting. Examples of the ceiling light include a direct-mount light and an embedded light. Such lighting devices are fabricated using the light-emitting apparatus and a housing or a cover in combination.

For another example, such lighting devices can be used for a foot light that lights a floor so that safety on the floor can be improved. A foot light can be effectively used in a bedroom, on a staircase, or on a passage, for example. In that case, the size or shape of the foot light can be changed in accordance with the area or structure of a room. The foot light can be a stationary lighting device fabricated using the light-emitting apparatus and a support in combination.

Such lighting devices can also be used for a sheet-like lighting device (sheet-like lighting). The sheet-like lighting, which is attached to a wall when used, is space-saving and thus can be used for a wide variety of uses. Furthermore, the area of the sheet-like lighting can be easily increased. The sheet-like lighting can also be used on a wall or housing having a curved surface.

Besides the above examples, when the light-emitting apparatus of one embodiment of the present invention or the light-emitting device which is part of the light-emitting apparatus is used as part of furniture in a room, a lighting device that functions as the furniture can be obtained.

As described above, a variety of lighting devices that include the light-emitting apparatus can be obtained. Note that these lighting devices are also embodiments of the present invention.

The structures described in this embodiment can be used in combination with any of the structures described in the other embodiments, as appropriate.

Example 1

Synthesis Example 1

In this example, a synthesis method of N,N'-bis[4-(9H-carbazol-9-yl)phenyl]-N,N',6,7-tetraphenyl-[1,2,5]thiadiazolo[3,4-g]quinoxaline-4,9-diamine (abbreviation: YGA2TDQn), which is an organic compound of one embodiment of the present invention represented by Structural Formula (100) in Embodiment 1, will be described. A structure of YGA2TDQn is shown below.

[Chemical Formula 42]

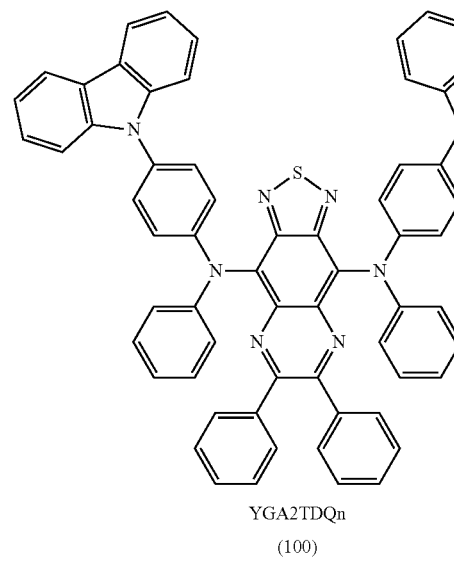

YGA2TDQn
(100)

<Synthesis of YGA2TDQn>

First, 1.0 g (2.0 mmol) of 4,9-dibromo-6,7-diphenyl-[1,2,5]thiadiazolo[3,4-g]quinoxaline, 1.4 g (4.1 mmol) of 4-(9H-carbazol-9-yl)diphenylamine, 0.4 g (0.9 mmol) of 2-dicyclohexylphosphino-2',6'-dimethoxybiphenyl (SPhos), and 0.5 g (5.5 mmol) of sodium tert-butoxide were put in a 100 mL three-neck flask, and the air in the flask was replaced with nitrogen. To this mixture, 20.0 mL of xylene and 0.1 mg (0.2 mmol) of bis(dibenzylideneacetone)palladium(0) were added, and stirring was performed at 100° C. for 1.5 hours, at 120° C. for 2.8 hours, and at 150° C. for 3.0 hours.

The stirred mixture was suction-filtered through a filter in which Florisil (produced by Wako Pure Chemical Industries, Ltd., Catalog No. 540-00135), Celite (produced by Wako Pure Chemical Industries, Ltd., Catalog No. 531-16855), and alumina were stacked in this order. The obtained filtrate was concentrated to give a solid. The obtained solid was purified by silica gel column chromatography (developing solvent, hexane:toluene=3:7) to give 0.3 g of the target black solid in a yield of 13%.

By a train sublimation method, 0.16 g of the obtained black solid was purified. The solid was heated under the sublimation purification conditions where the pressure was $1.2 \times 10^{-2}$ Pa and the heating temperature was 350° C. After the purification by sublimation, 0.11 g of the target black solid was obtained at a collection rate of 67%. The synthesis scheme is shown in (a-1) below.

[Chemical Formula 43]

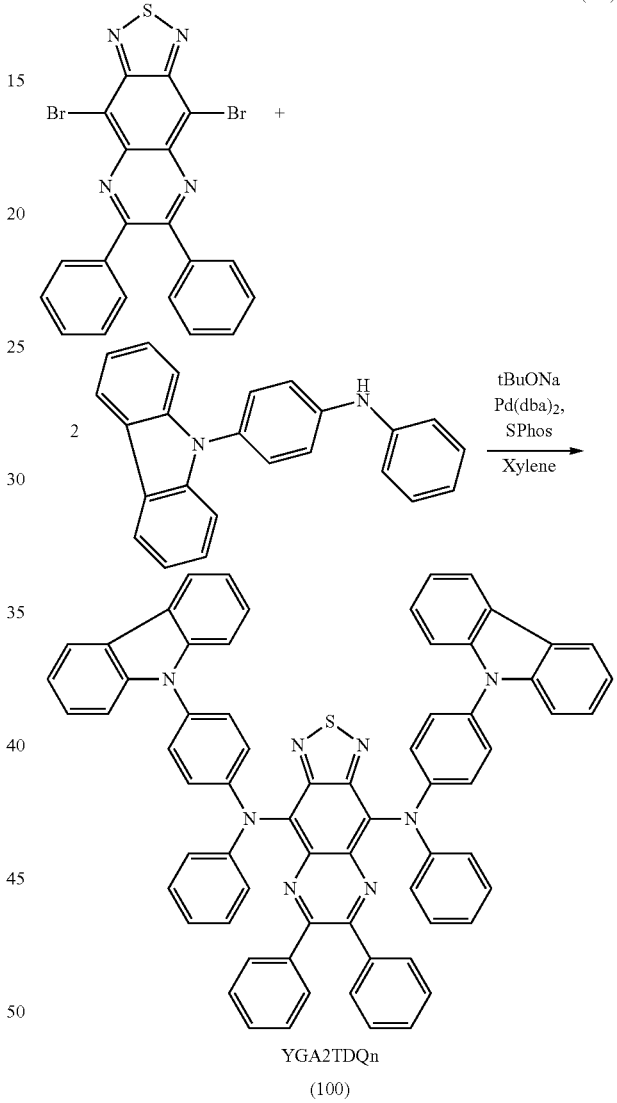

YGA2TDQn
(100)

Figure 8:
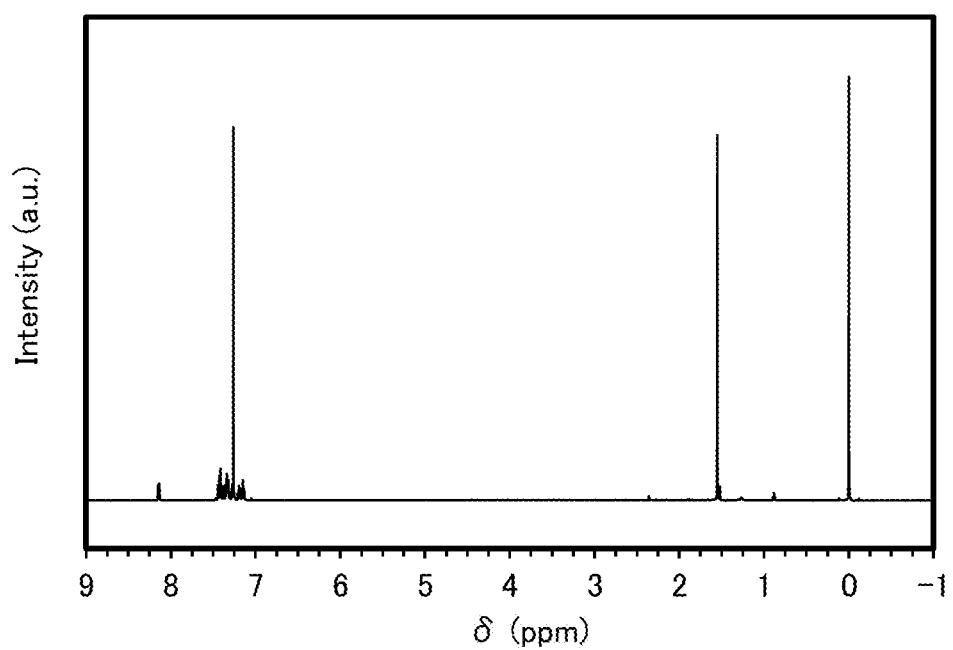
FIG. 8 is a $^1$H-NMR chart of an organic compound represented by Structural Formula (100)

Analysis results by nuclear magnetic resonance ($^1$H-NMR) spectroscopy of the black solid obtained by the above synthesis method are shown below. A $^1$H-NMR chart is shown in FIG. 8. These results reveal that YGA2TDQn, the organic compound of one embodiment of the present invention represented by Structural Formula (100), was obtained in this example.

$^1$H NMR (CDCl$_3$, 500 MHz): δ=7.14-7.43 (m, 40H), 8.14 (d, J=8.0 Hz, 4H).

<<Properties of YGA2TDQn>>

Next, an ultraviolet-visible absorption spectrum (hereinafter, simply referred to as an absorption spectrum) of a toluene solution of YGA2TDQn and an emission spectrum thereof were measured.

Figure 9:
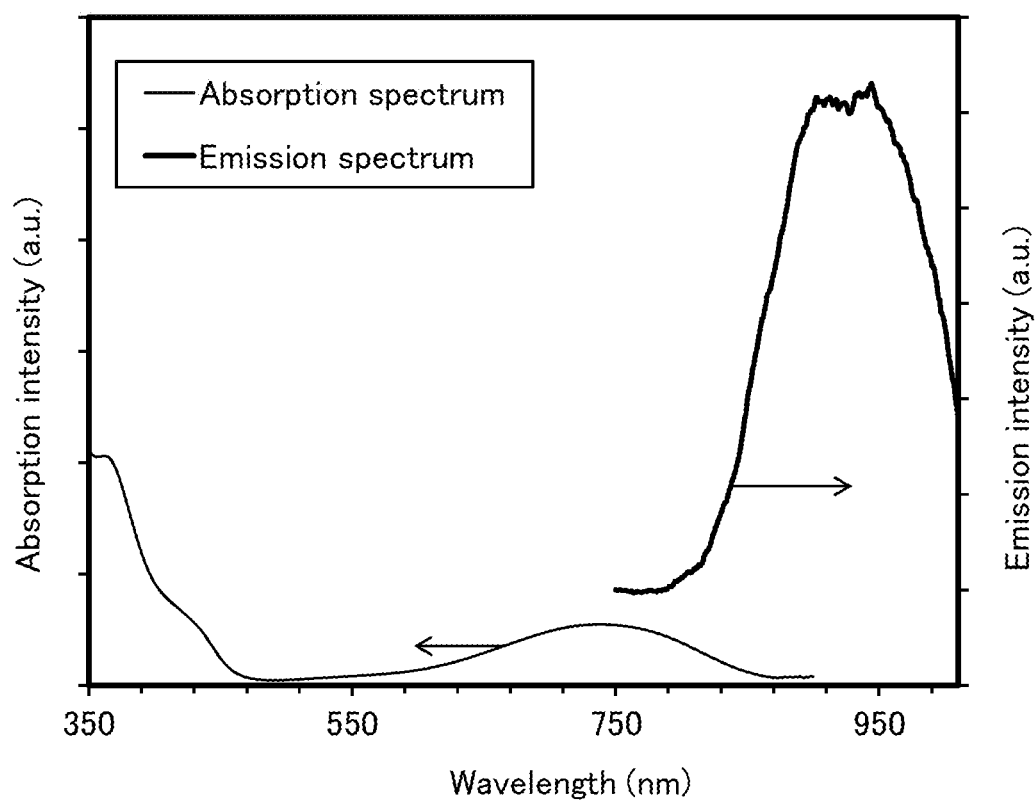
FIG. 9 shows an ultraviolet-visible absorption spectrum and an emission spectrum of the organic compound represented by Structural Formula (100)

The absorption spectrum was measured with an ultraviolet-visible spectrophotometer (V-550, produced by JASCO Corporation). The emission spectrum was measured with a fluorescence spectrophotometer (FP-8600, produced by JASCO Corporation). FIG. 9 shows the obtained absorption and emission spectra of the toluene solution. The horizontal axis represents wavelength, and the vertical axis represents intensity.

The results in FIG. 9 show that YGA2TDQn in the toluene solution has an absorption peak at around 737 nm and an emission peak at around 925 nm (excitation wavelength: 739 nm).

Next, the HOMO level and the LUMO level of YGA2TDQn were obtained through a cyclic voltammetry (CV) measurement. The calculation method is shown below.

An electrochemical analyzer (ALS model 600A or 600C, produced by BAS Inc.) was used as the measurement apparatus. A solution for the CV measurement was prepared in the following manner: tetra-n-butylammonium perchlorate (n-Bu$_4$NClO$_4$, produced by Tokyo Chemical Industry Co., Ltd., catalog No. T0836) as a supporting electrolyte was dissolved in dehydrated dimethylformamide (DMF, produced by Sigma-Aldrich Co. LLC., 99.8%, catalog No. 22705-6) as a solvent at a concentration of 100 mmol/L, and the object to be measured was dissolved therein at a concentration of 2 mmol/L.

A platinum electrode (PTE platinum electrode, manufactured by BAS Inc.) was used as a working electrode, another platinum electrode (Pt counter electrode for VC-3 (5 cm), manufactured by BAS Inc.) was used as an auxiliary electrode, and an Ag/Ag$^+$ electrode (RE7 reference electrode for nonaqueous solvent, manufactured by BAS Inc.) was used as a reference electrode. Note that the measurement was performed at a room temperature (20° C. to 25° C.).

In addition, the scan speed in the CV measurement was fixed to 0.1 V/sec, and an oxidation potential Ea [V] and a reduction potential Ec [V] with respect to the reference electrode were measured. The potential Ea is an intermediate potential of an oxidation-reduction wave, and the potential Ec is an intermediate potential of a reduction-oxidation wave. Here, since the potential energy of the reference electrode used in this example with respect to the vacuum level is known to be −4.94 [eV], the HOMO level and the LUMO level can be calculated by the following formulae: HOMO level [eV]−4.94−Ea and LUMO level [eV]=−4.94−Ec.

Furthermore, CV measurement was repeated 100 times, and the oxidation-reduction wave in the hundredth cycle was compared with the oxidation-reduction wave in the first cycle to examine the electrical stability of the compound.

As a result, in the measurement of the oxidation potential Ea [V] of YGA2TDQn, the HOMO level was found to be −5.48 eV. In contrast, the LUMO level was found to be −3.93 eV in the measurement of the reduction potential Ec [V]. When the oxidation-reduction wave was repeatedly measured, in the Ea measurement, the peak intensity of the oxidation-reduction wave in the hundredth cycle was maintained to be 87% of that of the oxidation-reduction wave in the first cycle, and in the Ec measurement, the peak intensity of the oxidation-reduction wave in the hundredth cycle was maintained to be 97% of that of the oxidation-reduction wave in the first cycle; thus, resistance to oxidation and reduction of YGA2TDQn was found to be extremely high.

Example 2

Synthesis Example 2

In this example, a synthesis method of N,N'-bis(9-phenyl-9H-carbazol-4-yl)-N,N',6,7-tetraphenyl-[1,2,5]thiadiazolo[3,4-g]quinoxaline-4,9-diamine (abbreviation: PCA2TDQn), which is an organic compound of one embodiment of the present invention represented by Structural Formula (200) in Embodiment 1, will be described. A structure of PCA2TDQn is shown below.

[Chemical Formula 44]

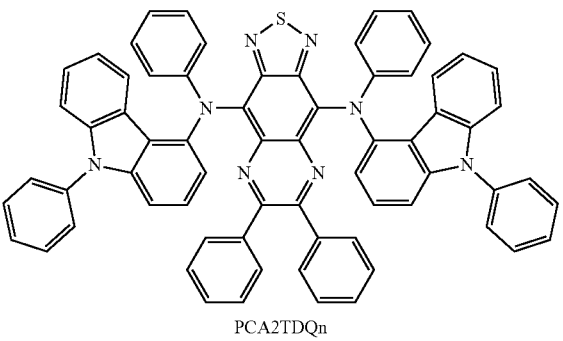

PCA2TDQn

Step 1: Synthesis of
N,9-diphenyl-9H-carbazol-4-amine

First, 3.0 g (9.3 mmol) of 4-bromo-9-diphenyl-9H-carbazole and 2.7 g (27.9 mmol) of sodium tert-butoxide were put in a 200 mL three-neck flask, and the air in the flask was replaced with nitrogen. To this mixture, 33.0 mL of toluene, 0.90 ml (20.0 mmol) of aniline, 0.5 mL of a 10% hexane solution of tri(tert-butyl)phosphine, and 48 mg (0.1 mmol) of bis(dibenzylideneacetone)palladium(0) were added, and stirring was performed at 80° C. for 4.0 hours.

The stirred mixture was suction-filtered through a filter in which Florisil (produced by Wako Pure Chemical Industries, Ltd., Catalog No. 540-00135), Celite (produced by Wako Pure Chemical Industries, Ltd., Catalog No. 531-16855), and alumina were stacked in this order. The obtained filtrate was concentrated to give an oily substance. The obtained oily substance was purified by silica gel column chromatography (developing solvent, hexane:toluene=3:2) to give 3.0 g of the target compound in a yield of 97%. The synthesis scheme of Step 1 is shown in (b-1) below.

[Chemical Formula 45]

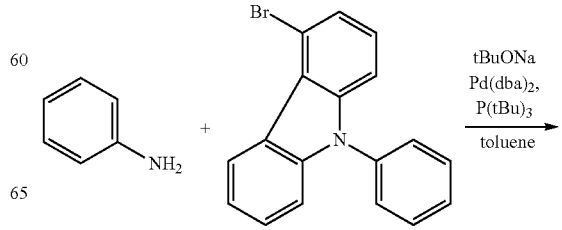

-continued

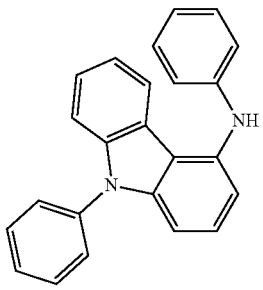

Step 2: Synthesis of 4,9-bis(N,9-diphenyl-9H-carbazol-4-amine)-6,7-diphenyl-[1,2,5]thiadiazole[3,4-g]quinoxaline First, 1.0 g (2.0 mmol) of 4,9-dibromo-6,7-diphenyl-[1,2,5]thiadiazole[3,4-g]quinoxaline, 1.5 g (4.4 mmol) of N,9-diphenyl-9H-carbazol-4-amine, and 0.6 g (6.0 mmol) of sodium tert-butoxide were put in a 100 mL three-neck flask, and the air in the flask was replaced with nitrogen. To this mixture, 20.0 mL of xylene and 0.1 mg (0.2 mmol) of bis(dibenzylideneacetone)palladium(0) were added, and stirring was performed at 100° C. for 2.5 hours and at 120° C. for 6.8 hours.

The stirred mixture was suction-filtered through a filter in which Florisil (produced by Wako Pure Chemical Industries, Ltd., Catalog No. 540-00135), Celite (produced by Wako Pure Chemical Industries, Ltd., Catalog No. 531-16855), and alumina were stacked in this order. The obtained filtrate was concentrated to give a solid. The obtained solid was purified by silica gel column chromatography (developing solvent, hexane:toluene=2:7) to give a black solid. The obtained solid was recrystallized from toluene and hexane to give 0.9 g of the target black solid in a yield of 46%.

By a train sublimation method, 0.9 g of the obtained black solid was purified. The sublimation purification conditions were as follows: the pressure was 2.3×10⁻² Pa and heating was performed at 305° C. for 1 day, at 315° C. overnight, at 320° C. for 2 hours, and at 330° C. for 2 hours. After the purification by sublimation, 0.1 g of the target black solid was obtained at a collection rate of 9%. The synthesis scheme of Step 2 is shown in (b-2) below.

[Chemical Formula 46]

(b-2)

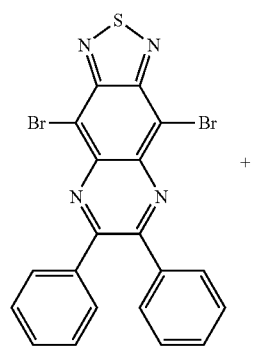

+

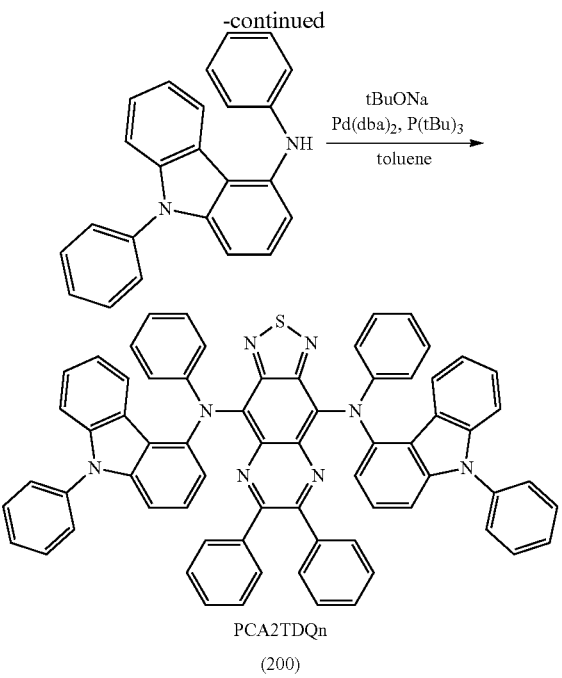

PCA2TDQn
(200)

Figure 10:
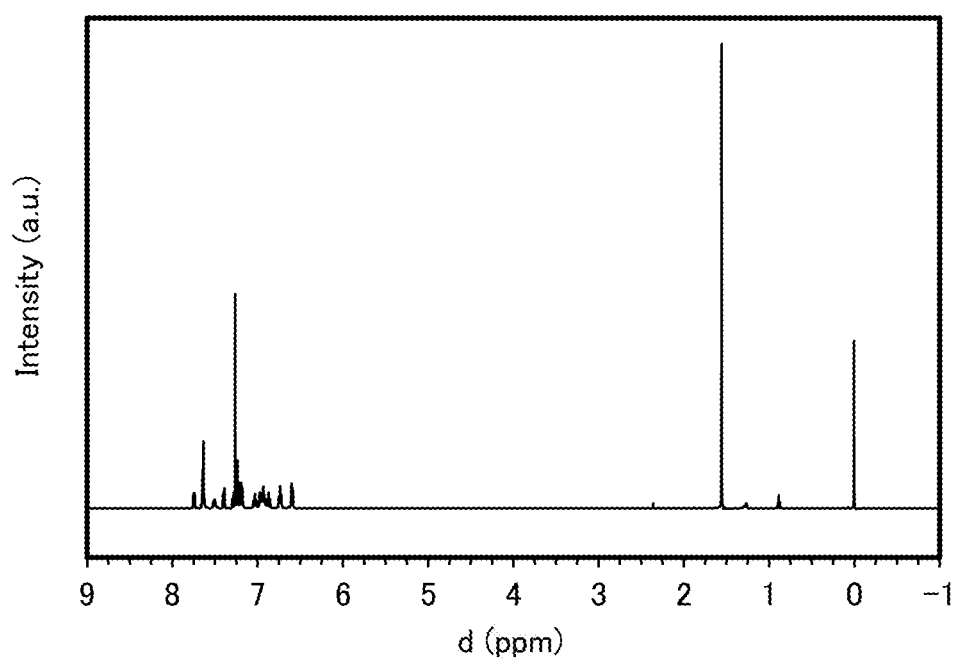
FIG. 10 is a $^1$H-NMR chart of an organic compound represented by Structural Formula (200)

Analysis results by nuclear magnetic resonance (¹H-NMR) spectroscopy of the black solid obtained by the above Step 2 are shown below. A ¹H-NMR chart is shown in FIG. 10. These results reveal that PCA2TDQn, the organic compound of one embodiment of the present invention represented by Structural Formula (200), was obtained in this example.

¹H NMR (CDCl$_3$, 500 MHz): δ=6.59 (d, J=8.0 Hz, 4H), 6.73 (t, J=8.0 Hz, 4H), 6.87 (t, J=7.5 Hz, 2H), 6.92-6.98 (m, 8H), 7.03 (t, J=7.5 Hz, 2H), 7.18-7.29 (m, 10H), 7.39 (d, J=8.0 Hz, 2H), 7.45-7.52 (m, 2H), 7.64 (d, J=5.0 Hz, 8H), 7.74 (d, J=8.0 Hz, 2H).

<<Properties of PCA2TDQn>>

Next, an ultraviolet-visible absorption spectrum (hereinafter, simply referred to as an absorption spectrum) of a toluene solution of PCA2TDQn and an emission spectrum thereof were measured.

Figure 11:
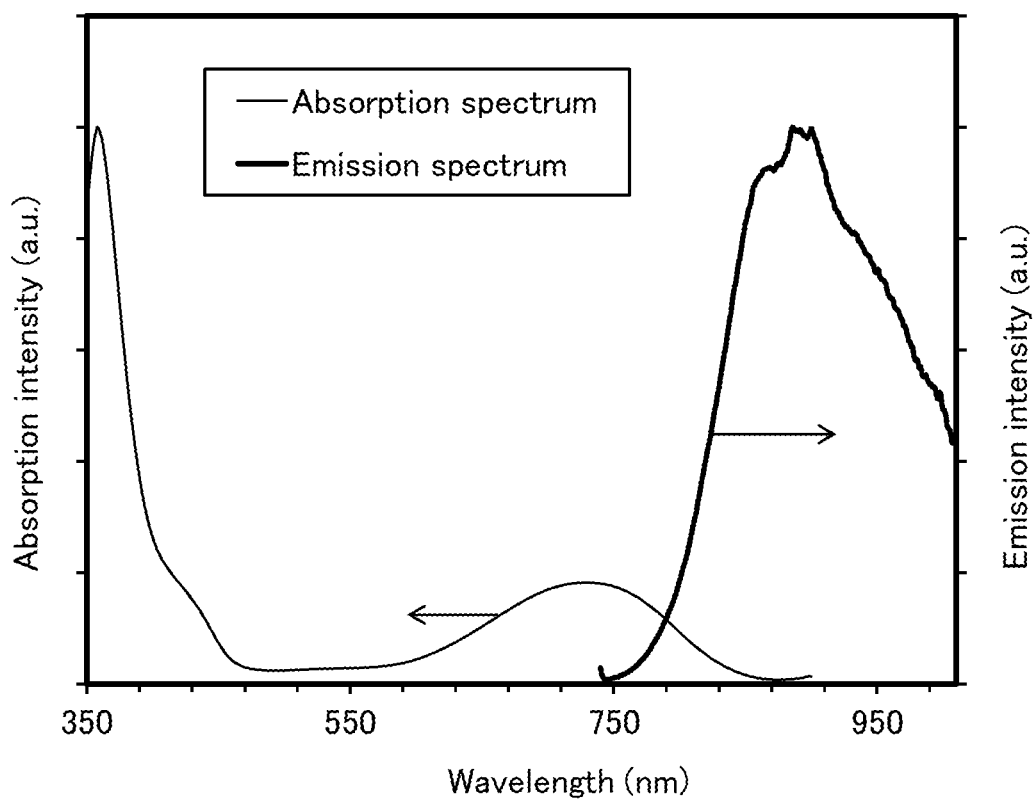
FIG. 11 shows an ultraviolet-visible absorption spectrum and an emission spectrum of the organic compound represented by Structural Formula (200)

The absorption spectrum was measured with an ultraviolet-visible spectrophotometer (V-550, produced by JASCO Corporation). The emission spectrum was measured with a fluorescence spectrophotometer (FP-8600, produced by JASCO Corporation). FIG. 11 shows the obtained absorption and emission spectra of the toluene solution. The horizontal axis represents wavelength, and the vertical axis represents intensity.

The results in FIG. 11 show that PCA2TDQn in the toluene solution has an absorption peak at around 732 nm and an emission peak at around 882 nm (excitation wavelength: 730 nm).

Next, the HOMO level and the LUMO level of PCA2TDQn were obtained through a cyclic voltammetry (CV) measurement. The same measurement method and calculation method as those used in Example 1 were used here.

As a result, in the measurement of the oxidation potential Ea [V] of PCA2TDQn, the HOMO level was found to be −5.28 eV In contrast, the LUMO level was found to be −3.86 eV in the measurement of the reduction potential Ec [V]. When the oxidation-reduction wave was repeatedly measured, in the Ea measurement, the peak intensity of the oxidation-reduction wave in the hundredth cycle was maintained to be 80% of that of the oxidation-reduction wave in the first cycle, and in the Ec measurement, the peak intensity of the oxidation-reduction wave in the hundredth cycle was maintained to be 94% of that of the oxidation-reduction wave in the first cycle; thus, resistance to oxidation and reduction of PCA2TDQn was found to be extremely high.

Example 3

Synthesis Example 3

In this example, a synthesis method of N,N-[(6,7-diphenyl[1,2,5]thiadiazolo[3,4-g]quinoxaline-4,9-diyl)di-4,1-phenylene]bis(N,9-diphenyl-9H-carbazol-3-amine) (abbreviation: PCAP2TDQn), which is an organic compound of one embodiment of the present invention represented by Structural Formula (300) in Embodiment 1, will be described. A structure of PCAP2TDQn is shown below.

[Chemical Formula 47]

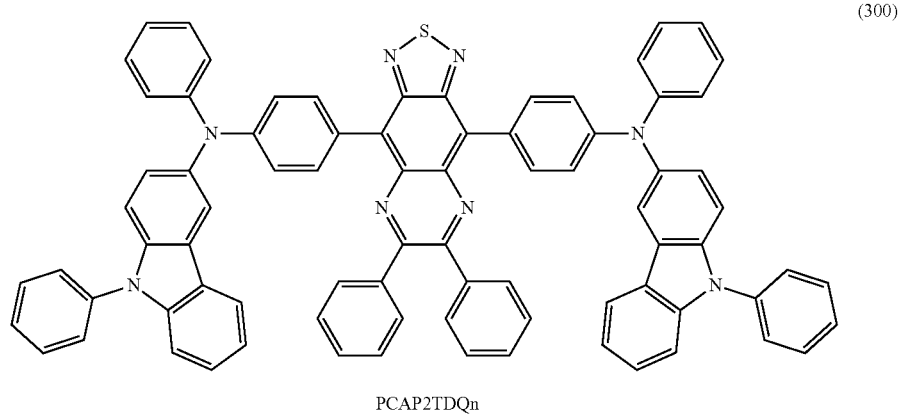

PCAP2TDQn (300)

[Chemical Formula 48]

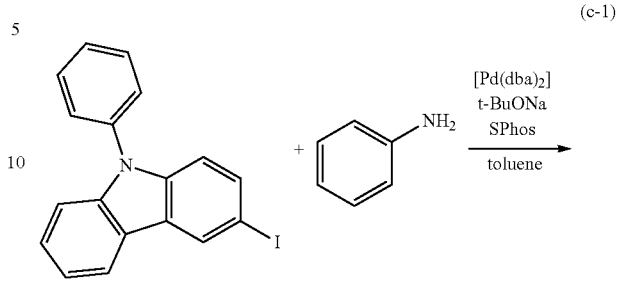

(c-1)

Step 1: Synthesis of N,9-diphenyl-9H-carbazol-3-amine

First, 16 g (45 mmol) of 3-iodo-9-phenylcarbazole, 4.1 mL (45 mmol) of aniline, 0.37 g (0.90 mmol) of 2-dicyclohexylphosphino-2',6'-dimethoxybiphenyl (SPhos), 8.6 g (90 mmol) of sodium tert-butoxide, and 225 mL of toluene were put in a 500 mL three-neck flask equipped with a reflux pipe. Degassing was performed, and the air in the flask was replaced with nitrogen. To this mixture, 0.26 mg (0.45 mmol) of bis(dibenzylideneacetone)palladium(0) was added, and the mixture was refluxed for 1.5 hours.

Then, water was added to this mixture to obtain an aqueous layer and an organic layer; the aqueous layer was subjected to extraction with toluene. Next, the extracted solution was combined with the organic layer, and the resulting mixture was washed with water and saturated saline and dried with magnesium sulfate. The obtained mixture was suction-filtered through a filter in which Florisil (produced by Wako Pure Chemical Industries, Ltd., Catalog No. 540-00135), Celite (produced by Wako Pure Chemical Industries, Ltd., Catalog No. 531-16855), and alumina were stacked in this order. The obtained filtrate was concentrated to give a solid. The obtained solid was purified by silica gel column chromatography (developing solvent, hexane:toluene=1:1) to give 14 g of the target white solid in a yield of 94%. The synthesis scheme of Step 1 is shown in (c-1) below.

-continued

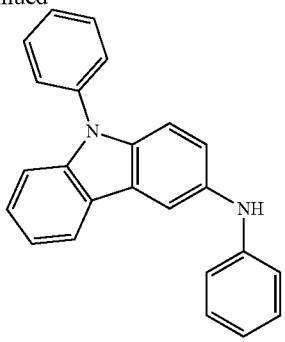

Step 2: Synthesis of N-(4-chlorophenyl)-N,9-diphenyl-9H-carbazol-3-amine

Next, 5.0 g (15 mmol) of N,9-diphenyl-9H-carbazol-3-amine obtained in Step 1, 3.6 g (15 mmol) of 1-chloro-4-iodobenzene, 0.12 g (0.30 mmol) of 2-dicyclohexylphosphino-2',6'-dimethoxybiphenyl (SPhos), 2.9 g (30 mmol) of sodium tert-butoxide, and 75 mL of toluene were put in a 200 mL three-neck flask equipped with a reflux pipe. Degassing was performed, and the air in the flask was replaced with nitrogen. To this mixture, 86 mg (0.15 mmol) of bis(dibenzylideneacetone)palladium(0) was added, and stirring was performed at 80° C. for 4 hours.

Then, water was added to this mixture to obtain an aqueous layer and an organic layer; the aqueous layer was subjected to extraction with toluene. Furthermore, the extracted solution was combined with the organic layer, and the resulting mixture was washed with water and saturated saline and dried with magnesium sulfate. The obtained mixture was suction-filtered through a filter in which Florisil (produced by Wako Pure Chemical Industries, Ltd., Catalog No. 540-00135), Celite (produced by Wako Pure Chemical Industries, Ltd., Catalog No. 531-16855), and alumina are stacked in this order. The obtained filtrate was concentrated to give a solid. The obtained solid was recrystallized from ethanol and acetone to give 4.0 g of the target white solid in a yield of 60%. The synthesis scheme of Step 2 is shown in (c-2) below.

[Chemical Formula 49]

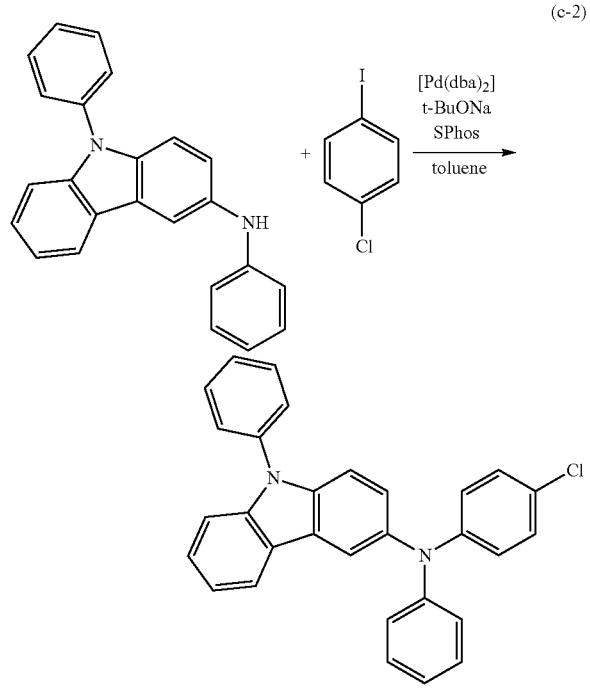

(c-2)

Step 3: Synthesis of N,9-diphenyl-N-[4-(4,4,5,5-tetramethyl-1,3,2-dioxaboran-2-yl)phenyl]-9H-carbazol-3-amine Next, 3.0 g (6.7 mmol) of N-(4-chlorophenyl)-N,9-diphenyl-9H-carbazol-3-amine obtained in Step 2, 1.7 g (6.7 mmol) of bis(pinacolato)diboron, 1.3 g (13 mmol) of potassium acetate, and 30 mL of xylene were put in a 200 mL three-neck flask equipped with a reflux pipe. Degassing was performed, and the air in the flask was replaced with nitrogen. To this mixture, 55 mg (67 μmol) of [1,1'-bis(diphenylphosphino)ferrocene]palladium(II)dichloridedichloromethane adduct was added, and the mixture was refluxed for 5 hours. Then, 60 mg (0.15 mmol) of 2-dicyclohexylphosphino-2',6'-dimethoxybiphenyl (SPhos) was added, and the mixture was further refluxed for 19 hours.

Then, water was added to this mixture to obtain an aqueous layer and an organic layer; the aqueous layer was subjected to extraction with toluene. Next, the extracted solution was combined with the organic layer, and the resulting mixture was washed with water and saturated saline and dried with magnesium sulfate. The obtained mixture was suction-filtered through a filter in which Florisil (produced by Wako Pure Chemical Industries, Ltd., Catalog No. 540-00135), Celite (produced by Wako Pure Chemical Industries, Ltd., Catalog No. 531-16855), and alumina were stacked in this order. The obtained filtrate was concentrated to give a solid. The obtained solid was purified by high performance liquid chromatography (HPLC; mobile phase: chloroform) to give 2.8 g of the target white solid in a yield of 78%. The synthesis scheme of Step 3 is shown in (c-3) below.

[Chemical Formula 50]

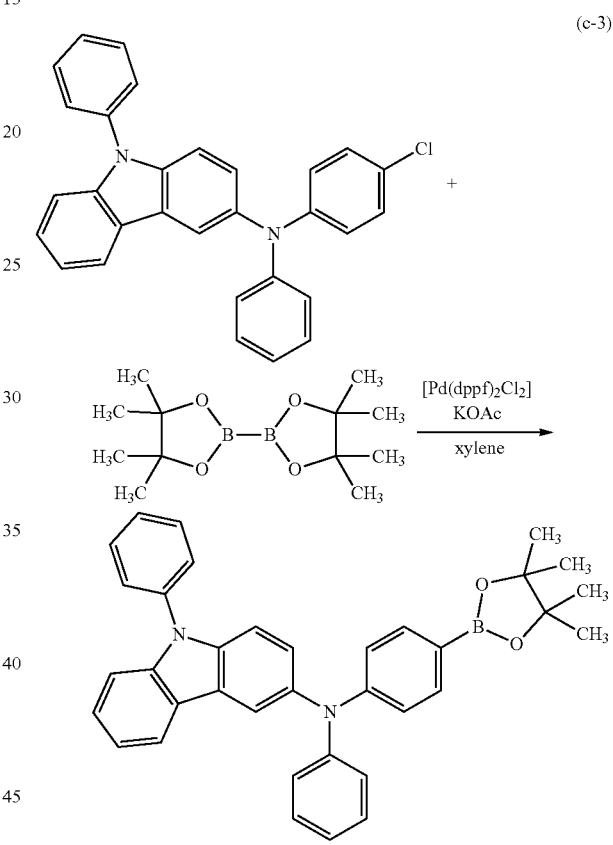

(c-3)

Analysis results by nuclear magnetic resonance ($^1$H-NMR) spectroscopy of the white solid obtained in Step 3 are shown below. These results reveal that N,9-diphenyl-N-[4-(4,4,5,5-tetramethyl-1,3,2-dioxaboran-2-yl)phenyl]-9H-carbazol-3-amine, which is the target object in Step 3, was obtained.

$^1$H NMR (dichloromethane-$d_2$, 500 MHz): δ=7.99 (d, J=7.5 Hz, 1H), 7.93 (d, J=1.5 Hz, 1H), 7.65-7.56 (m, 6H), 7.49 (t, J=7.5 Hz, 1H), 7.40-7.37 (m, 3H), 7.28-7.20 (m, 4H), 7.15 (dd, J=8.5, 1.0 Hz, 2H), 7.04-6.99 (m, 3H), 1.30 (s, 12H).

Step 4: Synthesis of PCAP2TDQn

Next, 2.2 g (4.0 mmol) of N,9-diphenyl-N-[4-(4,4,5,5-tetramethyl-1,3,2-dioxaboran-2-yl)phenyl]-9H-carbazol-3-amine obtained in Step 3, 1.0 g (2.0 mmol) of 4,9-dibromo-6,7-diphenyl-[1,2,5]thiadiazole[3,4-g]quinoxaline, 24 mg (80 μmol) of tri(ortho-tolyl)phosphine, 4 mL of a 2M aqueous solution of potassium carbonate, 15 mL of toluene, and 5 mL of ethanol were put in a 200 mL three-neck flask equipped with a reflux pipe. Degassing was performed, and the air in the flask was replaced with nitrogen. To this mixture, 9.0 mg (40 μmol) of palladium(II) acetate was added, and the mixture was refluxed for 8 hours.

Then, water was added to this mixture to obtain an aqueous layer and an organic layer; the aqueous layer was subjected to extraction with toluene. Next, the extracted solution was combined with the organic layer, and the resulting mixture was washed with water and saturated saline and dried with magnesium sulfate. The obtained mixture was suction-filtered through a filter in which Florisil (produced by Wako Pure Chemical Industries, Ltd., Catalog No. 540-00135), Celite (produced by Wako Pure Chemical Industries, Ltd., Catalog No. 531-16855), and alumina were stacked in this order. The obtained filtrate was concentrated to give a solid. The obtained solid was purified by silica gel column chromatography (developing solvent, hexane:toluene=1:4) and high performance liquid chromatography (HPLC; mobile phase: chloroform) to give 0.63 g of the target blue-green solid in a yield of 27%. The synthesis scheme is shown in (c-4) below.

<<Properties of PCAP2TDQn>>

Next, an ultraviolet-visible absorption spectrum (hereinafter, simply referred to as an absorption spectrum) of a toluene solution of PCAP2TDQn and an emission spectrum thereof were measured.

Figure 13:
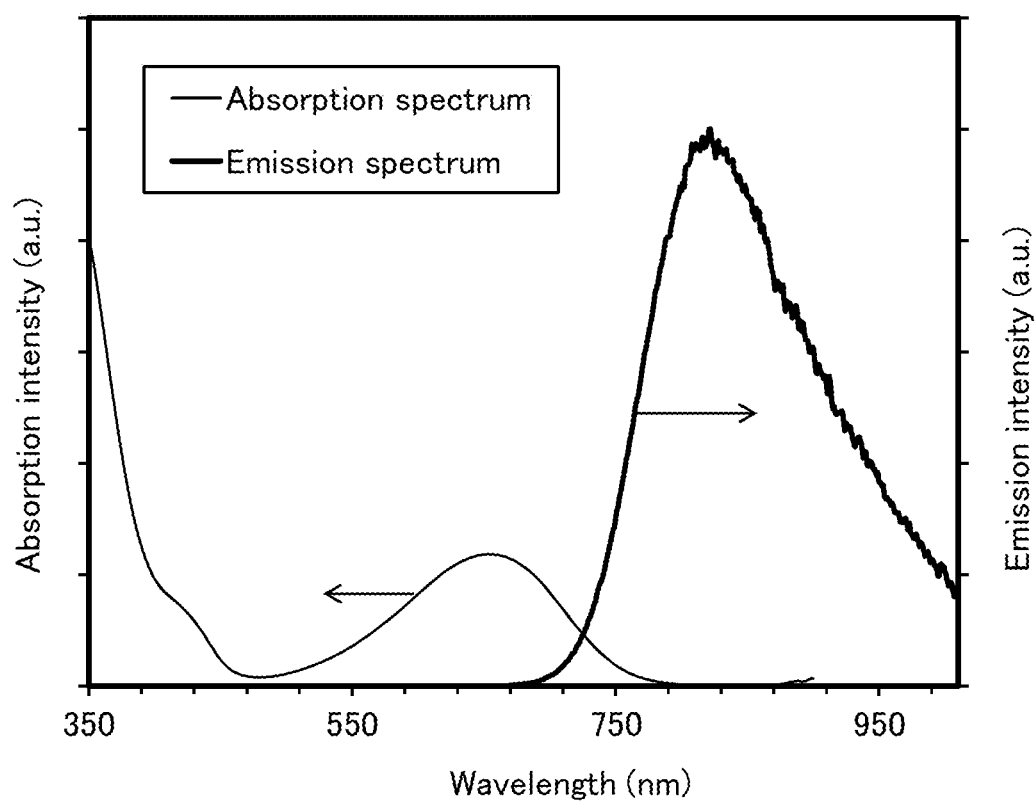
FIG. 13 shows an ultraviolet-visible absorption spectrum and an emission spectrum of the organic compound represented by Structural Formula (300)

The absorption spectrum was measured with an ultraviolet-visible spectrophotometer (V-550, produced by JASCO Corporation). The emission spectrum was measured with a fluorescence spectrophotometer (FP-8600, produced by JASCO Corporation). FIG. 13 shows the obtained absorption and emission spectra of the toluene solution. The horizontal axis represents wavelength, and the vertical axis represents intensity.

The results in FIG. 13 show that PCAP2TDQn in the toluene solution has an absorption peak at around 654 nm and an emission peak at around 821 nm (excitation wavelength: 654 nm).

The HOMO level and the LUMO level of PCAP2TDQn were obtained through a cyclic voltammetry (CV) measurement. The same measurement method and calculation method as those used in Example 1 were used here.

[Chemical Formula 51]

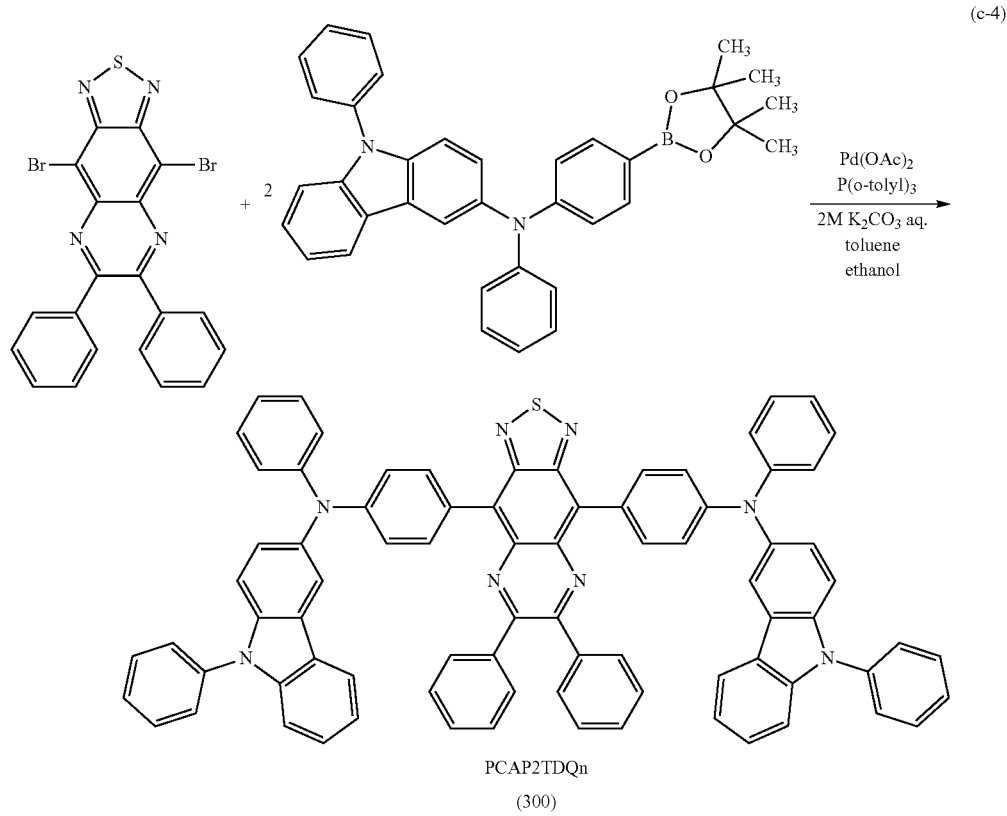

Figure 12:
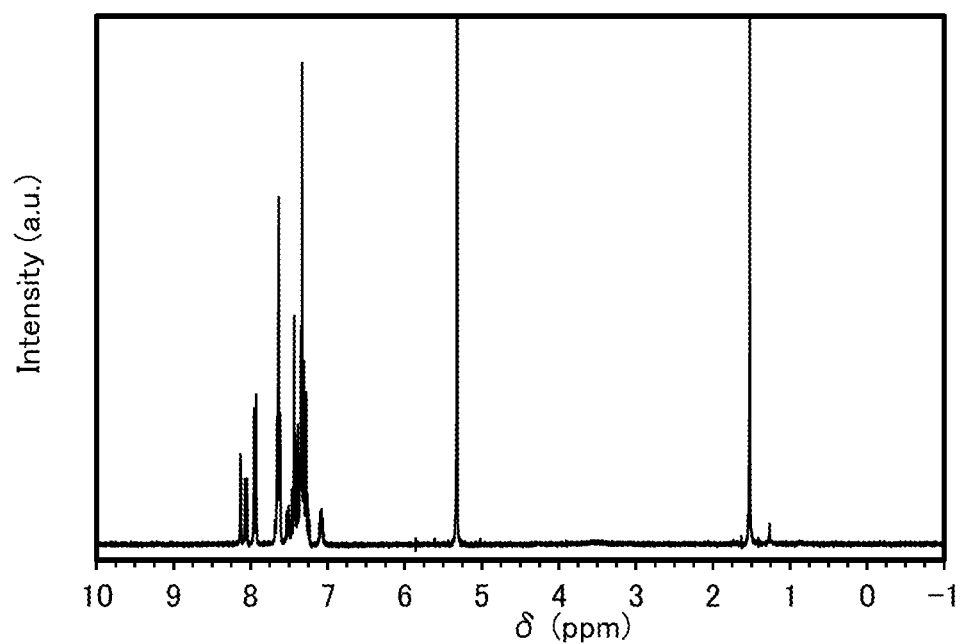
FIG. 12 is a $^1$H-NMR chart of an organic compound represented by Structural Formula (300)

Analysis results by nuclear magnetic resonance ($^1$H-NMR) spectroscopy of the blue-green solid obtained by the above reaction are shown below. A $^1$H-NMR chart is shown in FIG. 12. These results reveal that PCAP2TDQn, the organic compound of one embodiment of the present invention represented by Structural Formula (300), was obtained in this example.

$^1$H NMR (dichloromethane-d$_2$, 300 MHz): δ=8.13 (d, J=1.8 Hz, 2H), 8.06 (d, J=7.8 Hz, 2H), 7.94 (d, J=9.3 Hz, 4H), 7.68-7.61 (m, 12H), 7.53-7.23 (m, 30H), 7.11-7.05 (m, 2H).

As a result, in the measurement of the oxidation potential Ea [V] of PCAP2TDQn, the HOMO level was found to be −5.34 eV. In contrast, the LUMO level was found to be −3.79 eV in the measurement of the reduction potential Ec [V]. When the oxidation-reduction wave was repeatedly measured, in the Ea measurement, the peak intensity of the oxidation-reduction wave in the hundredth cycle was maintained to be 94% of that of the oxidation-reduction wave in the first cycle, and in the Ec measurement, the peak intensity of the oxidation-reduction wave in the hundredth cycle was maintained to be 92% of that of the oxidation-reduction wave in the first cycle; thus, resistance to oxidation and reduction of PCAP2TDQn was found to be extremely high.

Example 4

Figure 14:
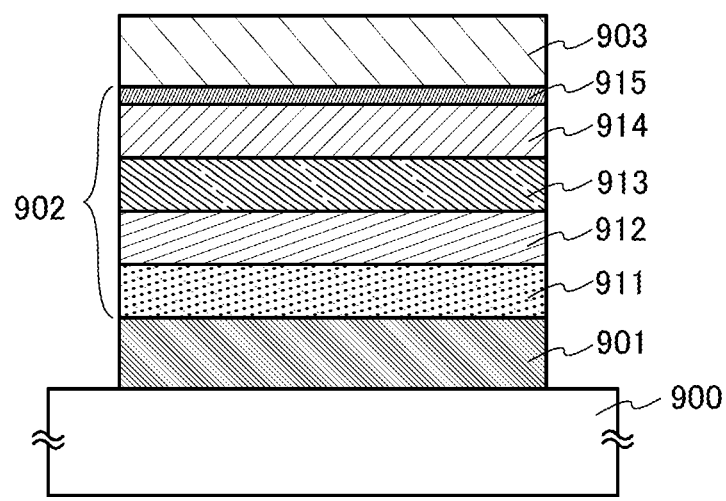
FIG. 14 is a view illustrating a light-emitting device.

In this example, device structures, manufacturing methods, and operation characteristics of light-emitting devices of embodiments of the present invention, a light-emitting device 1, a light-emitting device 2, and a light-emitting device 3, each of which uses N,N'-bis[4-(9H-carbazol-9-yl)phenyl]-N,N',6,7-tetraphenyl-[1,2,5]thiadiazolo[3,4-g]quinoxaline-4,9-diamine (abbreviation: YGA2TDQn) (Structural Formula (100)) described in Example 1 for its light-emitting layer, will be described. Note that the light-emitting device 1 is a fluorescent light-emitting device having a structure causing triplet-triplet annihilation (TTA) in its light-emitting layer. The light-emitting device 2 is a fluorescent light-emitting device having a structure of supplying excitation energy from an exciplex to a fluorescent substance in its light-emitting layer. The light-emitting device 3 is a fluorescent light-emitting device having a structure of supplying excitation energy from a substance exhibiting thermally activated delayed fluorescence (TADF material) to a fluorescent substance. The device structure of the light-emitting devices used in this example is illustrated in FIG. 14, and specific structures are shown in Table 1. The chemical formulae of materials used in this example are shown below.

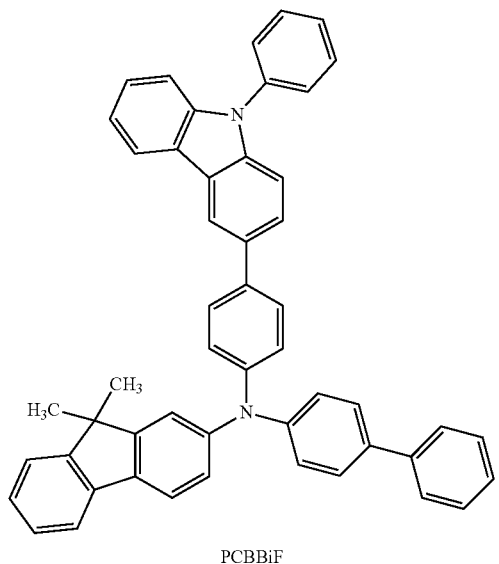

PCBBiF

TABLE 1

| | First electrode 901 | Hole-injection layer 911 | Hole-transport layer 912 | Light-emitting layer 913 | Electron-transport layer 914 | | Electron-injection layer 915 | Second electrode 903 |
|---|---|---|---|---|---|---|---|---|
| Light-emitting device 1 | ITSO (70 nm) | DBT3P-II:MoOx (1:0.5 110 nm) | PCBBiF (20 nm) | * | 4,6mCzP2Pm (20 nm) | NBphen (70 nm) | LiF (1 nm) | Al (200 nm) |
| Light-emitting device 2 | ITSO (70 nm) | DBT3P-II:MoOx (1:0.5 110 nm) | PCCP (20 nm) | ** | 4,6mCzP2Pm (20 nm) | NBphen (70 nm) | LiF (1 nm) | Al (200 nm) |
| Light-emitting device 3 | ITSO (70 nm) | DBT3P-II:MoOx (1:0.5 110 nm) | PCCP (20 nm) | *** | 4,6mCzP2Pm (20 nm) | NBphen (70 nm) | LiF (1 nm) | Al (200 nm) |

* cgDBCzPA:Rubrene:YGA2TDQn (0.5:0.5:0.05 30 nm)
** 4,6mCzP2Pm:[Ir(ppz)$_3$]:YGA2TDQn (0.8:0.2:0.05 30 nm)
*** 4,6mCzP2Pm:2,3CN-7,10TPA2DBq:YGA2TDQn (0.5:0.5:0.05 30 nm)

[Chemical Formulae 52]

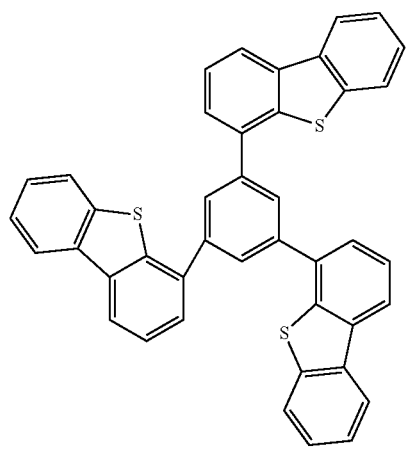

DBT3P-II

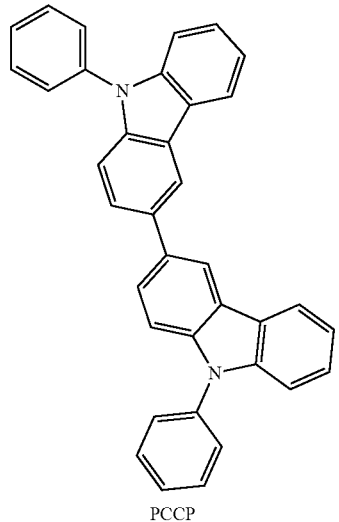

PCCP

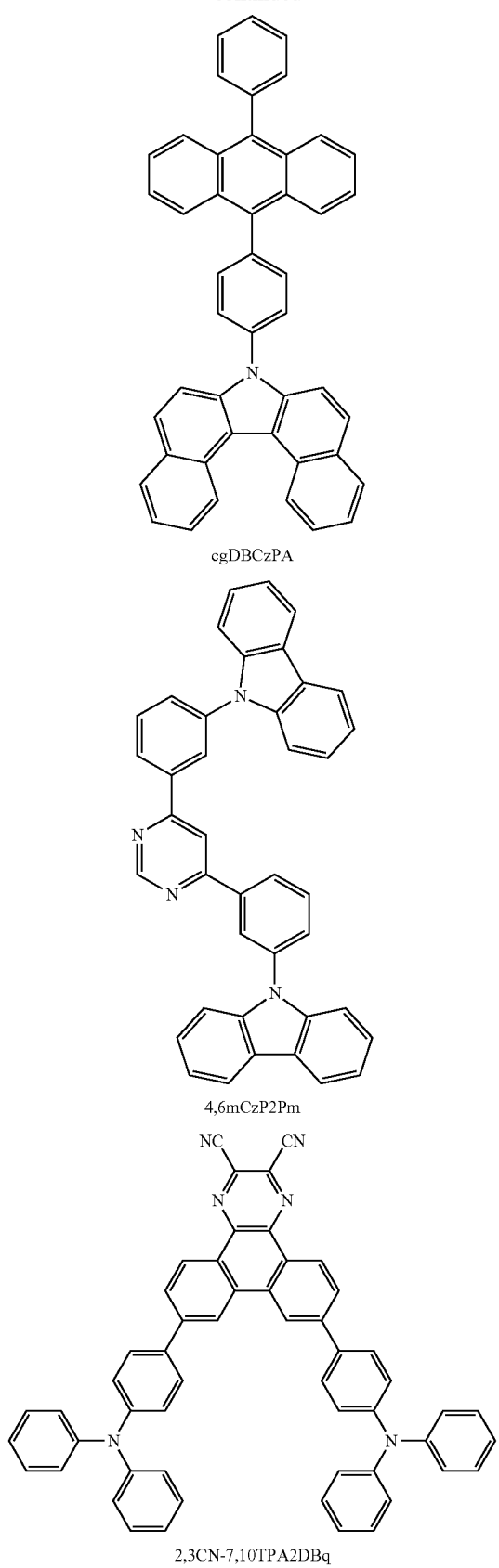

cgDBCzPA 4,6mCzP2Pm 2,3CN-7,10TPA2DBq

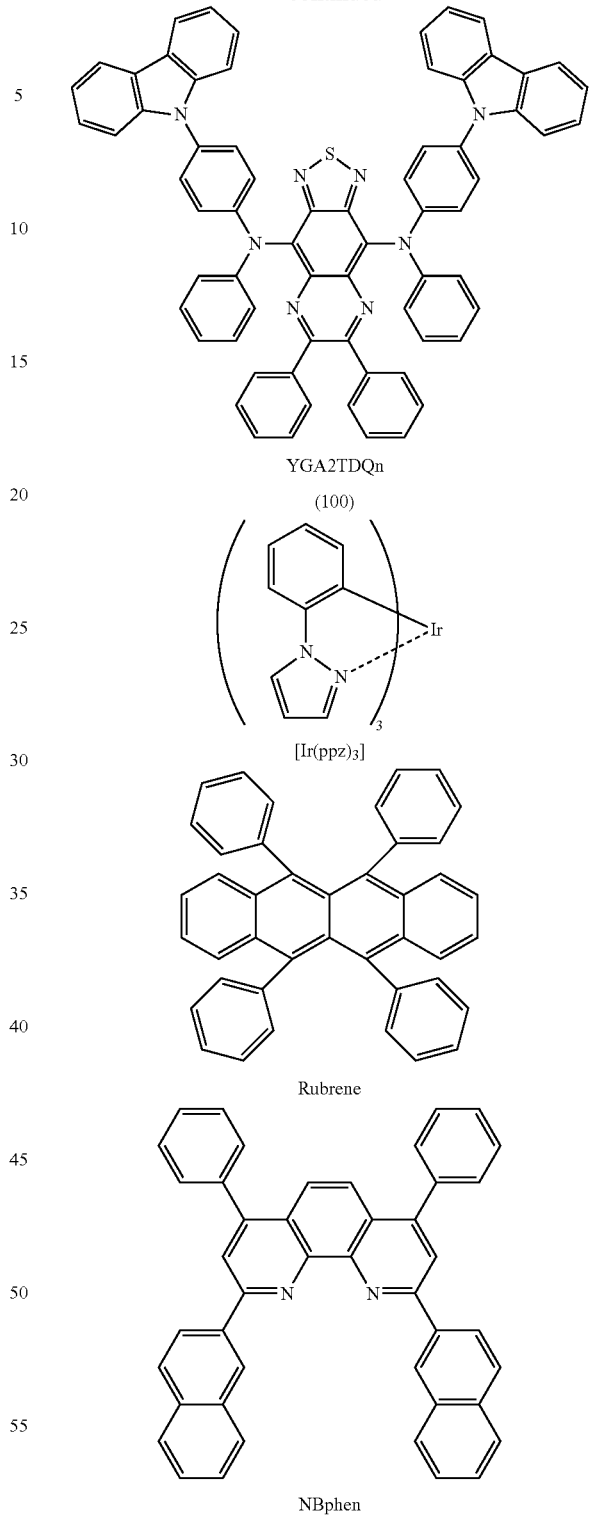

YGA2TDQn

[Ir(ppz)₃]

Rubrene

NBphen

<<Fabrication of Light-Emitting Devices>>

In each of the light-emitting devices described in this example, as illustrated in FIG. 14, a hole-injection layer 911, a hole-transport layer 912, a light-emitting layer 913, an electron-transport layer 914, and an electron-injection layer 915 are stacked in this order over a first electrode 901 formed over a substrate 900, and a second electrode 903 is stacked over the electron-injection layer 915.

First, the first electrode 901 was formed over the substrate 900. The electrode area was set to 4 mm² (2 mm×2 mm). A glass substrate was used as the substrate 900. The first electrode 901 was formed to a thickness of 70 nm using indium tin oxide containing silicon oxide (ITSO) by a sputtering method.

For pretreatment, a surface of the substrate was washed with water, baking was performed at 200° C. for 1 hour, and then UV ozone treatment was performed for 370 seconds. After that, the substrate was transferred into a vacuum evaporation apparatus where the pressure had been reduced to approximately $1 \times 10^{-4}$ Pa, and was subjected to vacuum baking at 170° C. for 30 minutes in a heating chamber of the vacuum evaporation apparatus, and then the substrate was cooled down for approximately 30 minutes.

Next, the hole-injection layer 911 was formed over the first electrode 901. After the pressure in the vacuum evaporation apparatus was reduced to $1 \times 10^{-4}$ Pa, the hole-injection layer 911 was formed by co-evaporation to have a mass ratio of 1,3,5-tri(dibenzothiophen-4-yl)benzene (abbreviation: DBT3P-II) to molybdenum oxide of 1:0.5 and a thickness of 110 nm.

Then, the hole-transport layer 912 was formed over the hole-injection layer 911. For the light-emitting device 1, the hole-transport layer 912 was formed to a thickness of 20 nm by evaporation of N-(1,1'-biphenyl-4-yl)-9,9-dimethyl-N-[4-(9-phenyl-9H-carbazol-3-yl)phenyl]-9H-fluoren-2-amine (abbreviation: PCBBiF). For the light-emitting device 2 and the light-emitting device 3, the hole-transport layer 912 was formed to a thickness of 20 nm by evaporation of 3,3'-bis (9-phenyl-9H-carbazole) (abbreviation: PCCP).

Next, the light-emitting layer 913 was formed over the hole-transport layer 912.

For the light-emitting device 1, the light-emitting layer 913 was formed by co-evaporation of 7-[4-(10-phenyl-9-anthryl)phenyl]-7H-dibenzo[c,g]carbazole (abbreviation: cgDBCzPA), rubrene, and YGA2TDQn to have a weight ratio of cgDBCzPA:rubrene:YGA2TDQn=0.5:0.5:0.05. The thickness was set to 30 nm. For the light-emitting device 2, the light-emitting layer 913 was formed by co-evaporation of 9,9'-(pyrimidine-4,6-diyldi-3,1-phenylene)bis(9H-carbazole) (abbreviation: 4,6mCzP2Pm), tris[2-(1H-pyrazol-1-yl-κN2)phenyl-κC]iridium(III) (abbreviation: [Ir(ppz)₃], and YGA2TDQn to have a weight ratio of 4,6mCzP2Pm:[Ir (ppz)₃]:YGA2TDQn=0.8:0.2:0.05. The thickness was set to 30 nm. For the light-emitting device 3, the light-emitting layer 913 was formed by co-evaporation of 4,6mCzP2Pm, 4,4'-(2,3-dicyanodibenzo[f,h]quinoxaline-7,10-diyl)bis(triphenylamine) (abbreviation: 2,3CN-7,10TPA2DBq), and YGA2TDQn to have a weight ratio of 4,6mCzP2Pm:2,3CN-7,10TPA2DBq:YGA2TDQn=0.5:0.5:0.05. The thickness was set to 30 nm.

Next, the electron-transport layer 914 was formed over the light-emitting layer 913.

The electron-transport layer 914 was formed in such a manner that 4,6mCzP2Pm and 2,9-bis(naphthalen-2-yl)-4, 7-diphenyl-1,10-phenanthroline (abbreviation: NBphen) were sequentially deposited by evaporation to thicknesses of 20 nm and 15 nm, respectively.

Then, the electron-injection layer 915 was formed over the electron-transport layer 914. The electron-injection layer 915 was formed to a thickness of 1 nm by evaporation of lithium fluoride (LiF).

After that, the second electrode 903 was formed over the electron-injection layer 915. The second electrode 903 was formed to a thickness of 200 nm by an evaporation method using aluminum. In this example, the second electrode 903 functions as a cathode.

Through the above steps, the light-emitting devices each including an EL layer 902 between the pair of electrodes were formed over the substrate 900. Note that the hole-injection layer 911, the hole-transport layer 912, the light-emitting layer 913, the electron-transport layer 914, and the electron-injection layer 915 described above are functional layers forming the EL layer in one embodiment of the present invention. Furthermore, in all the evaporation steps in the above fabrication method, evaporation was performed by a resistance-heating method.

Each of the light-emitting devices fabricated as described above was sealed using another substrate (not illustrated) in such a manner that the substrate (not illustrated) to which a sealant to be cured by ultraviolet light was applied was fixed to the substrate 900 in a glove box containing a nitrogen atmosphere, and the substrates were bonded to each other such that the sealant was attached so as to surround the light-emitting device formed over the substrate 900. In the sealing process, the sealant was irradiated with 365-nm ultraviolet light at 6 J/cm² to be cured, and the sealant was heated at 80° C. for 1 hour to be stabilized.

<<Operation Characteristics of Light-Emitting Devices>>

Figure 15:
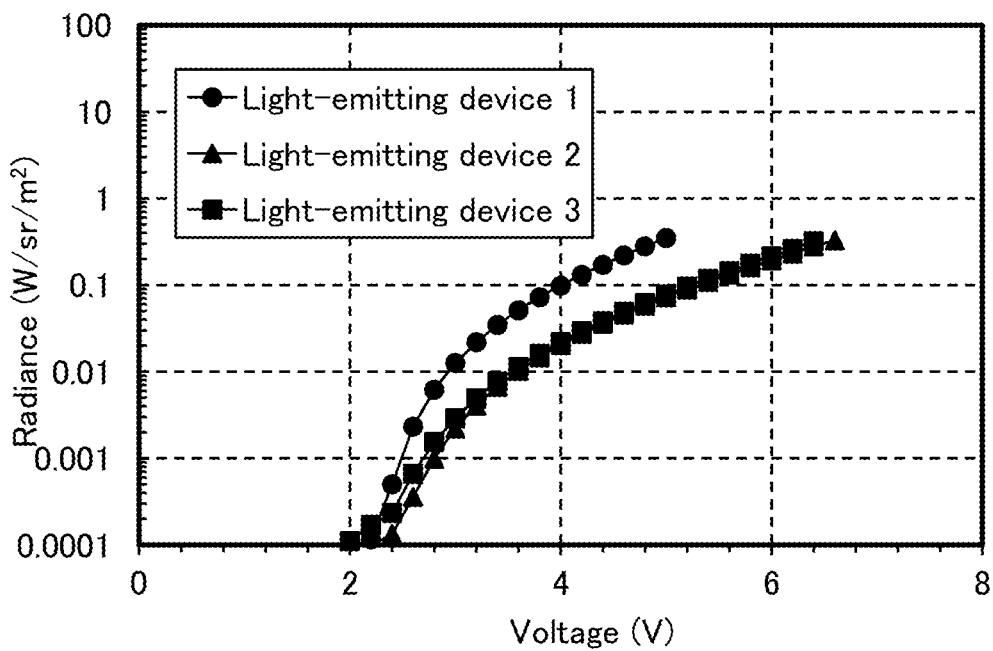
FIG. 15 shows the voltage-radiance characteristics of a light-emitting device 1, a light-emitting device 2, and a light-emitting device 3.
Figure 16:
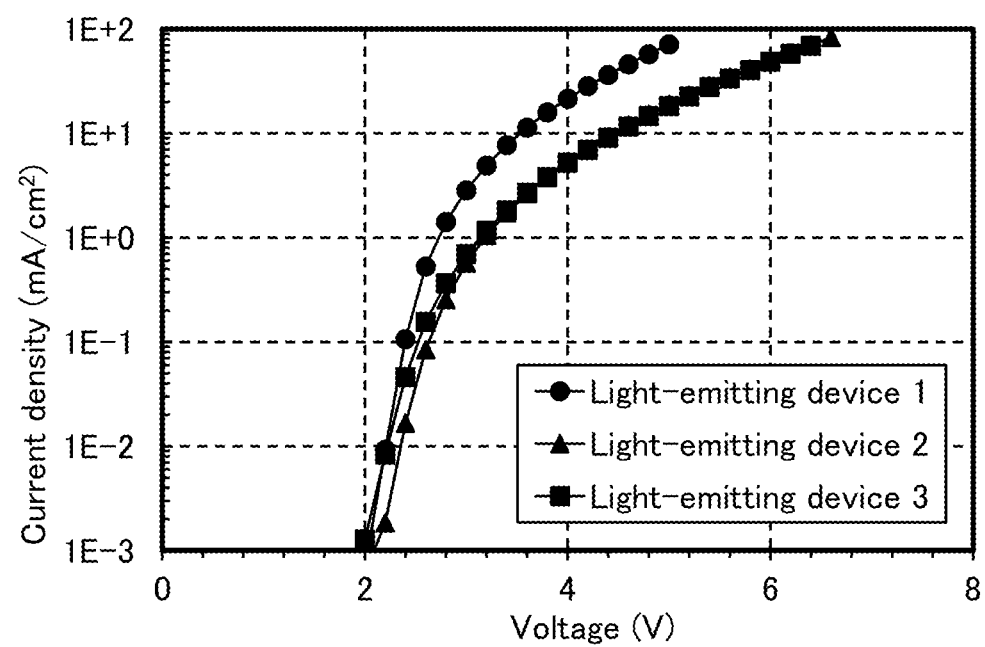
FIG. 16 shows the voltage-current density characteristics of the light-emitting device 1, the light-emitting device 2, and the light-emitting device 3.
Figure 17:
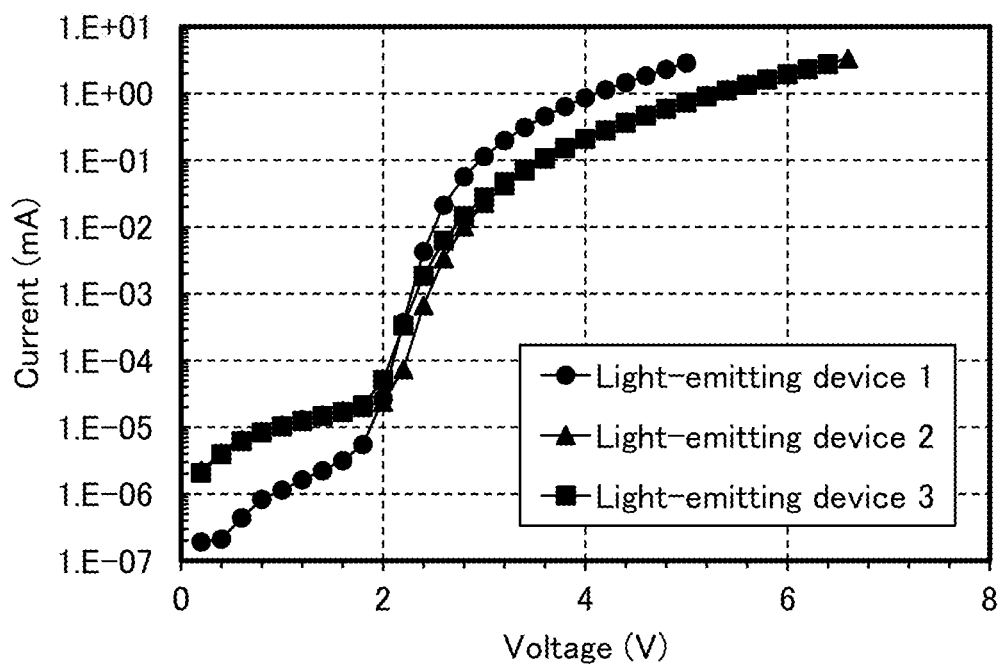
FIG. 17 shows the voltage-current characteristics of the light-emitting device 1, the light-emitting device 2, and the light-emitting device 3.

Operation characteristics of the fabricated light-emitting devices were measured. Note that the measurement was performed at room temperature (in an atmosphere kept at 25° C.). As the results of the operation characteristic measurement of the light-emitting devices, the voltage-radiance characteristics are shown in FIG. 15, the voltage-current density characteristics are shown in FIG. 16, and the voltage-current characteristics are shown in FIG. 17.

Table 2 shows the initial values of main characteristics of the light-emitting devices at around 11 mA/cm².

TABLE 2

|  | Voltage (V) | Current (mA) | Current density (mA/cm²) | Radiance (W/sr/m²) |
| --- | --- | --- | --- | --- |
| Light-emitting device 1 | 3.6 | 0.45 | 11 | 0.051 |
| Light-emitting device 2 | 4.6 | 0.48 | 12 | 0.046 |
| Light-emitting device 3 | 4.6 | 0.46 | 12 | 0.049 |

Figure 18:
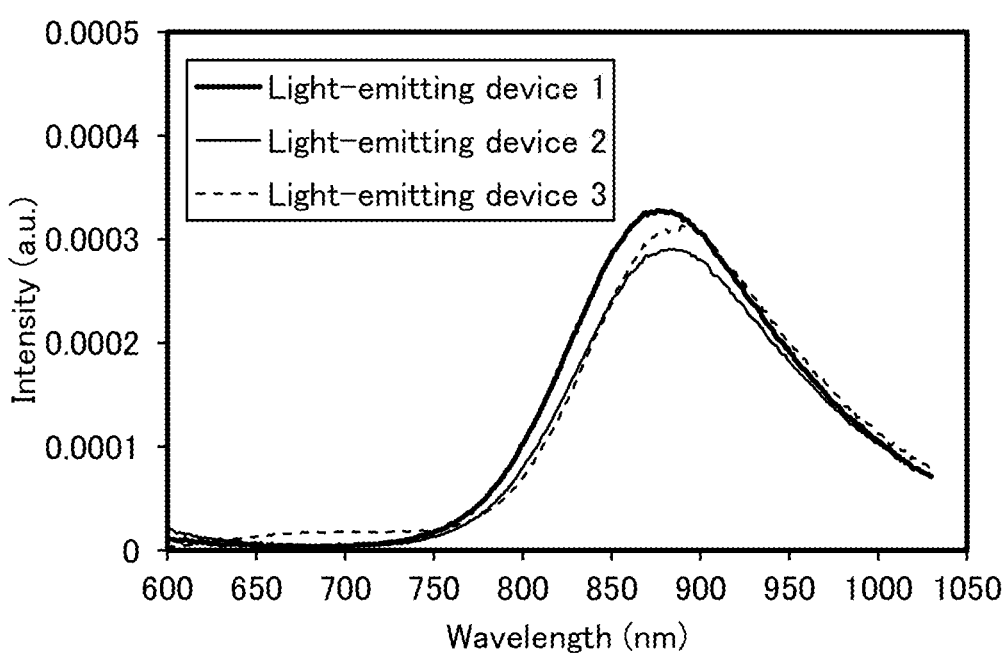
FIG. 18 shows the emission spectra of the light-emitting device 1, the light-emitting device 2, and the light-emitting device 3.

FIG. 18 shows emission spectra when current at a current density of 11 mA/cm² was supplied to each of the light-emitting devices. As shown in FIG. 18, the emission spectra of the light-emitting devices 1 to 3 each have a peak at around 879 nm, which is presumably derived from light emission of YGA2TDQn contained in the light-emitting layer 913.

Example 5

In this example, device structures and operation characteristics of light-emitting devices of embodiments of the present invention, a light-emitting device 4 and a light-emitting device 5, each of which uses N,N'-bis(9-phenyl-9H-carbazol-4-yl)-N,N',6,7-tetraphenyl-[1,2,5]thiadiazolo [3,4-g]quinoxaline-4,9-diamine (abbreviation: PCA2TDQn) (Structural Formula (200)) described in Example 2 for its light-emitting layer, will be described. Note that the light-emitting device 4 is a fluorescent light-emitting device having a structure causing triplet-triplet annihilation (TTA) in its light-emitting layer. The light-emitting device 5 is a fluorescent light-emitting device having a structure of supplying excitation energy from a substance exhibiting thermally activated delayed fluorescence (TADF material) to a fluorescent substance.

The device structures of the light-emitting devices 4 and 5 fabricated in this example are similar to the structure of FIG. 14 described in Example 4, and specific structures of the layers forming the device structure are shown in Table 3. The chemical formulae of materials used in this example are shown below.

TABLE 3

|  | First electrode 901 | Hole-injection layer 911 | Hole-transport layer 912 | Light-emitting layer 913 | Electron-transport layer 914 | Electron-injection layer 915 | Second electrode 903 |
|---|---|---|---|---|---|---|---|
| Light-emitting device 4 | ITSO (70 nm) | DBT3P-II:MoOx (1:0.5 110 nm) | PCCP (20 nm) | * | 4,6mCzP2Pm (20 nm) NBphen (70 nm) | LiF (1 nm) | Al (200 nm) |
| Light-emitting device 5 | ITSO (70 nm) | DBT3P-II:MoOx (1:0.5 110 nm) | PCCP (20 nm) | ** | 4,6mCzP2Pm (20 nm) NBphen (70 nm) | LiF (1 nm) | Al (200 nm) |

* cgDBCzPA:Rubrene:PCA2TDQn (0.5:0.5:0.05 30 nm)
** 4,6mCzP2Pm:2,3CN-7,10TPA2DBq:PCA2TDQn (0.5:0.5:0.05 30 nm)

[Chemical Formulae 53]

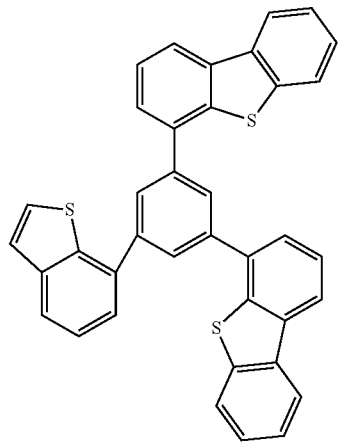

DBT3P-II

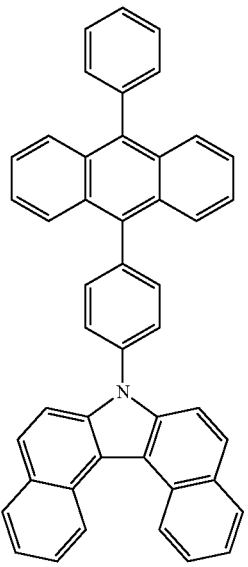

cgDBCzPA

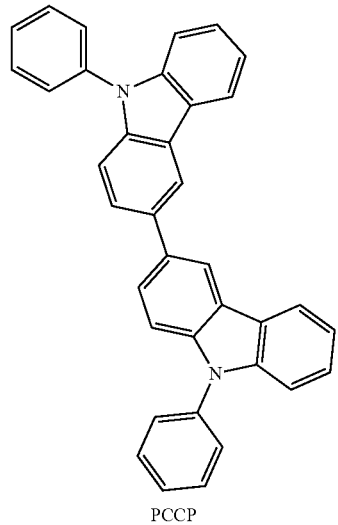

PCCP

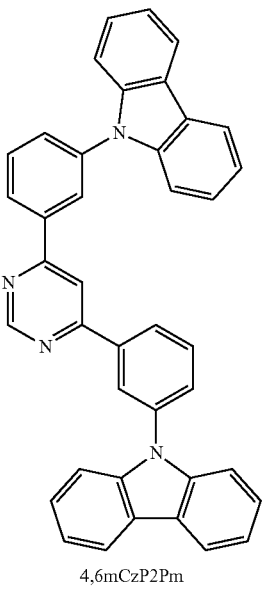

4,6mCzP2Pm

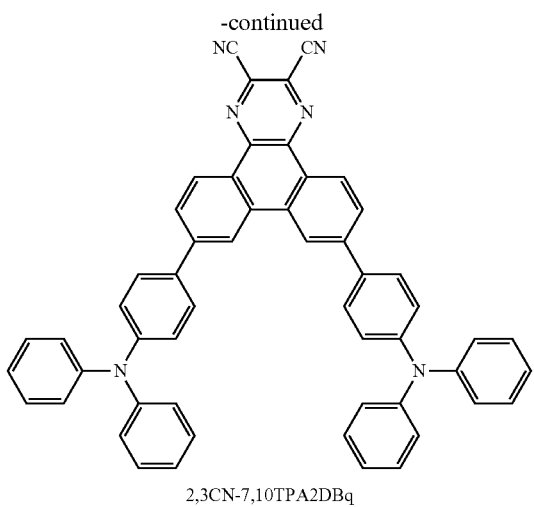

2,3CN-7,10TPA2DBq

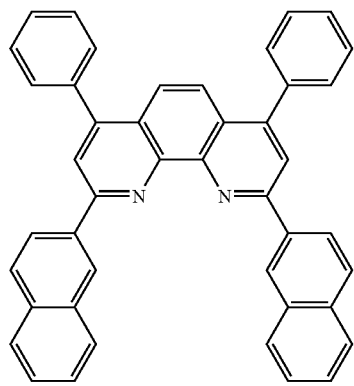

NBphen

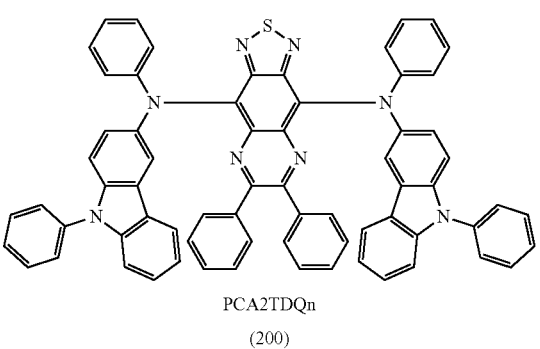

PCA2TDQn
(200)

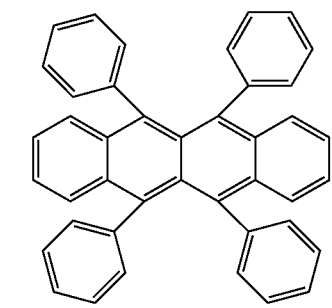

Rubrene

<<Operation Characteristics of Light-Emitting Devices>>

Figure 19:
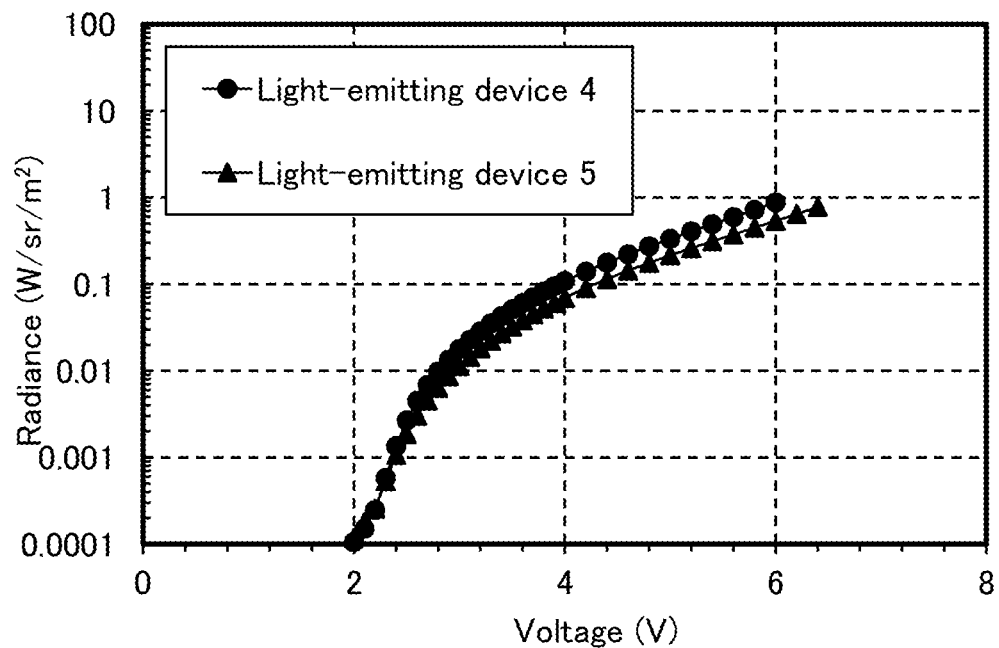
FIG. 19 shows the voltage-radiance characteristics of a light-emitting device 4 and a light-emitting device 5.
Figure 20:
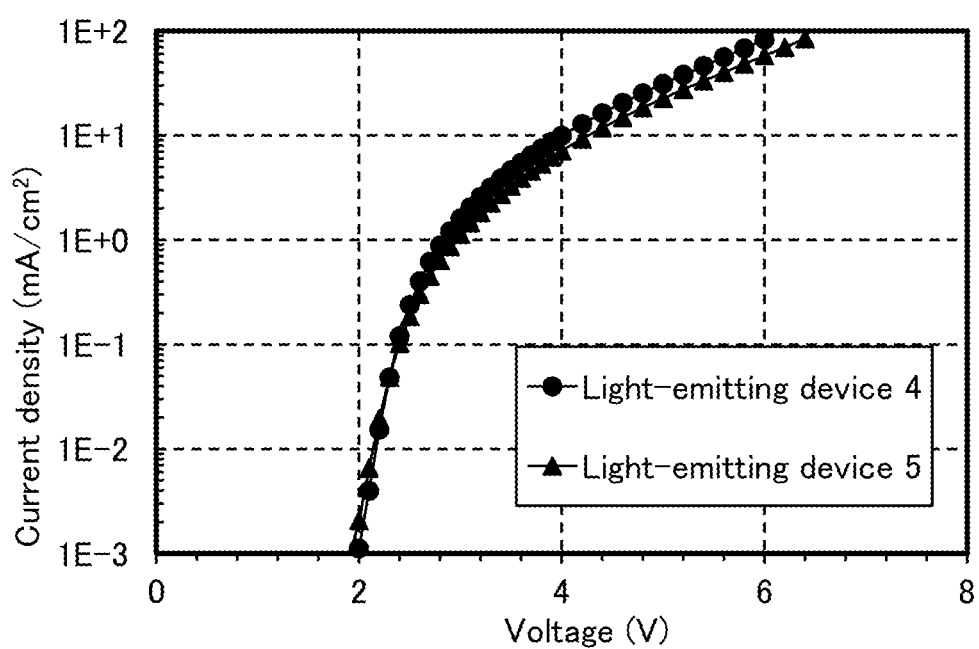
FIG. 20 shows the voltage-current density characteristics of the light-emitting device 4 and the light-emitting device 5.
Figure 21:
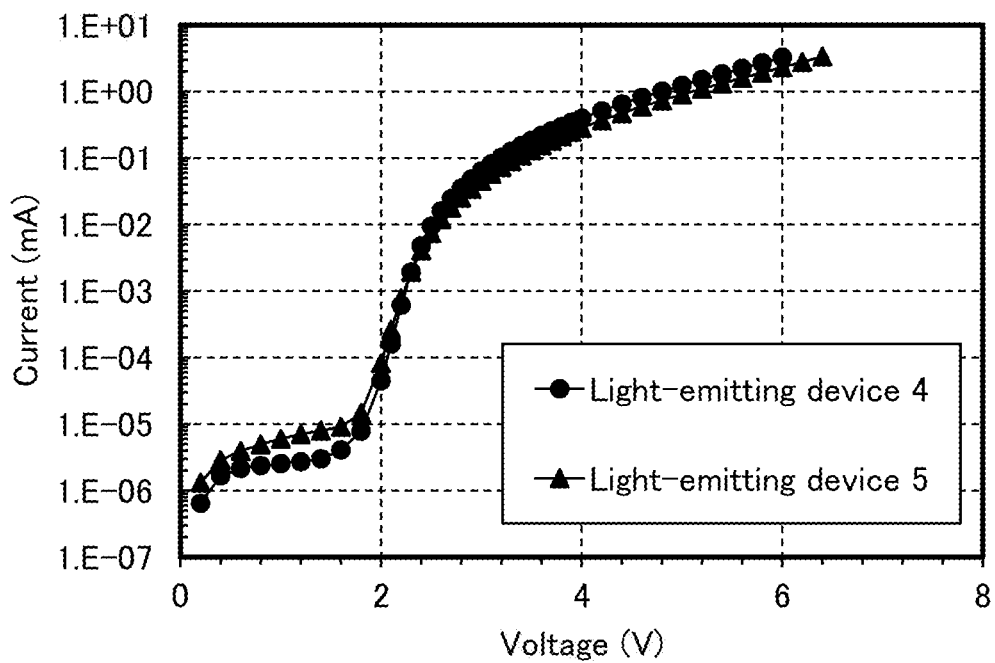
FIG. 21 shows the voltage-current characteristics of the light-emitting device 4 and the light-emitting device 5.

Operation characteristics of the fabricated light-emitting devices were measured. Note that the measurement was performed at room temperature (in an atmosphere kept at 25° C.). As the results of the operation characteristic measurement of the light-emitting devices, the voltage-radiance characteristics are shown in FIG. 19, the voltage-current density characteristics are shown in FIG. 20, and the voltage-current characteristics are shown in FIG. 21.

Table 4 shows the initial values of main characteristics of the light-emitting devices at around 12 mA/cm$^2$.

TABLE 4

| | Voltage (V) | Current (mA) | Current density (mA/cm$^2$) | Radiance (W/sr/m$^2$) |
| --- | --- | --- | --- | --- |
| Light-emitting device 4 | 4.2 | 0.51 | 13 | 0.14 |
| Light-emitting device 5 | 4.4 | 0.47 | 12 | 0.11 |

Figure 22:
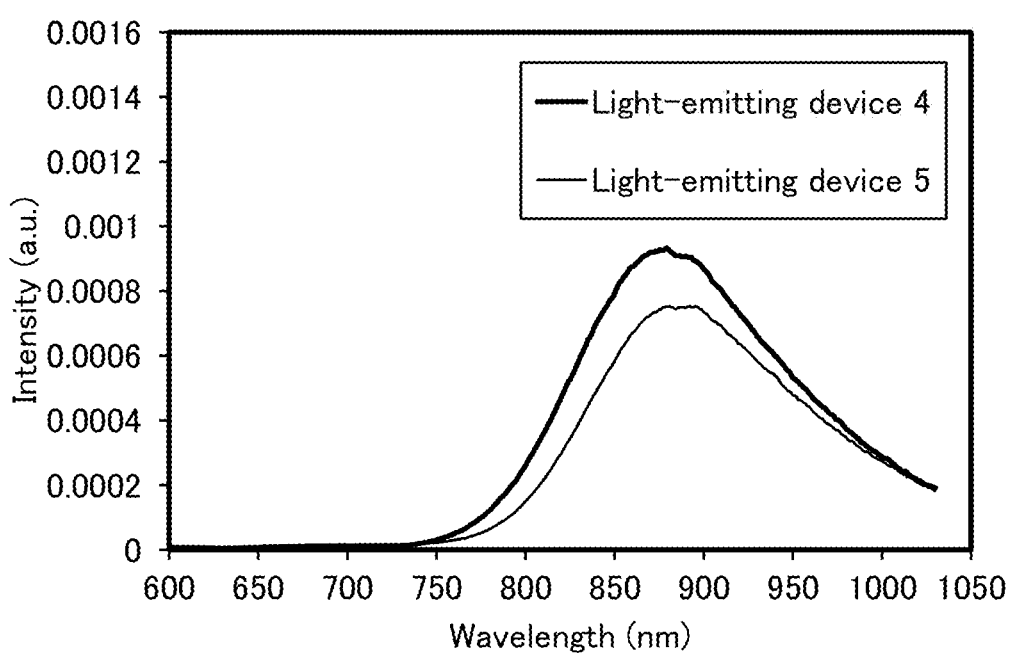
FIG. 22 shows the emission spectra of the light-emitting device 4 and the light-emitting device 5.

FIG. 22 shows emission spectra when current at a current density of 12 mA/cm$^2$ was supplied to the light-emitting devices. As shown in FIG. 22, the emission spectrum of each of the light-emitting devices has a peak at around 893 nm, which is presumably derived from light emission of PCA2TDQn contained in the light-emitting layer 913.

Example 6

In this example, a device structure and operation characteristics of a light-emitting device of one embodiment of the present invention, a light-emitting device 6, which uses N,N-[(6,7-diphenyl[1,2,5]thiadiazolo[3,4-g]quinoxaline-4,9-diyl)di-4,1-phenylene]bis(N,9-diphenyl-9H-carbazol-3-amine) (abbreviation: PCAP2TDQn) (Structural Formula (300)) for its light-emitting layer will be described. The light-emitting device 6 is a fluorescent light-emitting device having a structure of supplying excitation energy from a substance exhibiting thermally activated delayed fluorescence (TADF material) to a fluorescent substance in its light-emitting layer.

The device structure of the light-emitting device 6 fabricated in this example is similar to the structure of FIG. 14 described in Example 4, and specific structures of the layers forming the device structure are shown in Table 5. The chemical formulae of materials used in this example are shown below.

TABLE 5
| | First electrode 901 | Hole-injection layer 911 | Hole-transport layer 912 | Light-emitting layer 913 | Electron-transport layer 914 | Electron-injection layer 915 | Second electrode 903 |
|---|---|---|---|---|---|---|---|
| Light-emitting device 6 | ITSO (70 nm) | DBT3P-II:MoOx (1:0.5 110 nm) | PCCP (20 nm) | * | 4,6mCzP2Pm (20 nm) | NBphen (70 nm) | LiF (1 nm) / Al (200 nm) |
* 4,6mCzP2Pm:2,3CN-7,10TPA2DBq:PCAP2TDQn (0.8:0.2:0.05 30 nm)
[Chemical Formulae 54]
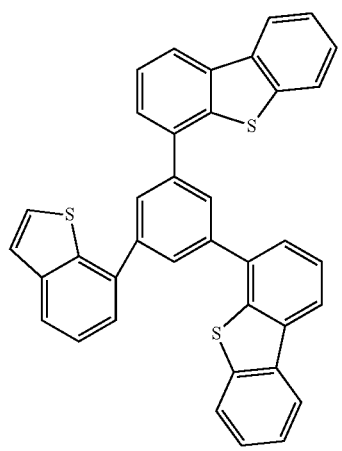
DBT3P-II
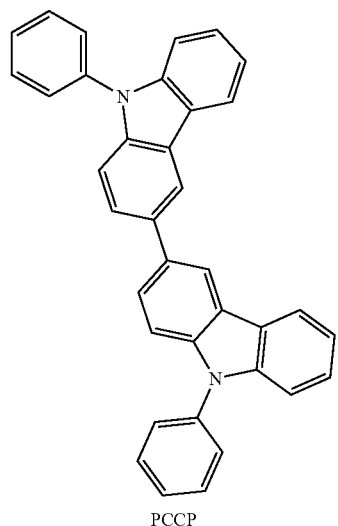
PCCP
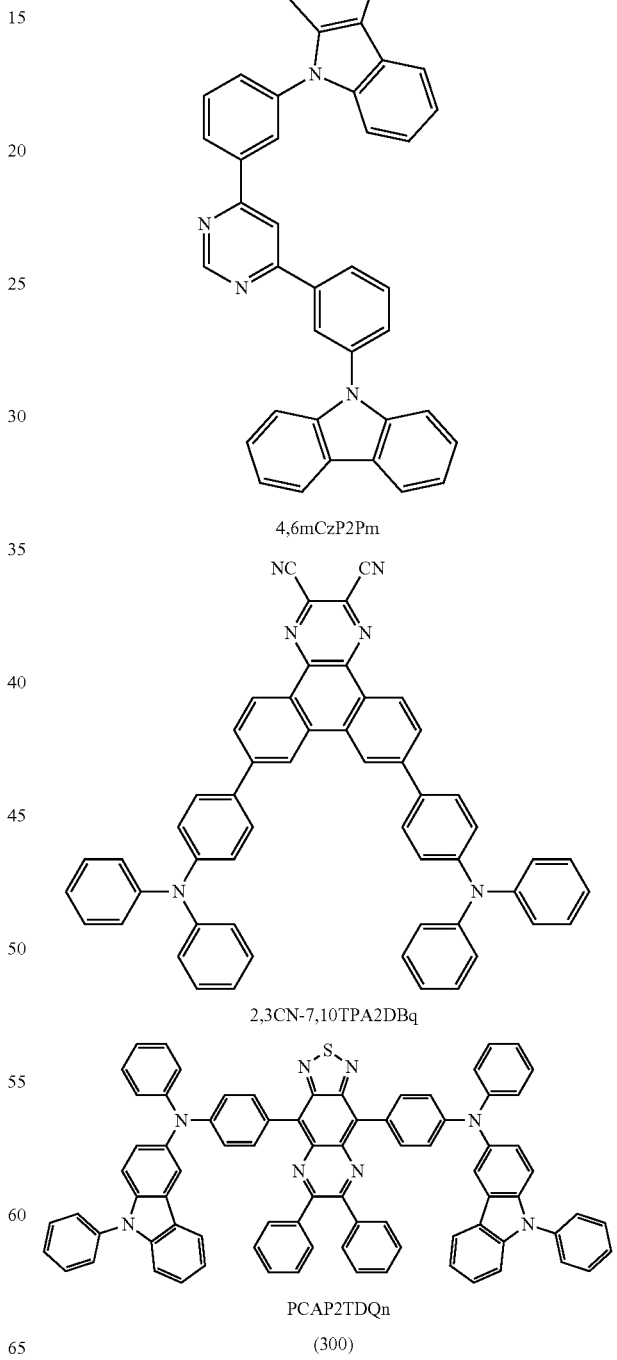
4,6mCzP2Pm
2,3CN-7,10TPA2DBq
PCAP2TDQn
(300)

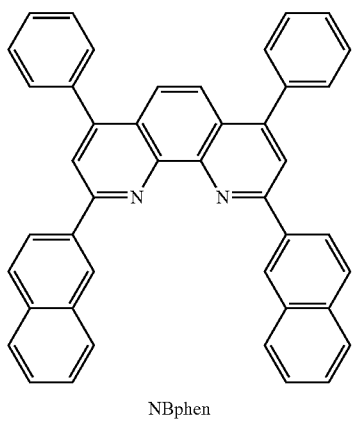

NBphen

Figure 23:
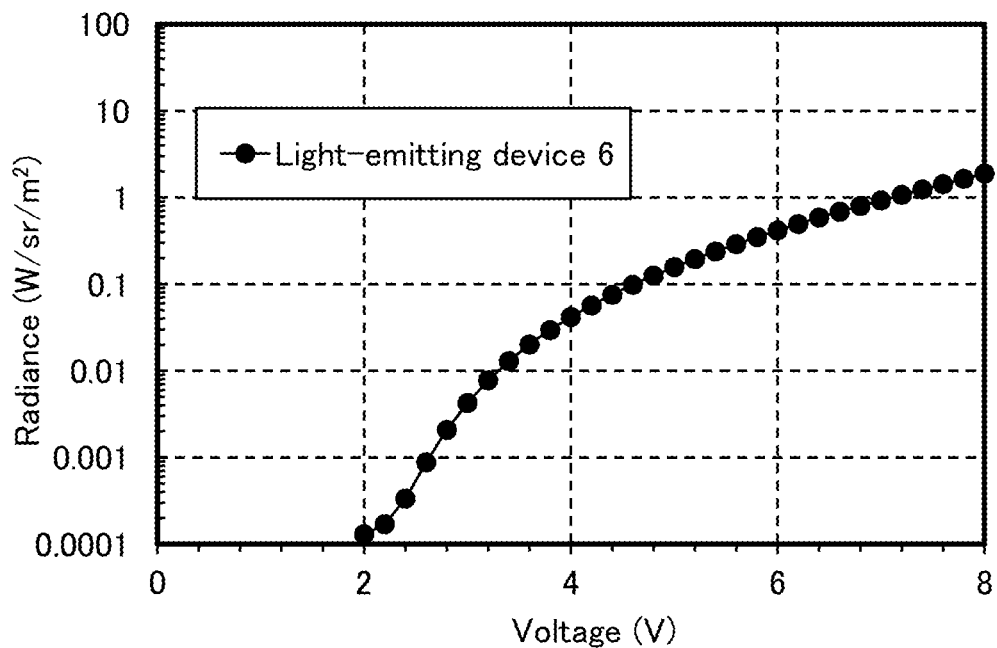
FIG. 23 shows the voltage-radiance characteristics of a light-emitting device 6.
Figure 24:
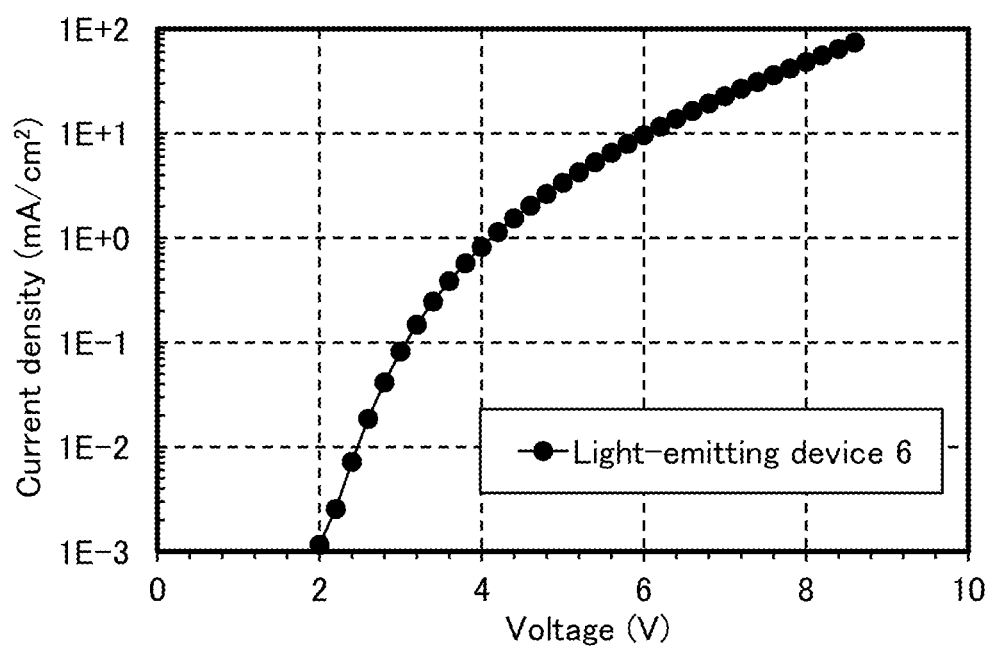
FIG. 24 shows the voltage-current density characteristics of the light-emitting device 6.
Figure 25:
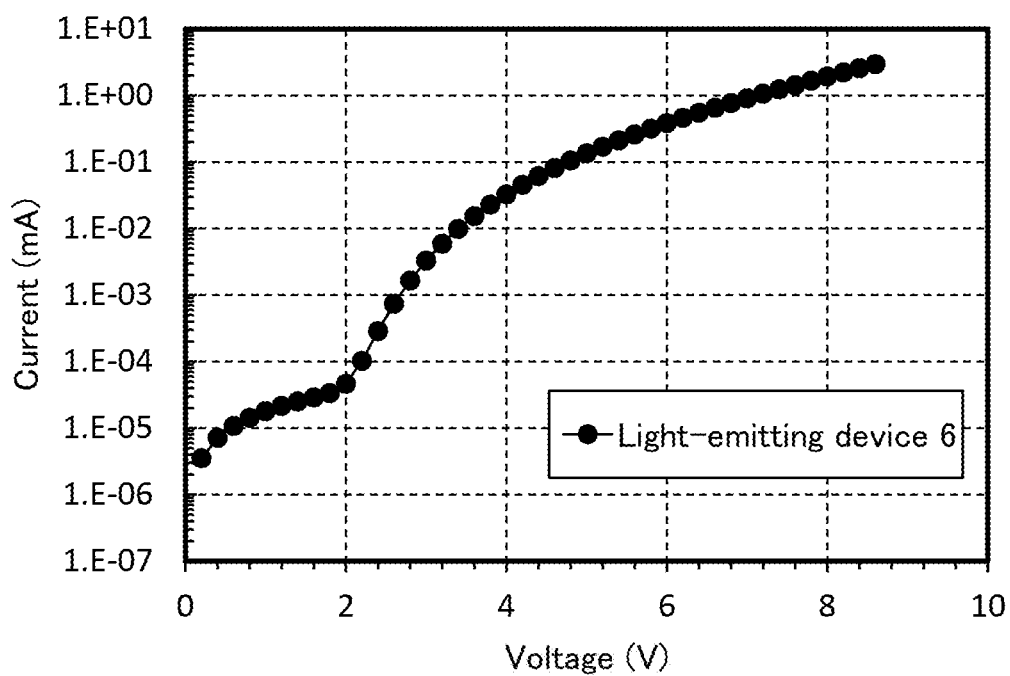
FIG. 25 shows the voltage-current characteristics of the light-emitting device 6.

Operation characteristics of the fabricated light-emitting device 6 were measured. Note that the measurement was performed at room temperature (in an atmosphere kept at 25° C.). As the results of the operation characteristic measurement of the light-emitting device 6, the voltage-radiance characteristics are shown in FIG. 23, the voltage-current density characteristics are shown in FIG. 24, and the voltage-current characteristics are shown in FIG. 25.

Table 6 shows the initial values of main characteristics of the light-emitting device 6 at around 12 mA/cm².

TABLE 6

| | Voltage (V) | Current (mA) | Current density (mA/cm²) | Radiance (W/sr/m²) |
|---|---|---|---|---|
| Light-emitting device 6 | 6.2 | 0.46 | 12 | 0.50 |

Figure 26:
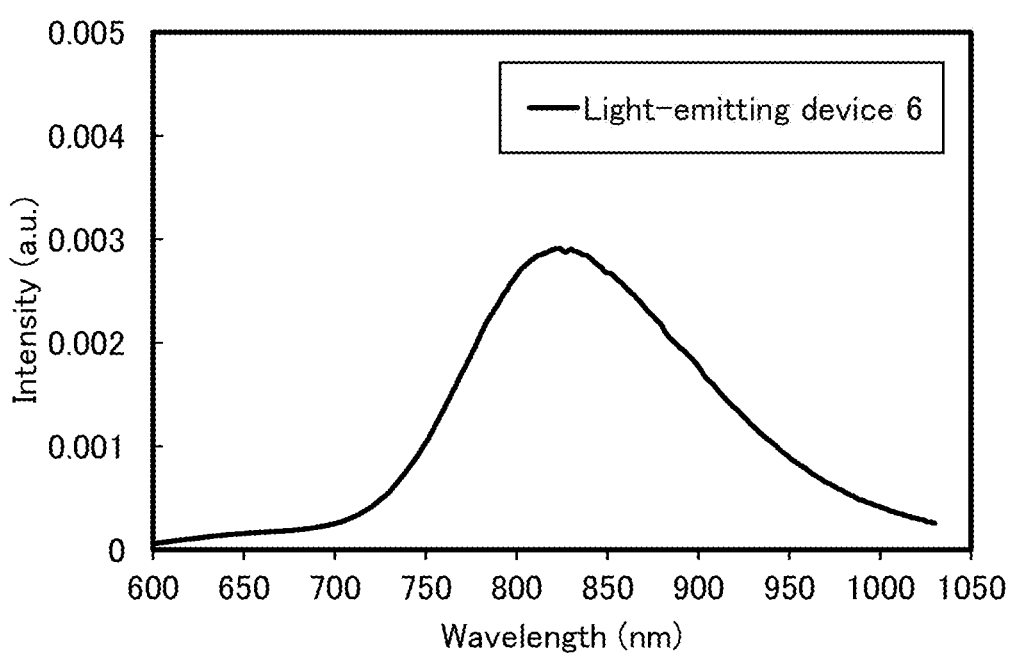
FIG. 26 shows an emission spectrum of the light-emitting device 6.

FIG. 26 shows an emission spectrum when current at a current density of 12 mA/cm² was supplied to the light-emitting device 6. As shown in FIG. 26, the emission spectrum of the light-emitting device 6 has a peak at around 820 nm, which is presumably derived from light emission of PCAP2TDQn contained in the light-emitting layer 913.

Example 7

In this example, thermogravimetry was performed on YGA2TDQn (100), PCA2TDQn (200), and PCAP2TDQn (300), which are the organic compounds of embodiments of the present invention. Note that a thermogravimeter-differential thermal analyzer (TG-DTA) was used as a measurement apparatus for this analysis. The structural formulae of the measured organic compounds are shown below.

[Chemical Formulae 55]

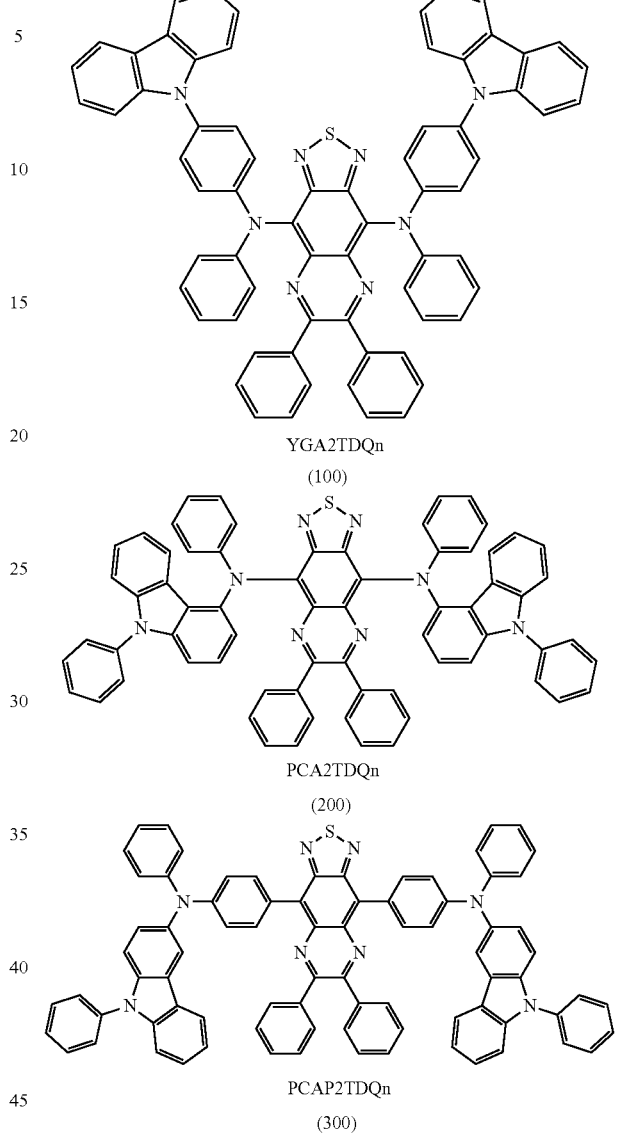

YGA2TDQn
(100)

PCA2TDQn
(200)

PCAP2TDQn
(300)

Figure 27:
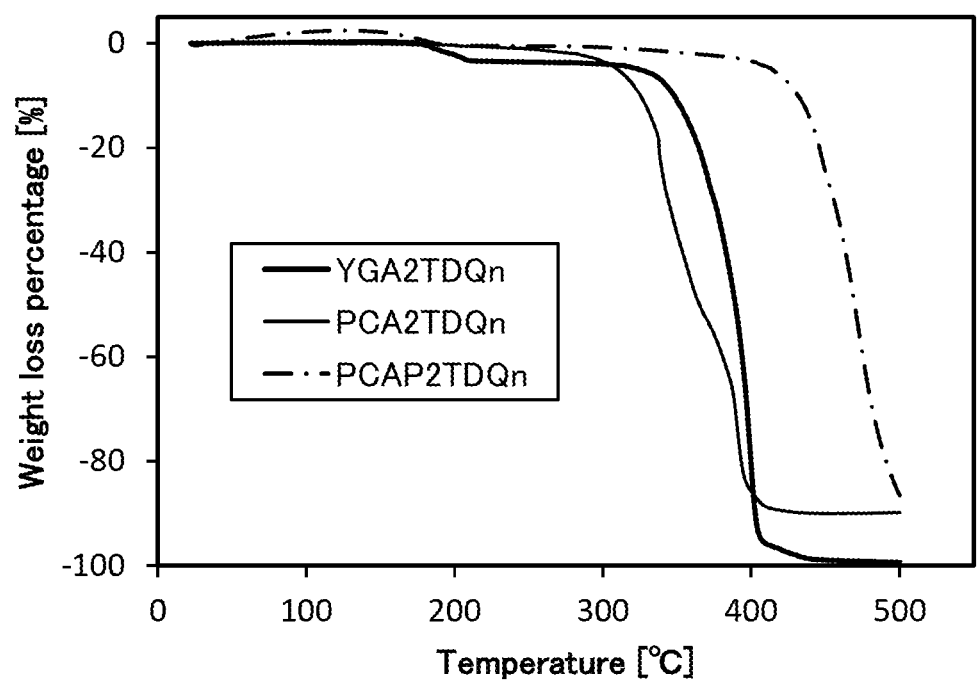
FIG. 27 shows measurement results of organic compounds with a TG-DTA.

FIG. 27 shows measurement results of thermogravimetry. In FIG. 27, the horizontal axis represents temperature, and the vertical axis represents weight loss percentage.

The measurement results indicate that the weight reduction start temperatures (the temperatures at which the weight is reduced by 5% from the start of measurement) of YGA2TDQn and PCA2TDQn were approximately 100° C. lower than that of PCAP2TDQn. Thus, it was confirmed that YGA2TDQn and PCA2TDQn have higher sublimation properties than PCAP2TDQn and can be deposited at low temperatures.

The difference in weight loss percentage depending on temperature is presumably caused by a molecular structure. YGA2TDQn and PCA2TDQn have a structure in which a central skeleton, 6,7-diphenyl-[1,2,5]thiadiazole[3,4-g]quinoxaline, is directly bonded to an amino group. In contrast, PCAP2TDQn has a structure in which the central skeleton is directly bonded to an amino group via a phenylene group.

Thus, among the organic compounds of embodiments of the present invention, the organic compound having the structure in which the central skeleton, 6,7-diphenyl-[1,2,5]thiadiazole[3,4-g]quinoxaline, is directly bonded to an amino group is especially useful in low-temperature deposition.

This application is based on Japanese Patent Application Serial No. 2019-130550 filed with Japan Patent Office on Jul. 12, 2019, the entire contents of which are hereby incorporated by reference.

What is claimed is:

1. An organic compound represented by General Formula (G1):

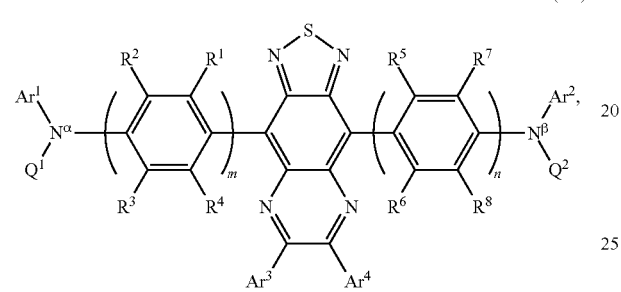

(G1)

wherein $Ar^1$ to $Ar^4$ each independently represent a substituted or unsubstituted aryl group having 6 to 13 carbon atoms in a ring, wherein $R^1$ to $R^8$ each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring, wherein $Q^1$ and $Q^2$ each independently represent a substituted or unsubstituted group having a carbazole skeleton or a substituted or unsubstituted group having a triarylamine skeleton and having 18 to 30 carbon atoms in a ring, wherein three aryl groups in the triarylamine skeleton have the same structure or different structures, and wherein m and n each independently represent 0 or 1.

2. The organic compound according to claim 1, wherein $Q^1$ and $Q^2$ are each independently represented by any one of General Formulae (Q-1), (Q-2), and (Q-3):

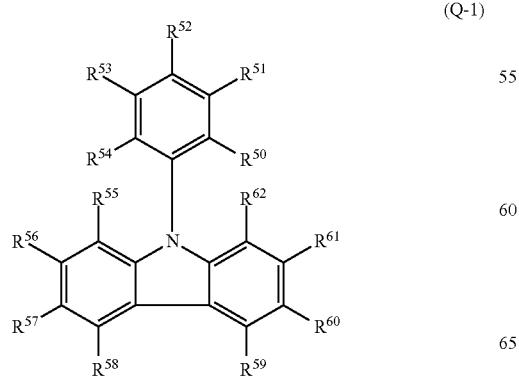

(Q-1)

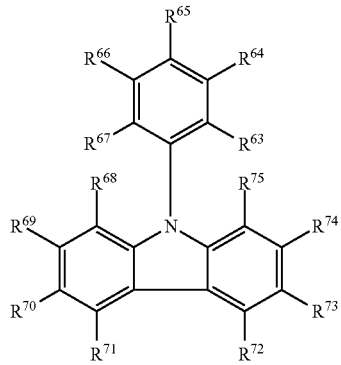

(Q-2)

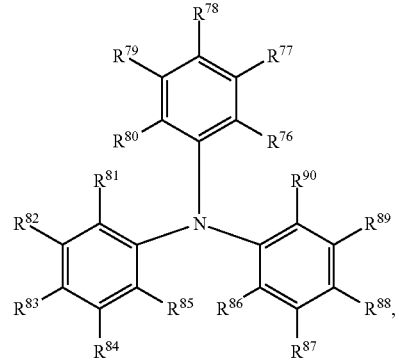

(Q-3)

wherein in General Formula (Q-1), any one of $R^{50}$ to $R^{54}$ is bonded to nitrogen that is $N^\alpha$ or $N^\beta$ in General Formula (G1), and the others each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring, wherein in General Formula (Q-2), any one of $R^{72}$ to $R^{75}$ is bonded to nitrogen that is $N^\alpha$ or $N^\beta$ in General Formula (G1), and the others each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring, wherein in General Formula (Q-3), any one of $R^{76}$ to $R^{80}$ is bonded to nitrogen that is $N^\alpha$ or $N^\beta$ in General Formula (G1), and the others each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring, and wherein $R^{55}$ to $R^{62}$, $R^{63}$ to $R^{71}$, and $R^{81}$ to $R^{90}$ each independently represent any one of hydrogen, an alkyl group having 1 to 6 carbon atoms, a substituted or unsubstituted aryl group having 6 to 13 carbon atoms in a ring, a cycloalkyl group having 3 to 6 carbon atoms, and a substituted or unsubstituted heteroaryl group having 3 to 13 carbon atoms in a ring.

3. The organic compound according to claim 1,
wherein $Ar^1$ to $Ar^4$ are each independently represented by any one of General Formulae (Ar-1), (Ar-2), and (Ar-3):

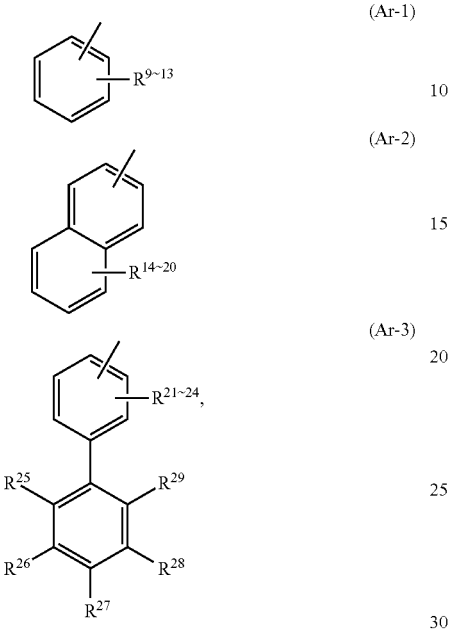

and
wherein $R^9$ to $R^{29}$ each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring.

4. An organic compound represented by General Formula (G2):

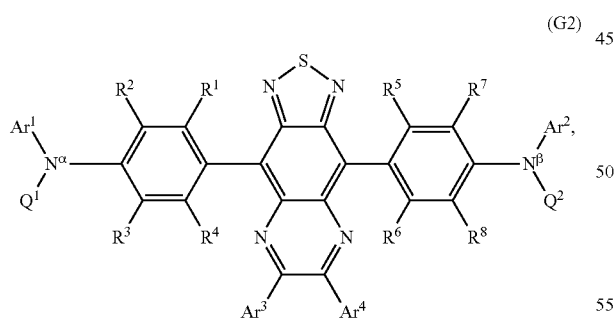

wherein $Ar^1$ to $Ar^4$ each independently represent a substituted or unsubstituted aryl group having 6 to 13 carbon atoms in a ring,
wherein $R^1$ to $R^8$ each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring, wherein $Q^1$ and $Q^2$ each independently represent a substituted or unsubstituted group having a carbazole skeleton or a substituted or unsubstituted group having a triarylamine skeleton and having 18 to 30 carbon atoms in a ring, and
wherein three aryl groups in the triarylamine skeleton have the same structure or different structures.

5. The organic compound according to claim 4,
wherein $Q^1$ and $Q^2$ are each independently represented by any one of General Formulae (Q-1), (Q-2), and (Q-3):

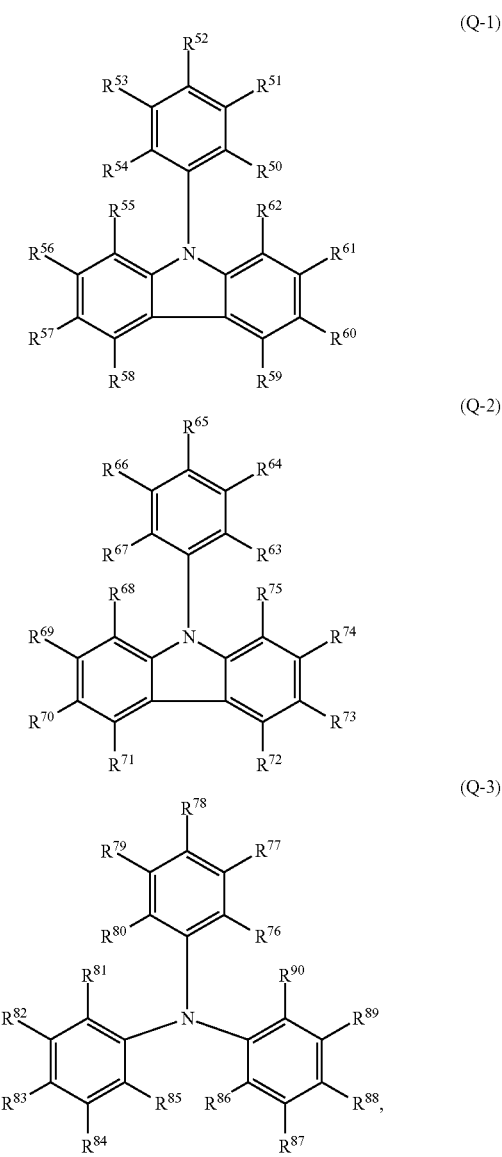

wherein in General Formula (Q-1), any one of $R^{50}$ to $R^{54}$ is bonded to nitrogen that is $N^\alpha$ or $N^\beta$ in General Formula (G2), and the others each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring,
wherein in General Formula (Q-2), any one of $R^{72}$ to $R^{75}$ is bonded to nitrogen that is $N^\alpha$ or $N^\beta$ in General Formula (G2), and the others each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring, wherein in General Formula (Q-3), any one of $R^{76}$ to $R^{80}$ is bonded to nitrogen that is $N^\alpha$ or $N^\beta$ in General Formula (G2), and the others each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring, and wherein $R^{55}$ to $R^{62}$, $R^{63}$ to $R^{71}$, and $R^{81}$ to $R^{90}$ each independently represent any one of hydrogen, an alkyl group having 1 to 6 carbon atoms, a substituted or unsubstituted aryl group having 6 to 13 carbon atoms in a ring, a cycloalkyl group having 3 to 6 carbon atoms, and a substituted or unsubstituted heteroaryl group having 3 to 13 carbon atoms in a ring.

6. The organic compound according to claim 4, wherein $Ar^1$ to $Ar^4$ are each independently represented by any one of General Formulae (Ar-1), (Ar-2), and (Ar-3):

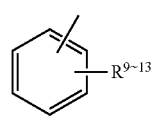

(Ar-1)

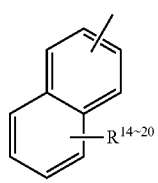

(Ar-2)

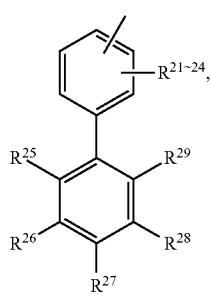

(Ar-3)

and wherein $R^9$ to $R^{29}$ each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring.

7. An organic compound represented by General Formula (G3):

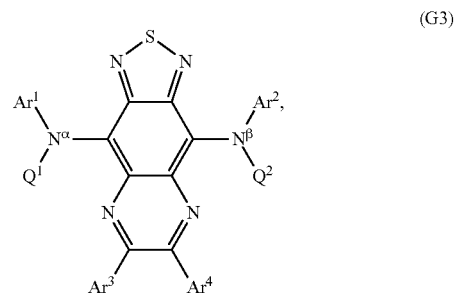

(G3)

wherein $Ar^1$ to $Ar^4$ each independently represent a substituted or unsubstituted aryl group having 6 to 13 carbon atoms in a ring, wherein $Q^1$ and $Q^2$ each independently represent a substituted or unsubstituted group having a carbazole skeleton or a substituted or unsubstituted group having a triarylamine skeleton and having 18 to 30 carbon atoms in a ring, and wherein three aryl groups in the triarylamine skeleton have the same structure or different structures.

8. The organic compound according to claim 7, wherein $Q^1$ and $Q^2$ are each independently represented by any one of General Formulae (Q-1), (Q-2), and (Q-3):

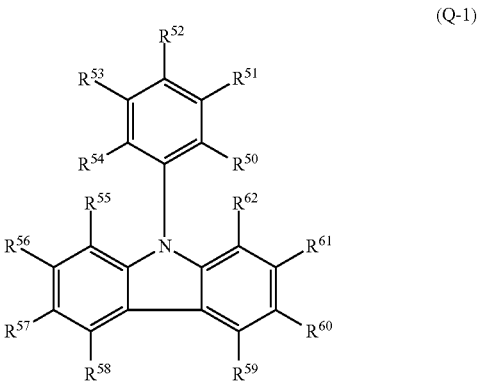

(Q-1)

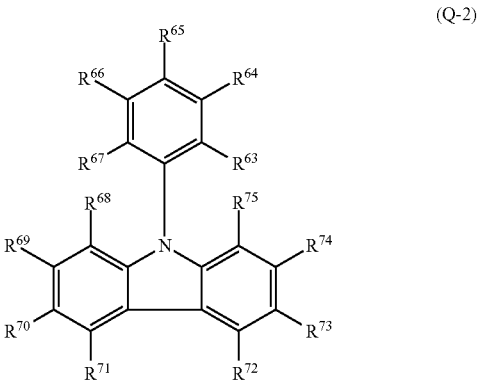

(Q-2)

-continued

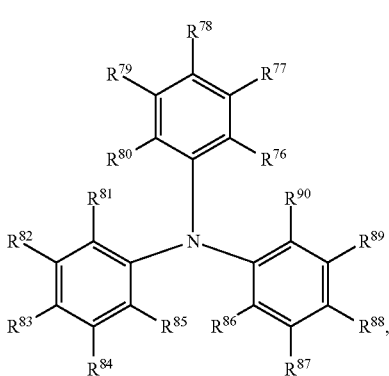

(Q-3)

wherein in General Formula (Q-1), any one of $R^{50}$ to $R^{54}$ is bonded to nitrogen that is $N^\alpha$ or $N^\beta$ in General Formula (G3), and the others each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring, wherein in General Formula (Q-2), any one of $R^{72}$ to $R^{75}$ is bonded to nitrogen that is $N^\alpha$ or $N^\beta$ in General Formula (G3), and the others each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring, wherein in General Formula (Q-3), any one of $R^{76}$ to $R^{80}$ is bonded to nitrogen that is $N^\alpha$ or $N^\beta$ in General Formula (G3), and the others each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring, and wherein $R^{55}$ to $R^{62}$, $R^{63}$ to $R^{71}$, and $R^{81}$ to $R^{90}$ each independently represent any one of hydrogen, an alkyl group having 1 to 6 carbon atoms, a substituted or unsubstituted aryl group having 6 to 13 carbon atoms in a ring, a cycloalkyl group having 3 to 6 carbon atoms, and a substituted or unsubstituted heteroaryl group having 3 to 13 carbon atoms in a ring.

9. The organic compound according to claim 4, wherein the General Formula (G2) is represented by General Formula (G4):

(G4)

wherein $R^{63}$ to $R^{72}$ and $R^{74}$ to $R^{75}$ each independently represent any one of hydrogen, an alkyl group having 1 to 6 carbon atoms, a substituted or unsubstituted aryl group having 6 to 13 carbon atoms in a ring, a cycloalkyl group having 3 to 6 carbon atoms, and a substituted or unsubstituted heteroaryl group having 3 to 13 carbon atoms in a ring.

10. The organic compound according to claim 7, wherein the General Formula (G3) is represented by General Formula (G5):

(G5)

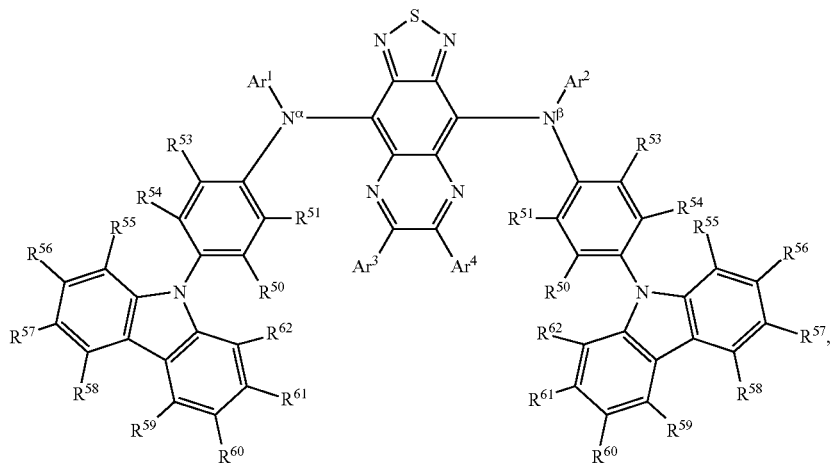

wherein R⁵⁰ to R⁵¹ and R⁵³ to R⁶² each independently represent any one of hydrogen, an alkyl group having 1 to 6 carbon atoms, a substituted or unsubstituted aryl group having 6 to 13 carbon atoms in a ring, a cycloalkyl group having 3 to 6 carbon atoms, and a substituted or unsubstituted heteroaryl group having 3 to 13 carbon atoms in a ring.

11. The organic compound according to claim 7, wherein the General Formula (G3) is represented by General Formula (G6):

(G6)

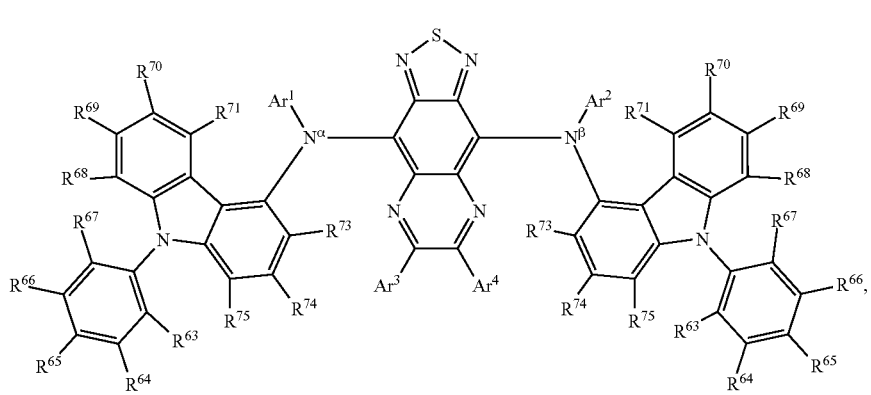

wherein R⁶³ to R⁷¹ and R⁷³ to R⁷⁵ each independently represent any one of hydrogen, an alkyl group having 1 to 6 carbon atoms, a substituted or unsubstituted aryl group having 6 to 13 carbon atoms in a ring, a cycloalkyl group having 3 to 6 carbon atoms, and a substituted or unsubstituted heteroaryl group having 3 to 13 carbon atoms in a ring.

12. The organic compound according to claim 7, wherein Ar¹ to Ar⁴ are each independently represented by any one of General Formulae (Ar-1), (Ar-2), and (Ar-3):

(Ar-1)

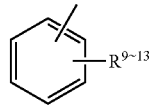

-continued (Ar-2)

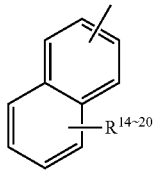

-continued

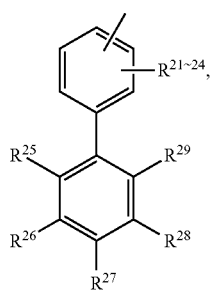

(Ar-3)

and wherein $R^9$ to $R^{29}$ each independently represent any one of hydrogen, an alkyl group having 1 to 6 carbon atoms, a cycloalkyl group having 3 to 6 carbon atoms, a substituted or unsubstituted aryl group having 6 to 13 carbon atoms in a ring, and a substituted or unsubstituted heteroaryl group having 3 to 13 carbon atoms in a ring.

13. A light-emitting device comprising the organic compound according to claim 1.

14. The light-emitting device according to claim 13, further comprising an EL layer between a pair of electrodes, wherein the EL layer comprises the organic compound.

15. The light-emitting device according to claim 14, wherein the EL layer comprises a light-emitting layer, and wherein the light-emitting layer comprises the organic compound.

16. The light-emitting device according to claim 13, wherein an emission spectrum peak is positioned at a wavelength longer than 850 nm and an absorption spectrum peak is positioned at a wavelength longer than 600 nm.

17. A light-emitting apparatus comprising:
the light-emitting device according to claim 13; and
at least one of a transistor and a substrate.

18. An electronic device comprising:
the light-emitting apparatus according to claim 17; and
at least one of a microphone, a camera, an operation button, an external connection portion, and a speaker.

19. A lighting device comprising:
the light-emitting device according to claim 13; and
at least one of a housing, a cover, and a support.

20. An organic compound represented by Structural Formula (100), Structural Formula (200), or Structural Formula (300):

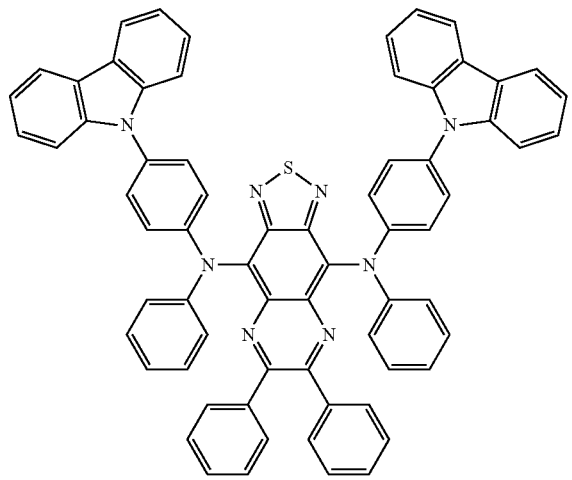

(100)

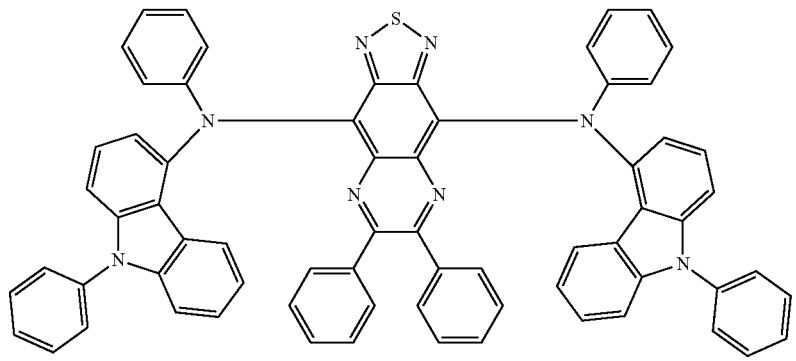

(200)

-continued
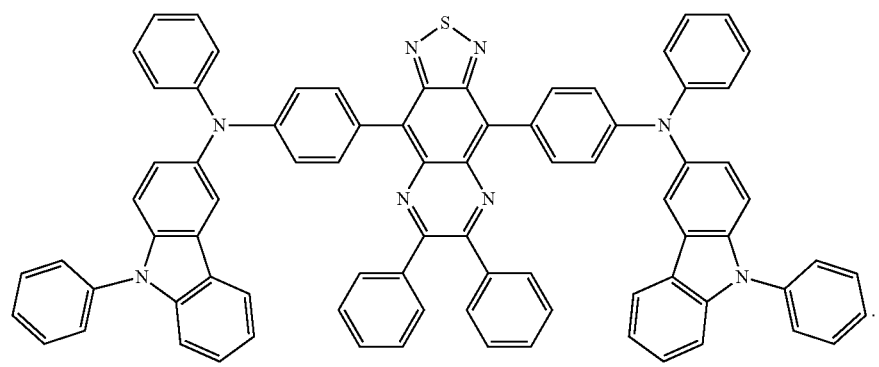
(300)
* * * * *